(12) United States Patent
Stump

(10) Patent No.: US 12,089,914 B2
(45) Date of Patent: Sep. 17, 2024

(54) ENHANCED PHYSIOLOGICAL MONITORING DEVICES AND COMPUTER-IMPLEMENTED SYSTEMS AND METHODS OF REMOTE PHYSIOLOGICAL MONITORING OF SUBJECTS

(71) Applicant: Sempulse Corporation, San Marcos, TX (US)

(72) Inventor: Kurt Stump, San Diego, CA (US)

( * ) Notice: Subject to any disclaimer, the term of this patent is extended or adjusted under 35 U.S.C. 154(b) by 1014 days.

(21) Appl. No.: 17/026,929

(22) Filed: Sep. 21, 2020

(65) Prior Publication Data

US 2021/0000347 A1 Jan. 7, 2021

Related U.S. Application Data

(63) Continuation-in-part of application No. 16/593,354, filed on Oct. 4, 2019, now abandoned, which is a
(Continued)

(51) Int. Cl.
*A61B 5/024* (2006.01)
*A61B 5/00* (2006.01)
(Continued)

(52) U.S. Cl.
CPC .......... *A61B 5/0022* (2013.01); *A61B 5/0205* (2013.01); *A61B 5/021* (2013.01);
(Continued)

(58) Field of Classification Search
CPC ..... A61B 5/0022; A61B 5/0205; A61B 5/021; A61B 5/11; A61B 5/14551; A61B 5/33; A61B 5/742; A61B 5/7475; G16H 50/30
(Continued)

(56) References Cited

U.S. PATENT DOCUMENTS 4,981,139 A   1/1991  Pfohl
5,673,692 A  10/1997  Schulze et al.
(Continued)

FOREIGN PATENT DOCUMENTS

CA    2586839 A1   5/2006
CN  202096392 U   1/2012
(Continued)

OTHER PUBLICATIONS

Kim, C.S., et al., "Ballistocardiogram as Proximal Timing Reference for Pulse Transit Time Measurement: Potential for Cuffless Blood Pressure Monitoring," IEEE Transactions on Biomedical Engineering, vol. 62, No. 11, Nov. 2015, 10pgs http://www.ncbi.nlm.nih.gov/pubmed/26054058.
(Continued)

*Primary Examiner* — John R Downey
(74) *Attorney, Agent, or Firm* — Duane Morris LLP

(57) ABSTRACT

Physiological sign monitoring devices, and systems and computer-implemented methods of remote physiological monitoring of subjects. A monitoring device includes a plurality of physiological sign monitoring portions. Each physiological sign monitoring portion of the device is configured for deployment on a different, respective surface of a subject including a surface on the back of an ear of the subject, a surface over a mastoid region of the neck of the subject, and a surface over another region of the neck of the subject. Each physiological sign monitoring portion of the device includes a plurality of physiological sensors, where each sensor is configured to generate a respective electronic signal based on a respective monitored physiological parameter of the subject. At least one physiological sensor in each physiological sign monitoring portion of the device is configured to generate a respective electronic signal based on the same monitored physiological parameter of the subject.

20 Claims, 23 Drawing Sheets

Related U.S. Application Data continuation-in-part of application No. 15/889,992, filed on Feb. 6, 2018, now abandoned, which is a continuation of application No. 14/812,696, filed on Jul. 29, 2015, now Pat. No. 9,883,801.

(60) Provisional application No. 62/081,185, filed on Nov. 18, 2014, provisional application No. 62/030,314, filed on Jul. 29, 2014.

(51) Int. Cl.

| | | |
|---|---|---|
| A61B 5/0205 | (2006.01) | |
| A61B 5/021 | (2006.01) | |
| A61B 5/11 | (2006.01) | |
| A61B 5/1455 | (2006.01) | |
| A61B 5/33 | (2021.01) | |
| G16H 40/20 | (2018.01) | |
| G16H 50/30 | (2018.01) | |

(52) U.S. Cl.
CPC ............ *A61B 5/02444* (2013.01); *A61B 5/11* (2013.01); *A61B 5/14551* (2013.01); *A61B 5/33* (2021.01); *A61B 5/742* (2013.01); *A61B 5/7475* (2013.01); *G16H 50/30* (2018.01); *A61B 5/72* (2013.01); *A61B 2560/0257* (2013.01); *G16H 40/20* (2018.01)

(58) Field of Classification Search
USPC .................................................. 600/300, 301
See application file for complete search history.

(56) References Cited

U.S. PATENT DOCUMENTS

| | | |
|---|---|---|
| 5,919,141 A | 7/1999 | Money et al. |
| 5,931,791 A | 8/1999 | Saltzstein et al. |
| 6,198,394 B1 | 3/2001 | Jacobsen et al. |
| 6,416,471 B1 | 7/2002 | Kumar et al. |
| 6,419,630 B1 | 7/2002 | Taylor, Jr. et al. |
| 6,544,173 B2 | 4/2003 | West et al. |
| 6,556,852 B1 | 4/2003 | Schulze et al. |
| 6,733,447 B2 | 5/2004 | Lai et al. |
| 7,263,396 B2 | 8/2007 | Chen et al. |
| 7,292,883 B2 * | 11/2007 | De Felice ............ A61B 5/14551 600/324 |
| 7,803,120 B2 | 9/2010 | Banet et al. |
| 8,043,213 B2 | 10/2011 | Hatlestad et al. |
| 8,287,452 B2 | 10/2012 | Young et al. |
| 8,308,641 B2 | 11/2012 | Moroney et al. |
| 8,346,573 B2 | 1/2013 | Glimp et al. |
| 8,352,285 B2 | 1/2013 | Hitney et al. |
| 8,373,556 B2 | 2/2013 | LaLonde et al. |
| 8,403,846 B1 | 3/2013 | Cienfuegos |
| 8,449,469 B2 | 5/2013 | Banet et al. |
| 8,588,880 B2 | 11/2013 | Abdul-Hafiz et al. |
| 8,591,411 B2 | 11/2013 | Banet et al. |
| 8,700,425 B2 | 4/2014 | Hitney et al. |
| 2002/0099277 A1 | 7/2002 | Harry et al. |
| 2008/0077020 A1 | 3/2008 | Young et al. |
| 2008/0165017 A1 | 7/2008 | Schwartz |
| 2009/0069642 A1* | 3/2009 | Gao ...................... H04L 67/125 600/300 |
| 2009/0131759 A1* | 5/2009 | Sims .................... A61B 5/1135 600/301 |
| 2009/0240116 A1 | 9/2009 | Bluth |
| 2010/0305412 A1 | 12/2010 | Darrah et al. |
| 2011/0137141 A1 | 6/2011 | Razoumov et al. |
| 2012/0203077 A1* | 8/2012 | He ..................... A61B 5/02055 600/382 |
| 2012/0226112 A1 | 9/2012 | LeBoeuf et al. |
| 2013/0014706 A1 | 1/2013 | Menkes |
| 2013/0035581 A1 | 2/2013 | Vesto |
| 2014/0073043 A1 | 3/2014 | Holmes |
| 2014/0152673 A1* | 6/2014 | Lynn ...................... G06T 13/80 345/473 |
| 2014/0227671 A1* | 8/2014 | Olmstead ................ G11B 27/10 386/226 |
| 2014/0257122 A1* | 9/2014 | Ong ...................... A61B 5/0205 705/2 |
| 2016/0029890 A1* | 2/2016 | Stump .................. A61B 5/0205 600/301 |
| 2019/0180879 A1* | 6/2019 | Jain ......................... G16H 10/20 |
| 2022/0160309 A1* | 5/2022 | Poltorak ................. H04W 4/38 |

FOREIGN PATENT DOCUMENTS

| | | |
|---|---|---|
| EP | 0553372 B1 | 11/1996 |
| WO | 02/22006 A1 | 3/2002 |
| WO | 02/40091 A2 | 5/2002 |
| WO | 2005/046433 A2 | 5/2005 |
| WO | 2009069163 A1 | 6/2009 |
| WO | 2010103390 A1 | 9/2010 |
| WO | 2012112407 A1 | 8/2012 |
| WO | 2013027027 A2 | 2/2013 |

OTHER PUBLICATIONS

Mukkamala, R., et al., "Toward Ubiquitous Blood Pressure Monitoring via Pulse Transit Time: Theory and Practice", IEEE Transactions on Biomedical Engineering, vol. 62, No. 8, Aug. 2015, 25pgs. http://www.ncbi.nlm.nih.gov/pubmed/26057530.

Wiens, A., et al., "Wearable Ballistocardiography: Preliminary Methods for Mapping Surface Vibration Measurements to Whole Body Forces", School of Electrical and Computer Engineering, Georgia Institute of Technology, 6pgs. http://ieeexplore.ieee.org/xpl/login.jsp?tp=&arnumber=6944790&url=http%3A%2F%2Fieeexplore.ieee.org%2Fxpls%2Fabs_all.jsp%3Farnumber%3D6944790.

International Bureau of WIPO, International Preliminary Report on Patentability for corresponding International Application No. PCT/US15/42695 dated Jan. 31, 2017, 7pgs.

International Searching Authority, International Search Report for corresponding International Application No. PCT/US15/42695 Mailed Oct. 29, 2015, 1pg.

\* cited by examiner

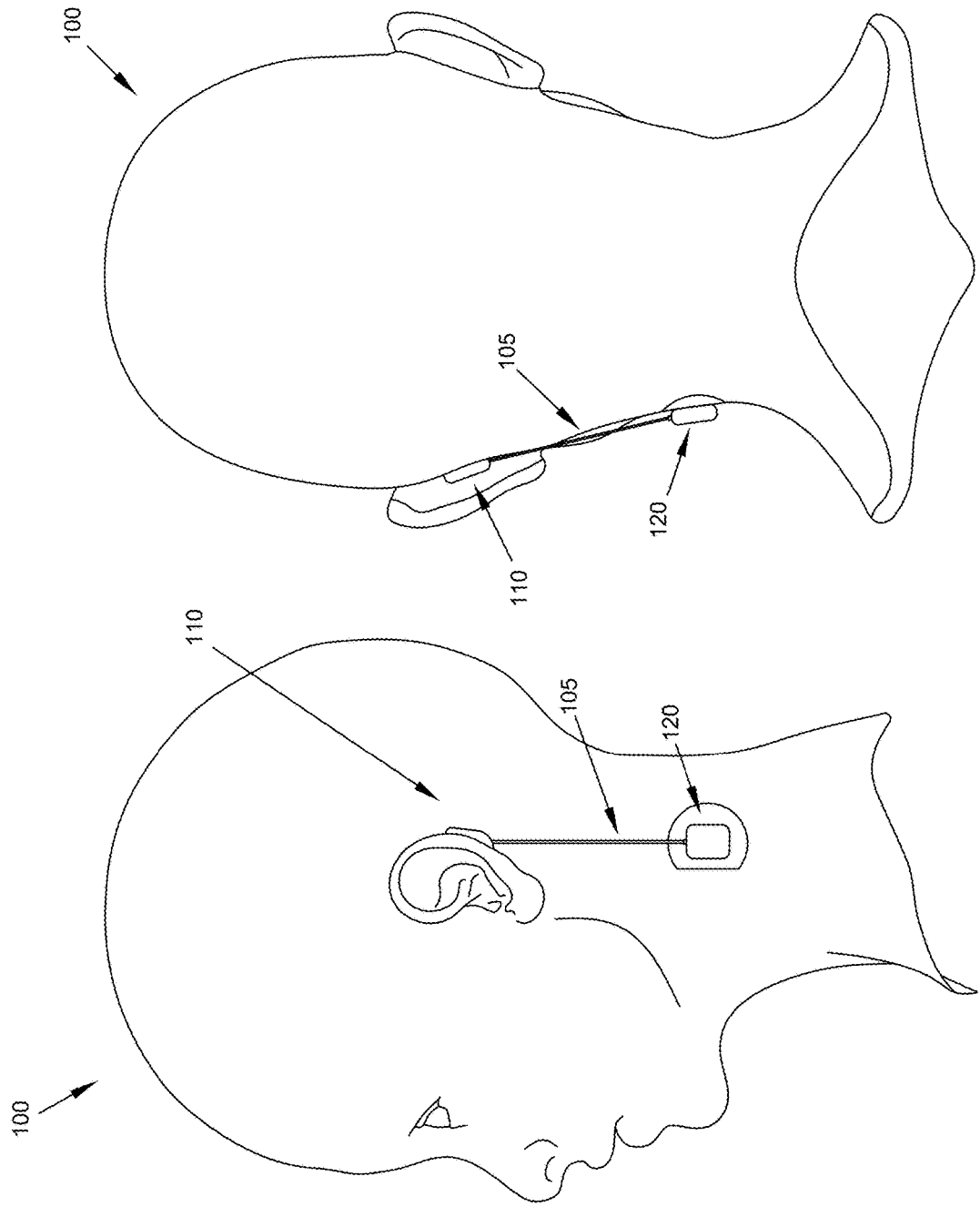

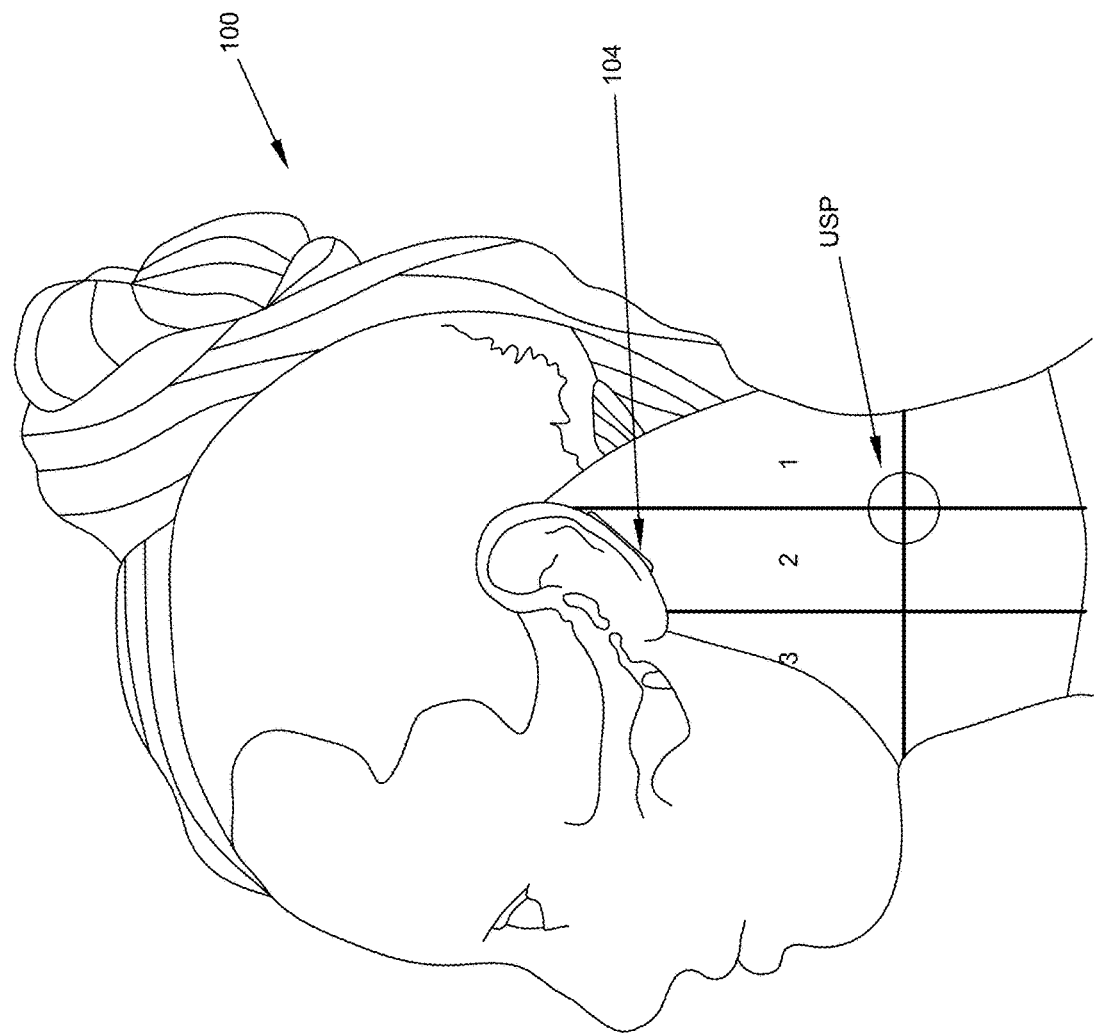

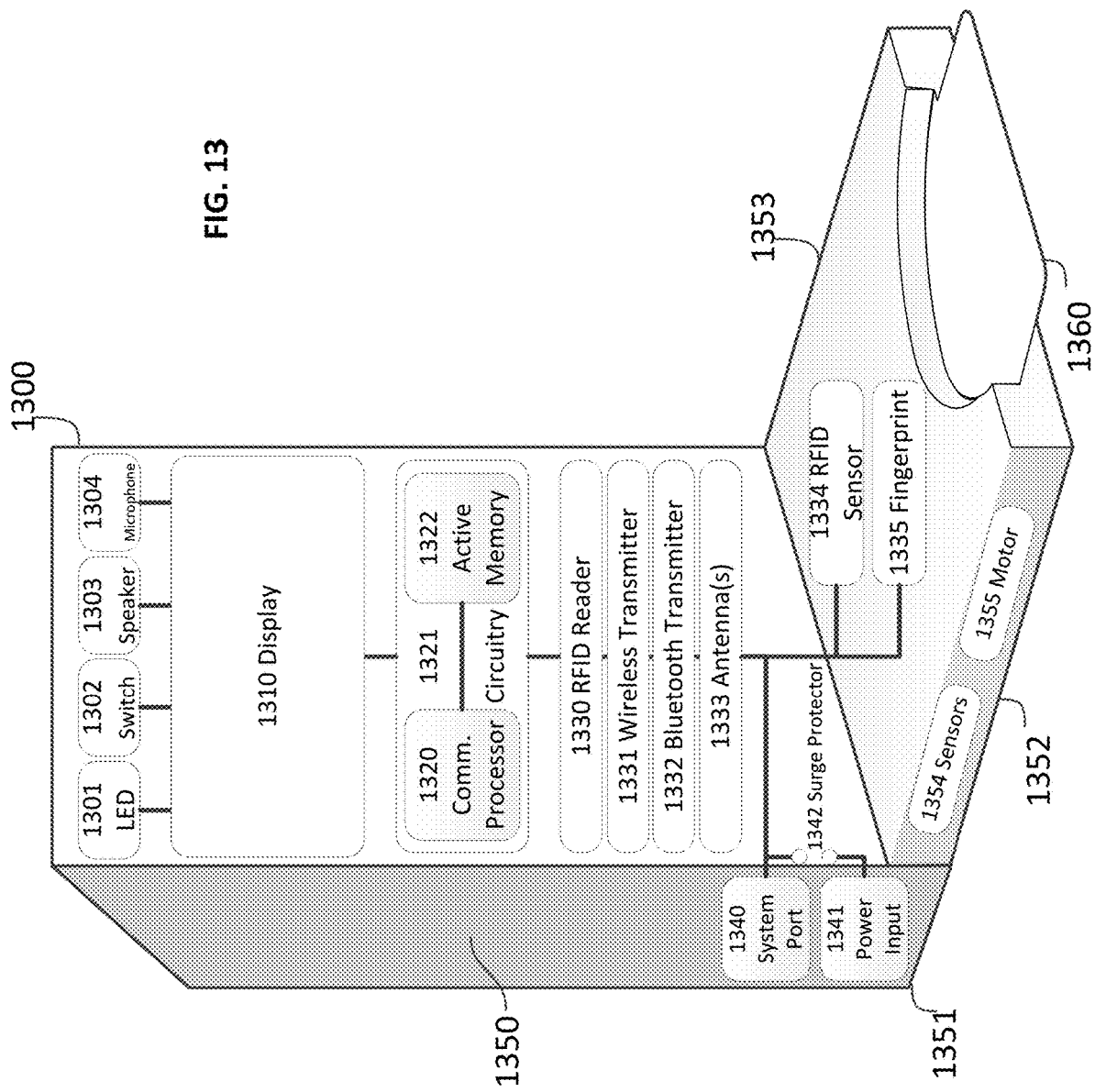

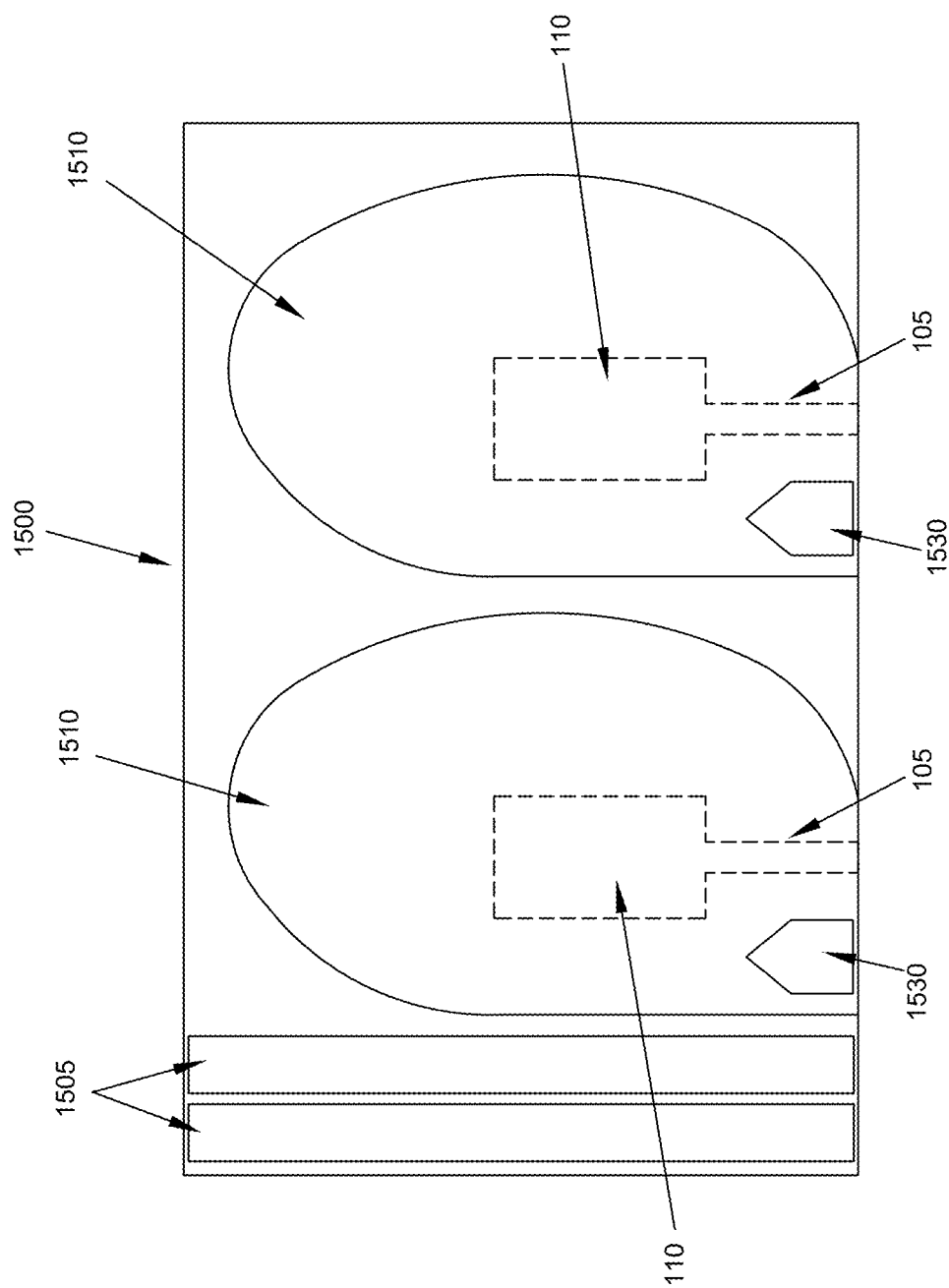

ENHANCED PHYSIOLOGICAL MONITORING DEVICES AND COMPUTER-IMPLEMENTED SYSTEMS AND METHODS OF REMOTE PHYSIOLOGICAL MONITORING OF SUBJECTS

CROSS-REFERENCE TO RELATED APPLICATIONS

This application is a continuation-in-part application of and claims priority to U.S. patent application Ser. No. 16/593,354, filed on Oct. 4, 2019, the entirety of which is herein incorporated by reference, which is a continuation-in-part application of and claims priority to U.S. patent application Ser. No. 15/889,992, filed on Feb. 6, 2018, the entirety of which is herein incorporated by reference, which claimed priority to U.S. patent application Ser. No. 14/812,696, filed on Jul. 29, 2015, the entirety of which is herein incorporated by reference, which claimed priority to U.S. Provisional Patent Application Ser. No. 62/030,314, filed on Jul. 29, 2014, and to U.S. Provisional Patent Application Ser. No. 62/081,185, filed on Nov. 18, 2014, the entirety of which are herein incorporated by reference.

FIELD

The present disclosure is directed generally to monitoring and analyzing data and more particularly to enhanced physiological monitoring devices and computer implemented systems and methods of remote physiological monitoring of subjects.

DESCRIPTION OF THE RELATED ART

Monitoring of a subject's (e.g., an ambulatory or hospitalized patient's) vital or physiological signs has become increasingly important in today's society, particularly those persons and patients who are seriously ill or injured. For example, virtually every hospitalized patient requires periodic measurement and logging of temperature, pulse rate, and blood pressure. Many patients also need frequent determination of respiration rate, cardiac activity, and other physiological signs. Various conventional techniques for monitoring a patient's vital signs rely on dedicated equipment that is either physically attached to the patient or periodically attached to, and removed from, the patient via dexterous, manual means.

However, these conventional monitoring techniques are very costly, and both labor and time-intensive, and such conventional monitoring equipment is very expensive and not readily disposable. These conventional techniques and equipment are also ineffective at monitoring ambulatory patients. Further, such dedicated equipment is highly sensitive, and designed and tested for sterile ambulatory and hospital conditions, which leaves government, commercial, and military health providers and first responders without an effective solution for monitoring ambulatory patients, especially in trauma, battlefield, natural disaster, or terrorist attack, scenarios where mud, blood, and other contaminates are prevalent. In such mass casualty scenarios, government, commercial, and military health providers and first responders have seen the critical need to compress cycle time in their casualty monitoring, evaluation, decision-making, and treatment. In a recently published study from 2001-2009, over 50% of the U.S. combat fatalities in Iraq and Afghanistan died from injuries that were deemed "Potentially Survivable." Many civilian, commercial health sectors also share similar challenges. Current administrative policies, and an aging demographic, have resulted in a 25% annual increase in emergency room wait times. The problem continues to grow as over 800,000 people visit emergency rooms and urgent care centers in the U.S. daily, and longer wait times equate to more deaths, posing a significant risk and liability of a humanitarian disaster. What is needed are cost-effective systems and methods for real-time, continuous monitoring of physiological and environmental parameters of ambulatory, or hospitalized, subjects, and dynamic, automated prognoses, and triage prioritization, in mass casualty scenarios and environments.

Mobile devices such as cellular phones, Personal Digital Assistants (PDAs), smart phones, tablet computers, other wirelessly enabled devices, other portable handheld devices, and hands-free/heads-up devices, have successfully penetrated and been adopted by the general consumer market and by many government entities. Functionalities on mobile devices are generally performed by software applications either in the form of software components that are built-in to the device's mobile operating system or separate mobile applications (also known as "mobile apps" or "apps") that run on the device's operating system. Recently, the development and use of mobile apps has become prevalent and now exist across a wide array of mobile device platforms. Individuals, businesses, and government agencies have come to enjoy, appreciate and rely on the convenience, flexibility and mobility of mobile devices as a means to readily obtain access to information, facilitate communications and interact with friends, family, colleagues and business entities, other friendly deployed units, etc. Thus, it is critical that systems and methods for real-time delivery of information to information users (e.g., first responders, medical providers, etc.) place the information at the fingertips of the users in order to permit enhanced real-time decision-making.

Wearables, such as, for example, Fitbit® wearables, Jawbone® fitness trackers, and the Apple® Watch, have become increasingly popular especially among fitness and health enthusiasts. Conventional wearables are generally worn on the wrist of a user and provide heart rate monitoring, as well as tracking and recording of the user's activity such as steps, distance, calories burned, floors climbed, active minutes, running/walking/cycling pace, exercise workout summaries, sleep, etc. However, deploying such wearables on extremity locations such as the wrist introduces significant errors associated with vital or physiological sign measurement. For example, hair, tattoos, impact, limited blood flow, and motion, restrict and/or introduce inaccuracies associated with various vital sign measurements. Moreover, the body naturally restricts blood flow to extremities during emergency situations (e.g., cold temperatures and emotional stress). Thus, it is critical that systems, methods, and devices for real-time, continuous monitoring of physiological parameters of ambulatory or hospitalized subjects monitor such parameters at body locations that are prone to minimal hair, high blood flow, and/or limited or predictable motion, especially during emergency situations, to ensure accurate results.

Like the accelerated adoption of the Internet itself, cloud computing is rapidly gaining momentum. Cloud computing refers to a computing model for enabling on-demand network access to a shared pool of configurable information technology (IT) capabilities or resources (e.g., networks, servers, storage, applications, and services) that can be rapidly provisioned and released, e.g., with minimal management effort or service provider interaction. Cloud computing allows users to access technology-based services from a network cloud without knowledge of, expertise with, or control over the technology infrastructure that supports them, much as consumers of electric utilities are agnostic as to details of the underlying electrical grid. The cloud is a service provider's offering of abstracted computing-related services. The cloud computing model generally enables on-demand computing self-service, ubiquitous network access, location independent resource pooling, rapid elasticity (e.g., quick demand-based resource scaling), and measured computing service.

Cloud computing models permit service providers to offer services on an on-demand or as-needed (e.g., subscription basis) and customers to purchase (or rent) computer infrastructure-related services as an outsourced service (e.g., on an as-needed or as-consumed basis) instead of having to purchase equipment (e.g., servers, software, data center space, or network equipment) themselves.

SUMMARY

In some embodiments of the present disclosure, a monitoring device is provided. The monitoring device includes a plurality of physiological sign monitoring portions. Each physiological sign monitoring portion of the monitoring device is configured for deployment on a different, respective surface of a subject. The different, respective surfaces of the subject are a surface on the back of a respective ear (e.g., opposite a concha) of the subject, a surface over a mastoid region of the neck of the subject, a surface over another region of the neck of the subject, and a skull, nose, or face surface of the subject opposite a portion of an eyeglasses physiological sign monitoring portion. Each physiological sign monitoring portion of the monitoring device includes a plurality of physiological sensors. Each physiological sensor is configured to generate a respective electronic signal based on a respective monitored physiological parameter of the subject. The monitored physiological parameters include at least two of photoplethysmogram, electrocardiogram, ballistocardiogram, electrooculogram, skin temperature, skin conductance, skin resistance, head motion relative to a motion axis, neck motion relative to a motion axis, sweat chemistry, sweat composition, head orientation relative to an orientation axis, and neck orientation relative to an orientation axis. At least one physiological sensor in each physiological sign monitoring portion of the monitoring device is configured to generate a respective electronic signal based on the same monitored physiological parameter of the subject.

In some embodiments of the present disclosure, a system for remote physiological monitoring of subjects is provided. The system includes a plurality of monitoring devices. Each monitoring device in the system includes a respective plurality of physiological sign monitoring portions. Each respective physiological sign monitoring portion of each monitoring device is configured for deployment on a different, respective surface of a respective subject. The different, respective surfaces of the subject are a surface on the back of a respective ear (e.g., opposite a concha) of the subject, a surface over a mastoid region of the neck of the subject, a surface over another region of the neck of the subject, and a skull, nose, or face surface of the subject opposite a portion of an eyeglasses physiological sign monitoring portion. Each respective physiological sign monitoring portion of each monitoring device includes a respective plurality of physiological sensors. Each physiological sensor is configured to generate a respective electronic signal based on a respective monitored physiological parameter of the respective subject. The monitored physiological parameters include at least two of photoplethysmogram, electrocardiogram, ballistocardiogram, electrooculogram, skin temperature, skin conductance, skin resistance, head motion relative to a motion axis, neck motion relative to a motion axis, sweat chemistry, sweat composition, head orientation relative to an orientation axis, and neck orientation relative to an orientation axis.

In some embodiments of the present disclosure, a system for remote physiological monitoring of a subject is provided. The system includes a monitoring device including a plurality of physiological sign monitoring portions. Each respective physiological sign monitoring portion of the monitoring device is configured for deployment on a different, respective surface of a respective subject. The different, respective surfaces of the subject are a surface on the back of a respective ear (e.g., opposite a concha) of the subject, a surface over a mastoid region of the neck of the subject, a surface over another region of the neck of the subject, and a skull, nose, or face surface of the subject opposite a portion of an eyeglasses physiological sign monitoring portion. Each respective physiological sign monitoring portion of the monitoring device includes a respective plurality of physiological sensors. Each physiological sensor is configured to generate a respective electronic signal based on a respective monitored physiological parameter of the respective subject. The monitored physiological parameters include at least two of photoplethysmogram, electrocardiogram, ballistocardiogram, electrooculogram, skin temperature, skin conductance, skin resistance, head motion relative to a motion axis, neck motion relative to a motion axis, sweat chemistry, sweat composition, head orientation relative to an orientation axis, and neck orientation relative to an orientation axis.

In some embodiments of the present disclosure, the system also includes a mobile communication and display device. The mobile communication and display device includes a communications interface configured to be coupled to a network and to receive transmitted electronic signals regarding the subject over the network from the monitoring device and a processor coupled to the communications interface. The mobile communication and display device also includes a non-transitory machine-readable storage medium encoded with program code executable by the processor for generating machine readable values indicative of a plurality of physiological signs for the subject using the received electronic signals. The plurality of physiological signs include at least two of heart rate, respiratory rate, pulse oximetry, end-tidal carbon dioxide in a respective subject's blood, cranial temperature, core body temperature, mean arterial blood pressure, systolic blood pressure, diastolic blood pressure, pulse deficit, premature ventricular complexes, maximal oxygen uptake, R-J interval, heart rate variability, pulse transit time, pulse wave velocity, R-R interval, eye movement, electrocardiogram pulse rate, galvanic skin response, hydration level, stress level, bioimpedance, glucose level, subject activity level, coughing, sneezing, or arterial characteristics.

BRIEF DESCRIPTION OF THE DRAWINGS

Various aspects of the present disclosure will be or become apparent to one with skill in the art by reference to the following detailed description when considered in connection with the accompanying exemplary non-limiting embodiments.

FIGS. 1A and 1B is a side and rear perspective view of a head and neck of a subject and illustrating an example of a deployment of an example of an enhanced monitoring device in accordance with some embodiments of the present disclosure.

FIGS. 2A-2C are side perspective views of a head and neck of a subject and illustrating examples of surfaces for example deployments of an enhanced monitoring device according to some embodiments.

FIG. 13 is a block diagram of an example of a monitoring device dispensing unit in accordance with some embodiments of the present disclosure.

FIGS. 15A-15C are perspective views illustrating examples of an adhesive sheet for an example deployment of a physiological sign portion of an enhanced monitoring device in accordance with some embodiments of the present disclosure.

DETAILED DESCRIPTION OF THE EXAMPLES

Figure 2B:
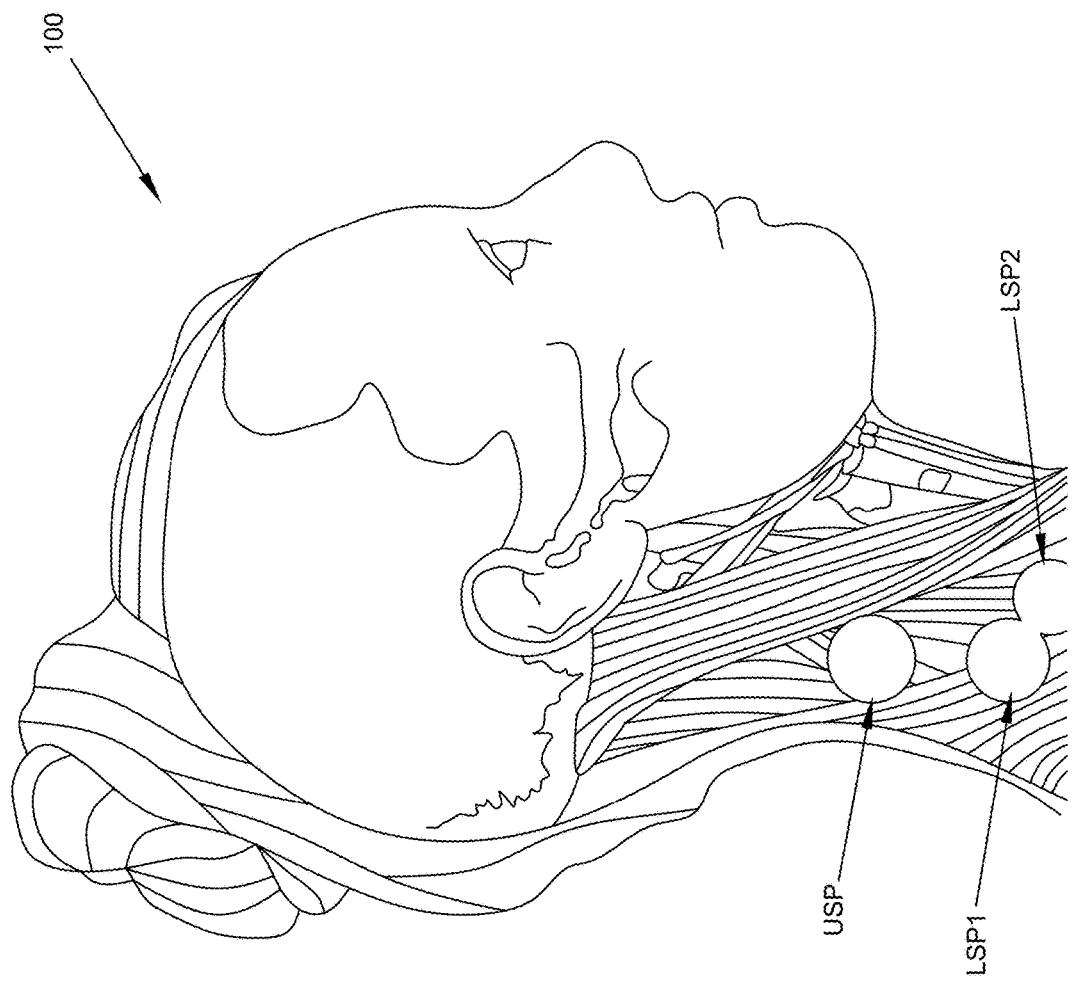

With reference to the Figures, where like elements have been given like numerical designations to facilitate an understanding of the drawings, the various embodiments of systems and computer-implemented methods of automated physiological monitoring, triage, and treatment are described. The figures are not drawn to scale.

Various embodiments address the foregoing deficiencies of prior art systems and methods of monitoring a person's physiological signs and analyzing such information for triage and treatment, especially in trauma, battlefield, emergency room, terrorist attack, or natural disaster scenarios including a pandemic, and provide systems and methods to facilitate dynamic, automatic, real-time prognoses and triage prioritization in such environments to the benefit of government, military, business, individual users (e.g., first responders, emergency medical technicians (EMTs)), patients, and providers of such services, alike. For example, patients benefit from being able to have first responders and EMTs accurately, efficiently treat them and increase the likelihood of saving their lives. Users (first responders, EMTs) benefit from being able to accurately, and in real-time, receive monitored physiological data, prognoses, and triage prioritization, of patients, even in trauma, battlefield, terrorist attack, emergency room, or natural disaster scenarios including a pandemic, to significantly enhance their decision-making and ability to treat subjects and save lives. Government (e.g., military, law enforcement agencies, intelligence agencies) and business (e.g., employers, hospitals) benefit from being able to collect real-time location data, physiological data, prognoses and triage prioritization, to significantly enhance their recordkeeping, provision of care instructions, medical evacuation, casualty evacuation, and alerts notification. Service providers benefit from being able to offer such services on an on-demand or as-needed basis over wireless networks, and the Internet or Web.

The following description is provided as an enabling teaching of a representative set of examples. Many changes can be made to the embodiments described herein while still obtaining beneficial results. Some of the desired benefits discussed below can be obtained by selecting some of the features or steps discussed herein without utilizing other features or steps. Accordingly, many modifications and adaptations, as well as subsets of the features and steps described herein are possible and can even be desirable in certain circumstances. Thus, the following description is provided as illustrative and is not limiting.

This description of illustrative embodiments is intended to be read in connection with the accompanying drawings, which are to be considered part of the entire written description. In the description of embodiments disclosed herein, any reference to direction or orientation is merely intended for convenience of description and is not intended in any way to limit the scope of the present disclosure. Relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description only and do not require that a system or apparatus be constructed or operated in a particular orientation. Terms such as "attached," "affixed," "connected" and "interconnected," refer to a relationship wherein structures are secured or attached to one another either directly or indirectly through intervening structures, as well as both movable or rigid attachments or relationships, unless expressly described otherwise. The term "adjacent" as used herein to describe the relationship between structures/components includes both direct contact between the respective structures/components referenced and the presence of other intervening structures/components between respective structures/components.

As used herein, use of a singular article such as "a," "an" and "the" is not intended to exclude pluralities of the article's object unless the context clearly and unambiguously dictates otherwise.

The inventor has developed systems and methods of automated prognosis and triage prioritization in trauma situations where the number of subjects (e.g., ambulatory patients, soldiers, victims of terrorist attacks or roadside bombs or natural disasters, emergency room patients) exceeds the number of qualified, available medical personnel, and where triage based on the severity of the injuries is critically important. For example, the inventor has determined that enhanced monitoring devices, systems and methods provided herein can provide remote monitoring of one or more subject's physiological parameters from a plurality of predetermined surfaces of the subject (as well as, in some embodiments, location, and orientation, and environmental parameters in the subjects' environment), non-invasively and accurately. In some embodiments, enhanced monitoring devices, systems and methods provided herein can wirelessly transmit generated electronic signals including such subject physiological parameter information to one or more mobile communication and display devices. The inventor has determined that the one or more mobile communication and display devices provided herein can run a native application, web application, or mobile application, programmed to process such electronic signals into machine and human readable values, dynamically and automatically in real-time generate respective severity scores, prognosis scores, and a triage prioritization order, for each of the subjects, and display human readable values of such physiological signs, prognoses, and triage prioritization order, for medics, physicians, EMTs, or first responders, to use in treating the subjects in the order of the most urgent care needed to the least urgent care needed. The inventor has further determined that enhanced monitoring devices, systems and methods provided herein can significantly compress cycle time of medics, physicians, EMTs, or first responders', casualty monitoring, evaluation, decision-making, and treatment, to save lives.

The inventor has also determined that systems and methods provided herein can register and assign monitoring devices via RFID, QR Code, barcode, or similar identifications, with subjects, subject biometric information, and subject identifying information (e.g., photos, audio, video), in real-time and in battlefield, hospital-like, mass casualty events, emergency room waiting room, natural disaster (e.g., pandemic), roadside bomb, terrorist attack situations. The inventor has additionally determined that systems and methods provided herein can heuristically and predictively model the various subjects' physiological parameters and/or physiological signs with such subjects' medical histories to dynamically and automatically in real-time generate and update respective severity scores, prognosis scores, and triage prioritization orders, for more serious conditions, such as internal bleeding, hemorrhaging, stroke, that would otherwise be unavailable to such medics, physicians, EMTs, or first responders. The inventor has further determined that enhanced monitoring devices, systems and methods provided herein can provide such heuristically and predictively modeled data to the fingertips of such medics, physicians, EMTs, or first responders, in order to permit enhanced real-time decision-making. The inventor has also determined that enhanced monitoring devices, systems and methods provided herein can dynamically and automatically in real-time update such subjects' medical histories with physiological parameter and/or physiological sign data, location, severity scores, prognosis scores, and other information.

The inventor has further determined that enhanced monitoring devices, systems and methods provided herein can dynamically and automatically in real-time provide subjects' geolocation data, select monitoring groups, locate subjects, and significantly compress cycle time for triage, care instruction preparation, medical evacuation ("MEDEVAC") or casualty evacuation ("CASEVAC") procedures. The inventor has also determined that enhanced monitoring devices, systems and methods provided herein can permit real-time two-way communications and transfer of real-time data, such as physiological sign data, severity scores, prognosis scores, and triage prioritization order, between EMTs or first responders' and centralized physicians to change prognoses, send alerts or instructions, create MEDEVAC, CASEVAC, and post-injury reports, and modify ambulatory or hospital arrangements, such as which hospital the various subjects will be taken to. The inventor has also determined that enhanced monitoring devices, systems and methods provided herein performs continuous collection of medical data on various subjects, continuous correlations, and other data analyses, with such new data, and places such correlated, updated data at the fingertips of future medics, physicians, EMTs, or first responders in order to permit continuously enhanced real-time decision-making. The inventor has further determined that, for example, the enhanced monitoring devices, systems and methods described herein can provide continuous health monitoring for a wide variety of government agencies and industries (e.g., law enforcement agencies, military, intelligence agencies, hospitals, contract security, non-governmental organizations, electric power, oil and gas, industrial manufacturing, transportation, retail/consumer, security and facility protection) and automate efforts to significantly shorten cycle times between attack/accident/disaster/injury identification, prognosis, triage, and treatment.

The inventor has determined that the enhanced monitoring devices, systems and methods described herein may provide triage indication such as, for example, for single subject field triage, multiple subject field triage, single subject hospital triage, multiple subject hospital triage, and emergency response mass casualty monitoring (e.g., floods, disasters, terrorism, etc.). The inventor has determined that the enhanced monitoring devices, systems and methods described herein may provide remote, general monitoring indication such as, for example, for prolonged field care monitoring, prolonged patient monitoring, emergency room waiting room monitoring, nursing home/long-term care monitoring, chronic care monitoring, dementia patient monitoring and geolocation, suicide watch, drug rehab, mental health facilities/asylums, hospice care, and low-cost/third world operating room monitoring. The inventor has determined that the enhanced monitoring devices, systems and methods described herein may also provide, for example, telemedicine monitoring indication, sleep apnea monitoring indication (e.g., with monitoring devices usable as noninvasive devices to monitor subjects while sleeping), cardiac monitoring indication after heart surgery (which typically requires monitoring during all activities), burn victim monitoring indication, ambulatory monitoring indication (e.g., ambulance, MEDEVAC, helicopter, fixed wing aircraft (e.g., C-130), search and rescue, etc.), and pandemic/infectious disease/quarantine monitoring indication. The inventor has determined that the enhanced monitoring devices, systems and methods described herein may also provide pediatric monitoring indication such as, for example, for NICU infant monitoring, crib monitoring, daycare monitoring and geolocation, school nurse assistance, and youth sports.

The inventor has also determined that the enhanced monitoring devices, systems and methods described herein may provide remote, general wellness tracking/monitoring indication such as, for example, for cyclists/triathletes, quantified self-enthusiasts, biohackers, sports and performance monitoring (e.g., football players or pro drivers, etc.), in-home monitoring, remote monitoring, group geolocation monitoring, professional stress monitoring (e.g., pilots, truck drivers, etc.), chronic care monitoring, and health and fitness monitoring. The inventor has also determined that the enhanced monitoring devices, systems and methods described herein may provide monitoring for closed circuit fitness events such as, for example, CrossFit competitions, endurance races (e.g., triathlon, IronMan), general communal exercise events, etc. and provide subject location and health condition monitoring during such events. The inventor has also determined that the enhanced monitoring devices, systems and methods described herein may provide at-risk employee monitoring and indication such as, for example, for HAZMAT workers, truck drivers, pilots, divers, athletes (e.g., athlete monitoring to diagnose injuries (e.g., concussions and other blunt force traumas), etc. The inventor has further determined that the enhanced monitoring devices, systems and methods described herein may provide, for example, insurance physicals indication/monitoring, interrogations monitoring/field lie detection indication, charge/prisoner monitoring, sensitive skin monitoring. The inventor has further determined that the enhanced monitoring devices, systems and methods described herein may be useful in public health studies, research, search and rescue operations, disaster evacuation operations, pandemic operations, and in terrorism events.

Figure 4:
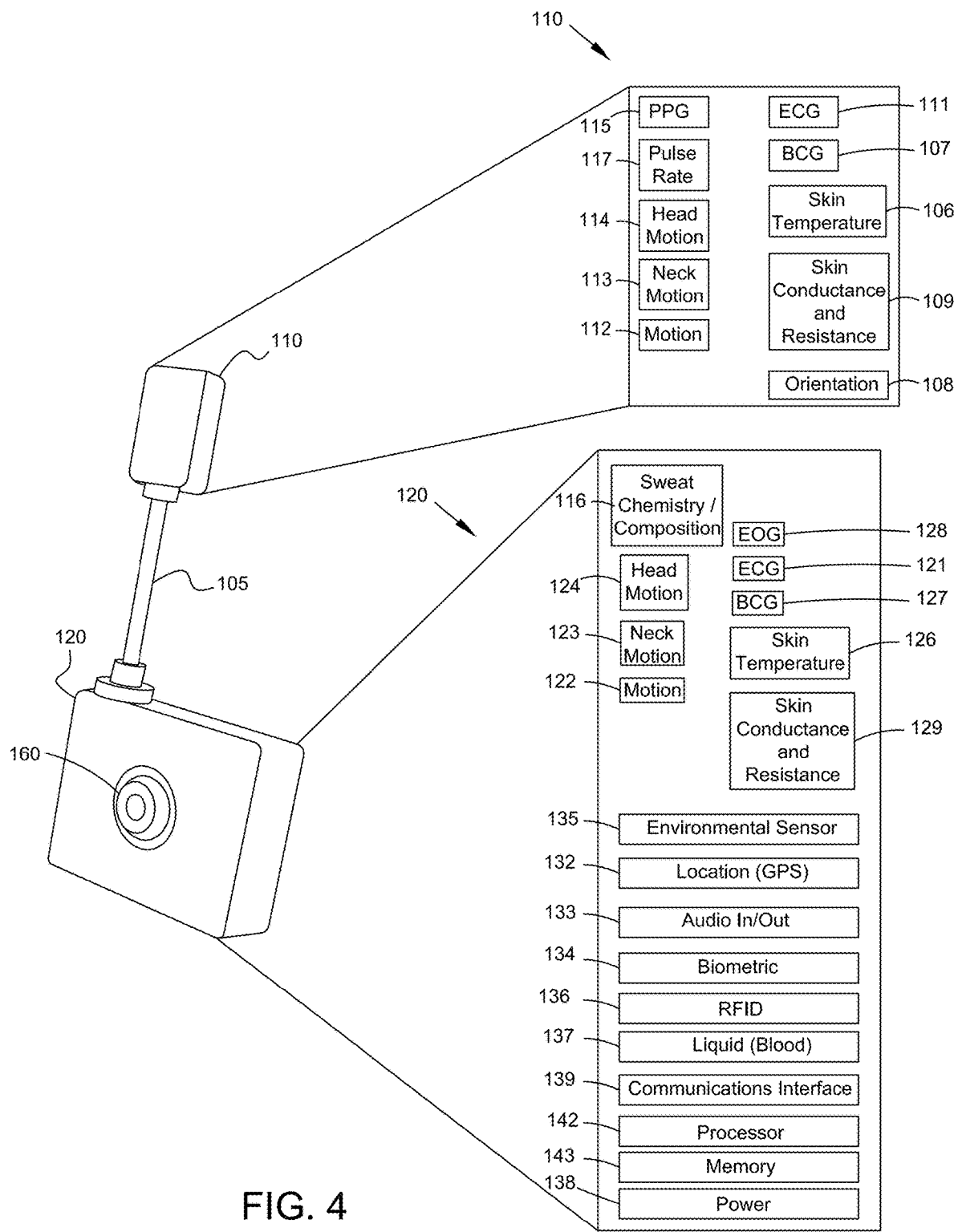
FIG. 4 is a block diagram of an example of an enhanced monitoring device in accordance with some embodiments of the present disclosure.

Referring to FIG. 4, a block diagram of an example of an enhanced monitoring device 140 in accordance with some embodiments of the present disclosure is provided. In various embodiments, enhanced monitoring device 140 is a context-aware, multi-physiological sign monitoring portion monitoring device. In various embodiments, for example as illustrated in FIG. 4, enhanced monitoring device 140 is a non-invasive, dual physiological sign monitoring portion monitoring device. In various embodiments, enhanced monitoring device 140 is dustproof, splash-proof, and/or configured to operate while submerged in water. In various embodiments, the circuitry of enhanced monitoring device 140 is coated in a Parylene or other polymer coating to keep it out of contact with outside air, dust, or moisture.

As shown in FIG. 4, enhanced monitoring device 140 may include a first physiological sign monitoring portion 110 and a second physiological sign monitoring portion 120 with an electromechanical interconnect 105 therebetween. In various embodiments, including embodiments described and illustrated in FIG. 14-15C, one or both of first physiological sign monitoring portion 110 and second physiological sign monitoring portion 120 of enhanced monitoring device 140 may be respectively configured to be deployed as a patch including a respective adhesive surface. Any suitable adhesive may be utilized to attach a surface of first physiological sign monitoring portion 110 of enhanced monitoring device 140 to a surface of a subject 100, and/or to attach a surface of second physiological sign monitoring portion 120 of enhanced monitoring device 140 to a different surface of the subject 100. In various embodiments, adhesive (not shown) is a biological adhesive that is conducive to the electrical signals of the sensors of each physiological sign monitoring portion (110, 120) of enhanced monitoring device 140, and configured to adhere to the different, respective surfaces of a subject 100 even in the presence of contaminates such as, for example, mud, blood, sweat, or water, at the site of their respective application. In various embodiments, adhesive (not shown) is configured to adhere to the different, respective surfaces of the subject in adverse conditions, but also be removed using a peeling force or a solvent. In various embodiments, each physiological sign monitoring portion (110, 120) of enhanced monitoring device 140 includes additional adhesive for reusability.

Figure 14:
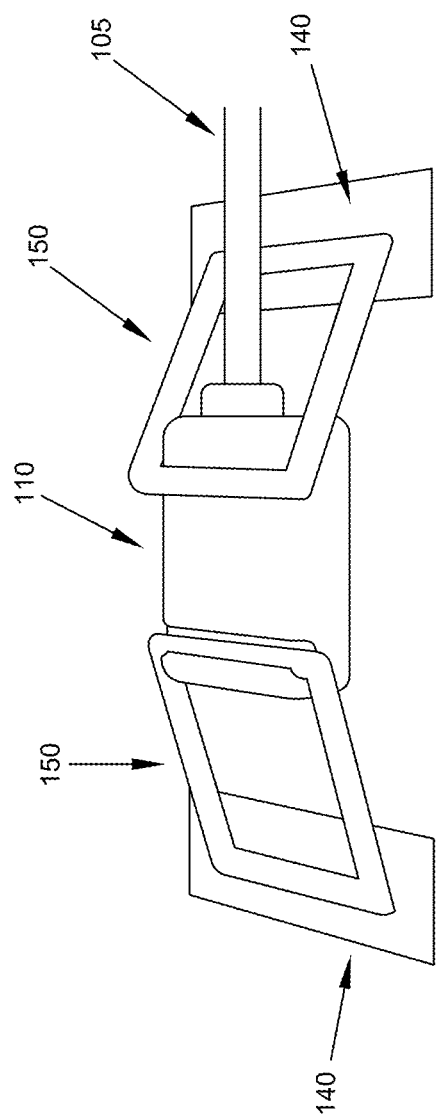
FIG. 14 is a perspective view illustrating an example of an anchoring mechanism for an example deployment of a physiological sign portion of an enhanced monitoring device according to some embodiments.
Figure 15B:
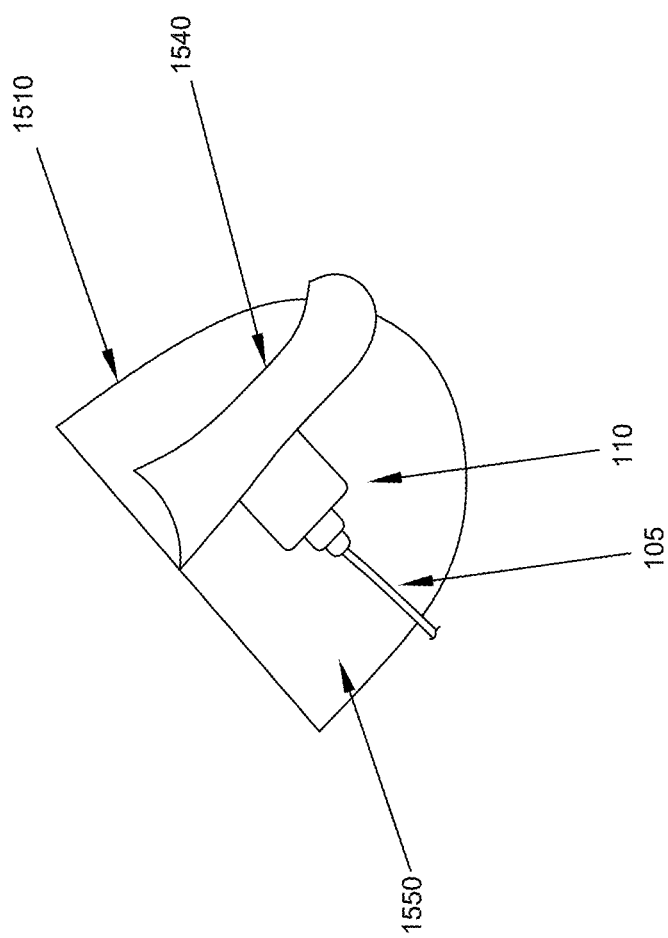
Figure 15C:
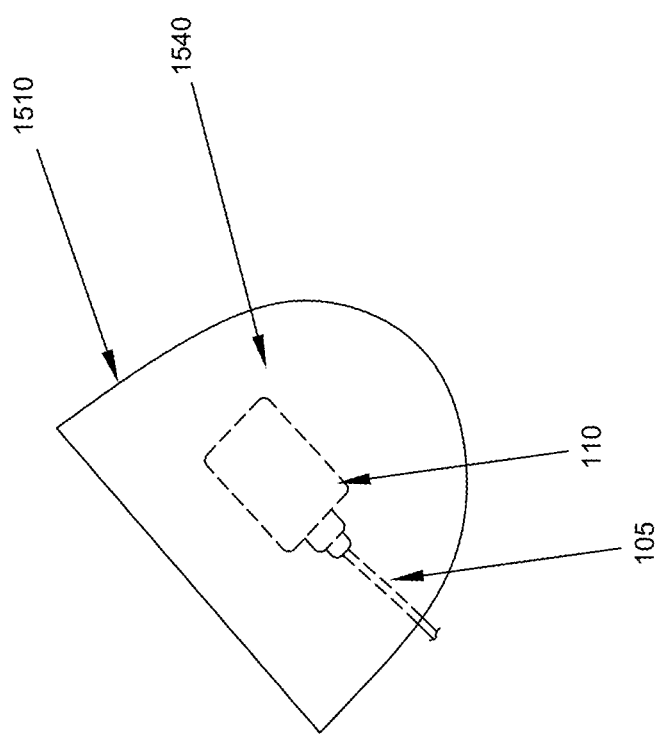

In various embodiments (e.g., as illustrated in FIGS. 15A-15C), one or more of the physiological sign monitoring portions (110, 120) of enhanced monitoring device 140 uses adhesive over the top of the respective sensors of the monitoring portion to maintain the plane of such respective sensors firmly pressed flat against the respective surface of the subject's skin. In various embodiments, one or more of the physiological sign monitoring portions (110, 120) of enhanced monitoring device 140 uses adhesive on the surfaces of the respective sensors of the monitoring portion to maintain the plane of such respective sensors firmly pressed flat against the respective surface of the subject's skin. In some embodiments, (e.g., as illustrated in FIG. 14), stretchable bands that loop around body parts of one or more of the physiological sign monitoring portions (110, 120) for support maintain the plane of such respective sensors firmly pressed flat against the respective surface of the subject's skin. In various embodiments, stretchable bands that adhere to adhesives may be used to maintain the plane of the respective sensors of one or more of the physiological sign monitoring portions (110, 120) of enhanced monitoring device 140 firmly pressed flat against the respective surface of the subject's skin.

In various embodiments (e.g., as illustrated in FIG. 4), first physiological sign monitoring portion 110 of enhanced monitoring device 140 is connected to second physiological sign monitoring portion 120 of enhanced monitoring device 140 via an electromechanical interconnect 105. In some embodiments, electromechanical interconnect 105 may comprise a variable length, ergonomic, flexible printed circuit and/or associated electronics, connectors, etc., configured to enable communication of electronic signals such as, for example, clock, physiological sensor data, orientation sensor data, motion sensor data, power data, and other data, between an electronic subsystem of first physiological sign monitoring portion 110, an electronic subsystem of second physiological sign monitoring portion 120, and/or external electronics. In some embodiments, electromechanical interconnect 105 may comprise, for example, a plurality of ergonomically designed flexible printed circuits, one or more wires in one or more pliable cable assemblies, optical fibers, one or more printed circuit boards, one or more combinations of flexible printed circuits, cable assemblies, connectors, and printed circuit boards, a part or all of a lanyard that can be worn about or around a neck or other body location of a subject 100. Electromechanical interconnect 105 may also comprise a unique identification value such as, for example, a predetermined resistor value, that is identifiable by an electronic subsystem of first physiological sign monitoring portion 110 and/or an electronic subsystem of second physiological sign monitoring portion 120. In some embodiments, electromechanical interconnect 105 includes quick release connectors to permit refurbishment and/or replacement of one of the physiological sign monitoring portions (e.g., 110) of enhanced monitoring device 140 while another one of the physiological sign monitoring portions (e.g., 120) remains in place.

In various embodiments, enhanced monitoring device 140 may acquire physiological parameters from a plurality of points (e.g., two points) on a subject 100, while allowing the subject 100 complete and unencumbered freedom of movement and/or allowing the subject 100 complete access to the electronics and clothing items that may be concurrently in use (e.g., worn by) the subject 100. Each physiological sign monitoring portion (110, 120) of enhanced monitoring device 140 may be configured for deployment on a different, respective surface of a subject 100.

The inventor has identified vital sign acquisition points on a subject 100 that have high blood perfusion, access to blood flow as it exits thermal core of the body (specifically the cranium), access to cardiac electrical signals with freedom from natural electrical interference from the body's electromyographic signals (EMGs) and common mode interference, access to a pivot point that moves when blood flows, access to a pivot point that moves when a subject breathes or coughs, proximity to skeletal, venous, and nerve tissues, the correct density of sweat glands, and low frequencies of skin conditions, scars, hair, or tattoos. These particular vital sign acquisition points for a subject 100 are at surfaces on the back of a respective ear (e.g., opposite a concha) of the subject (e.g., surface 104, FIG. 2A), surfaces over a mastoid region of the neck of the subject, and surfaces over another region of the neck of the subject (e.g., at the "Sempulse Points" described below). The subject physiological parameters that may be monitored at these particular vital sign acquisition points include, but are not limited to, photoplethysmogram (PPG) waveforms, electrocardiogram (ECG) waveforms, ballistocardiogram (BCG) waveforms, skin temperature (including skin temperature at the point of cranial blood ejection), skin conductance, skin resistance (e.g., skin resistivity), head motion relative to a motion axis, neck motion relative to a motion axis, general motion relative to a motion axis, sweat chemistry, sweat composition, head orientation relative to an orientation axis, and neck orientation relative to an orientation axis. In various embodiments, environmental parameters may also be monitored at one or more of these vital sign acquisition points and may include, but are not limited to, ambient temperature, ambient pressure, humidity, altitude, UV index, ambient light, or combinations thereof.

FIGS. 1A and 1B are side and rear perspective view of a head and neck of a subject 100 and illustrate an example of a deployment of an example of an enhanced monitoring device 140 in accordance with some embodiments of the present disclosure. As shown in FIGS. 1A and 1B, a first physiological sign monitoring portion 110 of enhanced monitoring device 140 may be configured to be deployed on a surface on the back of a respective ear, and in particular, opposite a concha (e.g., a cavum concha), of a subject 100 (e.g., surface 104, FIG. 2A), and a second physiological sign monitoring portion 120 of enhanced monitoring device 140 may be configured to be deployed on a surface over a region of the neck of the subject 100 (e.g., surface in USP, LSP1, or LSP2, FIGS. 2A-2C), for sensing one or more physiological parameters of such subject 100. The deep, capacious cavity of the ear is called the concha, and is bisected by the crus helix into an upper part called the cymba concha and a lower part called the cavum concha. The cavum concha is the deepest recess of the ear, just in front of the ear canal Immediately behind the concha on the back of the ear is the back of the concha. The inventor has determined that deploying physiological sensors of one physiological sign monitoring portion (e.g., 110) of the enhanced monitoring device 140 on a surface on the back of a respective ear, and in particular, opposite a concha (e.g., opposite a cavum concha), of a subject 100 provides a surface that has high blood perfusion, in that the tissue beneath the external skin surface of this portion of the ear has a high concentration of capillary beds, and that has limited or predictable motion, even during emergency situations. The inventor has observed that the back of the ear, and the back of the concha in particular, is an area of high blood perfusion with direct access to blood flow exiting the cranium. There are limited muscles in the ear, so EMG artifacts are extremely limited. The ear and neck are connected via a hinge by means of the neck bones, so the ear acts as a pivot point away from the neck to determine blood flow from ballistocardiography (BCG). The concha, and in particular the cavum concha, is micrometers away from the posterior auricular artery, providing access to thin-skinned blood analysis, blood temperature sampling, and a major conductor of cardiac signals. The back of the ear has very low sweat gland density and has low frequencies of skin conditions, scars, hair, or tattoos and its thin skin is very resilient to different skin tones.

In various embodiments, at least one physiological sensor in each physiological sign monitoring portion (110, 120) of the enhanced monitoring device 140 is configured to generate a respective electronic signal based on the same monitored physiological parameter of the subject. The inventor has determined that various physiological parameters require at least two (2) points from which to more reliably measure and analyze the signals therebetween. Such physiological parameters include electrocardiogram (ECG) waveforms, ballistocardiogram (BCG) waveforms, skin temperature, skin conductance, skin resistance (e.g., skin resistivity), and head motion relative to a motion axis. The inventor has also determined that adding additional points produces similar results, but adds minimal to no measurable benefit beyond the first two (2) points. The inventor has further determined that deploying one physiological sign monitoring portion (110) of the enhanced monitoring device 140 on a surface on the back of the ear (e.g., opposite a concha) of a subject 100 and another physiological sign monitoring portion (120) in close proximity (e.g., another surface on the back of the ear) is theoretically possible, but it is practically infeasible under most circumstances. The inventor determined and obtained, during experimentation and testing, optimized electrical signal readings when the two physiological parameter measurement points (e.g., two different, respective surfaces of the subject for respective deployment of first and second physiological sign monitoring portions (110, 120) of the enhanced monitoring device 140) were at least three (3) inches apart from each other.

In various embodiments, a first physiological sign monitoring portion 110 of the enhanced monitoring device 140 may be configured for deployment on a surface on the back of an ear (e.g., opposite a concha) of a subject 100, and a second physiological sign monitoring portion 120 of the enhanced monitoring device 140 may be configured for deployment on a surface over a region of the neck of the subject. The inventor has determined and identified three "Sempulse Points" on the surface of the neck which are three (3) points over top of the pockets formed between the folds of the trapezius muscle, the sternocleidomastoid (SCM) muscle, and the scalene muscles.

Figure 2C:
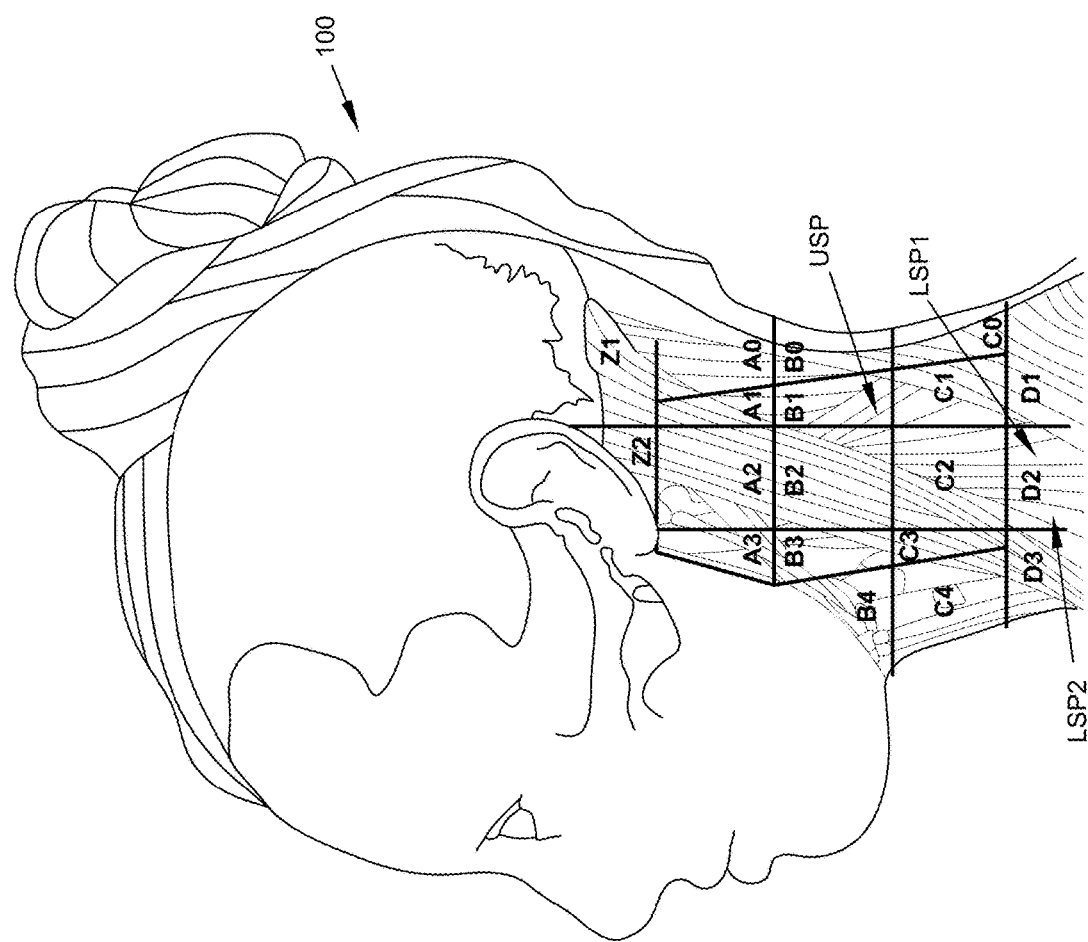

Referring now to FIGS. 2A-2C, respective side perspective views of a head and neck of a subject 100 and illustrating an example of surfaces for example deployments of an enhanced monitoring device 140 according to some embodiments is provided. As shown in FIG. 2A, in some embodiments, the different, respective surfaces for deployment of two physiological sign monitoring portions (e.g., 110, 120) of enhanced monitoring device 140 may be a surface 104 on the back of a respective ear (e.g., opposite a concha) of a subject 100, and an "Upper Sempulse Point" (USP) surface over a region of the neck of the subject 100. As used herein, the "Upper Sempulse Point" (USP) is the intersection of a line parallel to the ground that touches the bottom of the jawbone of a subject 100 and a perpendicular line approximately 1.5 inches behind the ear canal of the subject 100, and is roughly in-line with the plane corresponding to the back of the earlobe of the subject 100. The inventor has determined that this "Upper Sempulse Point" site may be ideal for deployment of a physiological sign monitoring portion (e.g., 120) of an enhanced monitoring device 140 because it is over top of the pocket formed between the folds of the trapezius muscle and sternocleidomastoid (SCM) muscle under the levator scapulae of a subject 100.

Referring now to FIG. 2B, a side perspective view of a head and neck of a subject 100 and illustrating an example of surfaces for example deployments of an enhanced monitoring device 140 according to some embodiments is provided. As shown in FIG. 2B, the three "Sempulse Points" on the surface of the neck of a subject 100 are illustrated as USP (as described above with reference to FIG. 2A), LSP1, and LSP2. As used herein, the "Lower Sempulse Points" (LSP1, LSP2) are directly below the ear canal and approximately 1.5 inches behind the ear canal and above the trapezius muscle at the base of the neck of the subject 100. As illustrated in FIG. 2B, the inventor has identified and described two (2) "Lower Sempulse Points" as a point over the pocket in-between the posterior and middle scalene muscles, above the trapezius muscle, of a subject 100 (Lower Sempulse Point 1 or LSP1), and a point over the pocket in-between the middle and anterior scalene muscles, above the trapezius muscle, of a subject 100 (Lower Sempulse Point 2 or LSP2).

The inventor has determined and identified the three "Sempulse Points" as ideal for deployment of a physiological sign monitoring portion (e.g., 120) of an enhanced monitoring device 140 because of the relative lack of electromyographic (EMG) signal artifacts in these locations as they are immediately devoid of muscle fibers. The inventor determined, during experimentation and testing, a noise floor in these locations below 1 μVpp in a 4-16 Hz band. In addition, the inventor has determined that, based on experimental and clinical results, neck placement precision is not required in these locations as minute position changes were not determined to introduce significant changes in signal quality or voltage.

The inventor has determined and identified that the three "Sempulse Points" provide similar features and relationships to underlying body tissues of a subject. However, based on experimental and clinical results, the inventor has determined that the height of the subject 100, and a corresponding linear distance between the concha and the "Upper Sempulse Point" (USP), plays a role in selecting the respective surfaces for deployment of each of the plurality of physiological sign monitoring portions (e.g., 110, 120) of enhanced monitoring device 140. Based on experimental and clinical results, the inventor has determined that if the distance between the cavum concha and the "Upper Sempulse Point" is less than approximately 3.5 inches, then the physiological parameter measurements taken by the physiological sign monitoring portion (e.g., 120) at the "Upper Sempulse Point" will produce a higher signal-to-noise ratio (SNR) due to the lack of signal propagation. Based on experimental and clinical results, the inventor has also determined that this signal-to-noise ratio (SNR) phenomenon is directly correlated to height of subject 100. Based on experimental and clinical results, the inventor has determined that subjects taller than five feet five inches to five feet eight inches (5'5"-5'8") can use either a surface at the "Upper Sempulse Point" (USP), or a surface at either of the "Lower Sempulse Points" (LSP1 or LSP2), as the deployment location of one of the physiological sign monitoring portions (e.g., 120), with negligible deleterious effects. However, based on experimental and clinical results, the inventor has also determined that subjects shorter than five feet five inches to five feet eight inches (5'5"-5'8"), and with less than 3.5 inches of linear distance between their cavum concha and their respective "Upper Sempulse Point", should use one of the "Lower Sempulse Points" (LSP1 or LSP2) to avoid the observed higher signal-to-noise ratio (SNR) phenomenon described above.

The inventor has determined and identified that the "Sempulse Points" of the neck sit respectively on major arteries (e.g., ascending pharyngeal artery, carotid artery), veins (e.g., interior jugular vein, exterior jugular vein), nerve bundles (e.g., great auricular nerves), and also are areas of the neck of a subject which exhibit high blood perfusion. The inventor has observed that arteries, veins, and nerve bundles are all excellent conductors of the cardiac signals, and that blood from the neck moves in such volumes and travels from the chest that it is near the temperature of the body's thermal core. The inventor has also observed that the neck has a high number of arteries, bones, and connective tissues since it is the only conduit to the brain, but it has a relatively low percentage volume of muscle tissue so it has relatively low levels of EMG artifacts. The ear and neck are connected via a hinge by means of the neck bones, so the neck acts as a pivot point to signal blood flow due to ballistocardiography (BCG). The inventor has observed that the fact that the head of a subject (e.g., 100) generally (and imperceptibly) moves to the left every time the subject's heart beats due to the increased blood in the carotid arteries on the right side of the subject's neck. The inventor has also observed that, as the neck houses the windpipe, it is a natural site to monitor subject breathing, coughing, and sneezing motions. The inventor has further observed that the neck has a relatively low sweat gland density and has low frequencies of skin conditions, scars, hair, and tattoos, and that the proximity of blood to the surface is very resilient to different skin tones.

Figure 16:
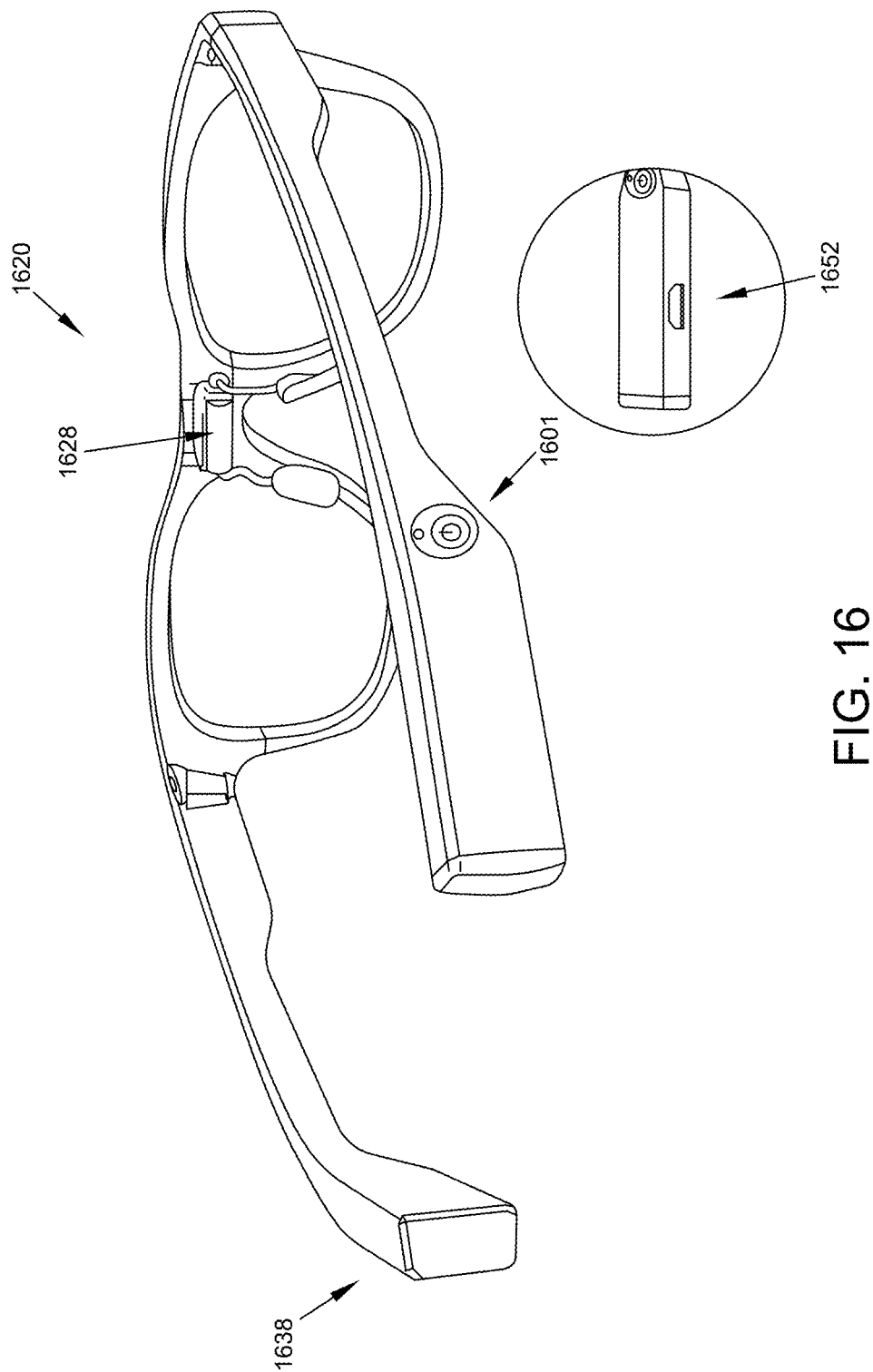
FIG. 16 is a perspective view of an example of a physiological sign portion of an enhanced monitoring device according to some embodiments of the present disclosure.

In various embodiments, a first physiological sign monitoring portion 110 of enhanced monitoring device 140 may be configured for deployment on a surface 105 on the back of a respective ear (e.g., opposite a concha) of a subject 100, and a second physiological sign monitoring portion 120 of enhanced monitoring device 140 may be configured for deployment on one of: a surface of the neck over the pocket formed between the trapezius and the sternocleidomastoid muscles of the subject and under the levator scapulae of the subject 100 (i.e., USP), a surface of the neck over the pocket formed between the posterior scalene and the middle scalene muscles of the subject, and above the trapezius muscle of the subject 100 (i.e., LSP1), a surface of the neck over the pocket formed between the middle scalene and the anterior scalene muscles of the subject, and above the trapezius muscle of the subject 100 (i.e., LSP2), or a skull, nose, or face surface of the subject 100 opposite a portion of an eyeglasses physiological sign monitoring portion 1620 (e.g., FIG. 16). In various embodiments, the different, respective surfaces (e.g., surface 105 and surface at USP, LSP1, LSP2, or skull, nose, or face surface opposite a portion of eyeglasses physiological sign monitoring portion 1620) of the subject 100 are at least three inches apart from each other.

In various embodiments (e.g., a surface on the back of a respective ear of a subject 100 is not available), a first physiological sign monitoring portion 110 of enhanced monitoring device 140 may be configured to be deployed on a surface over a mastoid region of the neck of a subject 100 (or a surface at the top center of the neck of a subject 100), and a second physiological sign monitoring portion 120 of enhanced monitoring device 140 may be configured to be deployed on a surface over a region of the neck of the subject 100 (e.g., USP, LSP1, LSP2), or a skull, nose, or face surface of the subject 100 opposite a portion of an eyeglasses physiological sign monitoring portion 1620 (e.g., FIG. 16), for sensing one or more physiological parameters. In various embodiments, the mastoid region of the neck of a subject is the region behind an ear of the subject, and under the natural hair line of the subject, but above a line parallel to the ground and touching the edge of the earlobe closest to the shoulder of the subject. The inventor has determined that deploying physiological sensors of a physiological sign monitoring portion (110, 120) of enhanced monitoring device 140 on a surface over a mastoid region of the neck of the subject 100 also provides many benefits similar to a surface on the back of a respective ear (e.g., in particular opposite a concha) of the subject 100 (e.g., high blood perfusion, accessibility without clothing interference, non-invasive while a subject is in motion or at rest, limited hair, and readily available access to the arteries for blood composition analyses, etc.), and may be particularly useful in instances where such a surface on the back of a respective ear (e.g., in particular opposite a concha) of the subject 100 is compromised (e.g., due to injury, illness, skin issues, burns, etc.). Relative to a surface on the back of a respective ear (e.g., in particular opposite a concha) of a subject 100, the inventor has determined that the surface over a mastoid region is further from the ear where blood exits the body's thermal core and has a higher density of sweat glands and hair follicles. Moreover, the inventor has observed that there is a higher likelihood of interference with clothing, headgear, helmets, etc. at a surface over a mastoid region of a subject 100. The inventor has determined that deploying a physiological sign monitoring portion (e.g., 110) on a surface at the top center of the neck just under the earlobe of the subject 100 (e.g., USP) has a benefit over a surface on the back of an ear (e.g., opposite a concha) of the subject 100, namely that it is not prone to pinch injuries, e.g., on fall events where the earlobe of a subject 100 is pushed backward toward the skull of the subject 100. Where first physiological sign monitoring portion 110 of enhanced monitoring device 140 is deployed on a surface over a mastoid region of the neck of a subject 100 (or, for example, on a surface over a top center of the neck of a subject 100 (e.g., USP)), and not on a surface on the back of an ear (e.g., opposite a concha) of the subject 100, a suitable data transformation may be necessary to calibrate the data received at a mobile communication and display device (e.g., 800).

The inventor has determined that PPG waveforms may be optimally acquired from a surface on the back of an ear (e.g., opposite a concha), a surface over the mastoid region, and a surface over the top center of the neck directly under the earlobe (e.g., USP). The inventor has also determined that ECG waveforms may be optimally acquired from only a limited number of sites on the body of a subject, and has observed that very few sites can be read from only three inches apart. As such, the inventor has determined and identified that the surface on the back of an ear (e.g., opposite a concha), surface over a mastoid region, surface over another region of the neck (e.g., USP), are optimal locations for deployment of the plurality of sign monitoring portions (e.g., 110, 120) with ECG sensors of enhanced monitoring device 140 due to the high volume of electrical signals between the heart and the brain of a subject. As discussed below, the inventor has also determined that skull or nose surfaces opposite an arm or nosepad portions of an eyeglasses physiological monitoring portion 1620 may be ideal locations for deployment of ECG sensors. The inventor has further determined that skin temperature measurements from these respective surfaces of the subject are optimized because these sites provide both blood from an ejection site of the body's thermal core and an ejection site of blood from the cranium, which can provide cranial temperature as well as core body temperature. The inventor has determined that these sets of points also capture pivoting motions of the head and neck, as well as the general motions of the body. Moreover, the inventor has determined that utilizing a point on the neck of a subject (e.g., USP, LSP1, LSP2) is advantageous for sweat chemistry and sweat composition measurements, since the neck's sweat gland density is higher than that of the back of the ear and mastoid region, without producing such a high-level of sweat to impede sensing or causing pressure-sensitive adhesives to dissipate or fail prematurely. Furthermore, the inventor has determined that these specific locations are also optimal because they represent body placements where physiological sign monitoring may occur without interference to a subject's normal range of motion or interference to clothing, or interference with activities that a subject may participate in. In addition, the inventor has determined that these specific locations are also optimal for physiological sign monitoring as they permit acquisition of electrical signals via the skin without the need for a right-leg drive or any kind of bias or common mode removal.

Voltage increases on the side of the neck of a subject, from front to back, and also increases as the vector's length increases. The inventor has observed that noise and motion artifacts, from general body movements, increase relative to neck surfaces moving rearward across the neck from front-to-back, and as a result of the trapezius muscle. The inventor has observed that EMG signals from muscle groups pose challenges; bisecting any muscle fibers introduces additional noise. The inventor has also observed that the rear of the neck, in general, presents larger body motion challenges while the front of the neck presents jaw-related motion challenges. The inventor further observed that moving a subject's jaw in extreme positions presents problems with ECG signal acquisition, especially with electrodes frontward on the side of the neck. The inventor also observed that turning a subject's head to extreme positions presents problems with ECG signal acquisition, especially with electrodes rearward on the side of the neck. The inventor also observed that raising the arms of a subject to extremes, and the associated jitter from stressing the subject's range of motion, also presents problems with ECG acquisition.

Based on experimental and clinical results, the inventor determined that diagonal placement of a physiological sign monitoring portion (110, 120) of enhanced monitoring device 140 on the respective neck of subjects at the top center immediately under the ear lobe (e.g., USP) produced the highest signal quality of the neck: neck electrode scenarios with the lower point as far away as possible while still resting towards the rear of the side of the neck but in front of the trapezius muscle.

The inventor observed that, due to the features of thermoregulation, the human body limits blood flow to the extremities during any kind of stress, injury, trauma, or extreme conditions. As such, the inventor determined that this fact, combined with high rates of motion in the extremities, makes the arms, wrists, hands, legs, and feet of a subject poor choices for non-invasive physiological sign monitoring. The inventor also eliminated the chest, core, stomach, back, and buttocks of a subject from non-invasive physiological sign monitoring contention due to clothing, hair, sweat, sitting, laying, sleeping, and the motions of everyday activities. Based on experimental and clinical results, the inventor determined that the front and back of the neck of a subject interfere with breathing, sleeping, and laying while also posing serious sensor acquisition problems with large EMG signals involved with swallowing, breathing, and talking from the front of the neck and the large mass of electrical signals passing through the spine. The inventor also observed that certain surfaces on the face of a subject, as well as surfaces on the top of the head, its sides, the crown, and the nape of a subject, are not practical for non-invasive physiological sign monitoring from the standpoint of noticeability, irritation, sensitivity, sweating, hair, eyewear, eating, and sleeping. The inventor also observed that surfaces in the ear canal, and on the front of the ear, cannot be used in a non-invasive manner due to hearing and ear protection restrictions. The inventor thus determined that the back of the ear of a subject, the sides of the neck of the subject, and skull, nose, or face surfaces of the subject 100 opposite a portion of an eyeglasses physiological sign monitoring portion 1620 (e.g., FIG. 16) are the multi-point sites on the body of the subject that meet the qualifications for the successful acquisition of physiological parameters and of being truly non-invasive to the subject.

Referring now to FIG. 2C, a side perspective views of a head and neck of a subject and illustrating examples of surfaces for example deployments of an enhanced monitoring device according to some embodiments is provided. In particular, FIG. 2C illustrates a mapping of surfaces of a neck of a subject that the inventor has determined provide optimal electrical signal acquisition via the skin. Based on experimental and clinical results, the inventor determined that, relative to each other, zones A2, A3, B2, C2, D2, and neck surfaces directly behind the ear lobe in Z2, had good electrical signal acquisition quality. The inventor also determined that, relative to each other, the good electrical signal acquisition quality gradually deteriorated along surfaces of the neck moving away from directly behind the ear lobe within zone Z2, and moving away from the center of the neck from zones Z2 to Z1, from A2 to A1, from B2 to B1 and to B3, from C2 to C1 and to C3, and from D2 to D1 and to D3. The inventor further determined that, relative to each other, zones B4, C4, A0, B0 and C0 had poor electrical signal acquisition quality. As illustrated in FIG. 2C, the "Upper Sempulse Point" (USP) sits at the intersection of zones B1, B2, C1, and C2. In various embodiments, USP placement of the center of the physiological sign monitoring portion (110, 120) of enhanced monitoring device 140 may deviate up to one centimeter (1 cm) into any of zones B1, B2, C1, and C2. As illustrated in FIG. 2C, the "Lower Sempulse Points" (LSP1, LSP2) fall in the D2 zone.

In various embodiments, a first physiological sign monitoring portion 110 of enhanced monitoring device 140 may be configured for deployment on a surface of the back of a respective ear (e.g., opposite a concha) of a subject 100, or over a mastoid region of the neck of the subject 100, and a second physiological sign monitoring portion 120 of enhanced monitoring device 140 may be configured for deployment on a surface of the neck over the pocket formed between the trapezius and the sternocleidomastoid muscles of the subject and under the levator scapulae of the subject 100. In some embodiments, a first physiological sign monitoring portion 110 of enhanced monitoring device 140 may be configured for deployment on a surface of the back of a respective ear (e.g., opposite a concha) of a subject 100, or over a mastoid region of the neck of the subject 100, and a second physiological sign monitoring portion 120 of enhanced monitoring device 140 may be configured for deployment on a surface of the neck over the pocket formed between the posterior scalene and the middle scalene muscles of the subject 100, and above the trapezius muscle of the subject 100, or on a surface of the neck over the pocket formed between the middle scalene and the anterior scalene muscles of the subject, and above the trapezius muscle of the subject 100, or on a skull, nose, or face surface of the subject 100 opposite a portion of an eyeglasses physiological sign monitoring portion 1620 (e.g., FIG. 16). In some embodiments, a first physiological sign monitoring portion 110 of enhanced monitoring device 140 may be configured for deployment on a surface of the neck over the pocket formed between the trapezius and the sternocleidomastoid muscles of the subject 100 and under the levator scapulae of the subject 100, and a second physiological sign monitoring portion 120 of enhanced monitoring device 140 may be configured for deployment on a surface of the neck over the pocket formed between the posterior scalene and the middle scalene muscles of the subject 100, and above the trapezius muscle of the subject 100, or on a surface of the neck over the pocket formed between the middle scalene and the anterior scalene muscles of the subject 100, and above the trapezius muscle of the subject 100, or on a skull, nose, or face surface of the subject 100 opposite a portion of an eyeglasses physiological sign monitoring portion 1620 (e.g., FIG. 16).

In various embodiments, the physiological sign portions (110, 120) of enhanced monitoring device 140 each include a single sensor side in that vital or physiological signs of a subject 100 are only respectively monitored on a single side towards a respective surface of the subject. In various embodiments, each physiological sign portion (110, 120) of enhanced monitoring device 140 includes a respective collection of physiological sensors. In various embodiments, one or more physiological sensors are included in a first physiological sign portion 110 of enhanced monitoring device 140, and one or more physiological sensors are included in a second physiological sign portion 120 of enhanced monitoring device 140. In various embodiments, the sensors are non-invasive. In various embodiments, enhanced monitoring device 140 is a low-cost, disposable device. The inventor has determined that an enhanced monitoring device described herein may be bio-contaminated in a pre-hospital or triage environment (e.g., a trauma, battlefield, terrorist attack, emergency room, or natural disaster, environment where mud, blood, sweat, water, and other contaminates are prevalent) and replaced at a low cost. For example, one or more physiological sign portions (e.g., 110) of enhanced monitoring device 140 may be a disposable portion including one or more physiological sensors, and another one or more physiological sign portions (e.g., 120) of enhanced monitoring device 140 may be a reusable, finitely-reusable, or refurbishable, portion including one or more physiological sensors. By way of another example, each of the physiological sign portions (e.g., 110, 120) of enhanced monitoring device 140 may be disposable units. In various embodiments, an electronic subsystem of each physiological sign portion (110, 120) may include a respective unique identification value such as, for example, a predetermined resistor value, that is identifiable by an electronic subsystem of electromechanical interconnect 105 and/or an electronic subsystem of other portions of enhanced monitoring device 140 (e.g., of another physiological sign portion (120, 110), another portion (not shown)).

In various embodiments, and as illustrated in the example in FIG. 4, an electronic subsystem of first physiological sign portion 110 of enhanced monitoring device 140 may include one or more of a photoplethysmogram (PPG) sensor 115, an electrocardiogram (ECG) sensor 111, a pulse rate sensor 117, a ballistocardiogram (BCG) sensor 107, a head motion sensor 114, a neck motion sensor 113, a general motion sensor 112, a skin temperature sensor 106, a skin conductance (and/or skin resistivity) sensor 109, and an orientation sensor 108. In various embodiments, and as illustrated in the example in FIG. 4, an electronic subsystem of second physiological sign portion 120 of enhanced monitoring device 140 may include one or more of an electrocardiogram (ECG) sensor 121, a ballistocardiogram (BCG) sensor 127, an electrooculogram sensor 128, a head motion sensor 124, a neck motion sensor 123, a general motion sensor 122, a skin temperature sensor 126, a sweat chemistry (and/or sweat composition) sensor 116, and a skin conductance (and/or skin resistivity) sensor 129. In various embodiments, electrocardiogram (ECG) sensor 111 and/or electrocardiogram (ECG) sensor 121 includes an electrical potential sensor. In various embodiments, head motion sensor (114, 124), neck motion sensor (113, 123), and/or general motion sensor (112, 122) may include a multi-axis (e.g., 3-axis) accelerometer. In various embodiments, motion sensor 112 and/or motion sensor 122 may be configured to generate different electronic signals for neck motion, head motion, and/or general motion of subject 100. In some embodiments, an electronic subsystem of first physiological sign portion 110 and/or second physiological sign portion 120 may include an electroencephalography (EEG) sensor configured to monitor a subject's brain activity, an electromyography (EMG) sensor. In some embodiments, an electronic subsystem of second physiological sign portion 120 may include a blood loss sensor 137 configured to generate an electronic signal based on a respectively monitored amount of blood and that may be calibrated to determine the corresponding amount of blood that has been lost from the subject's circulatory system. In various embodiments, an electronic subsystem of first physiological sign portion 110, and/or second physiological sign portion 120, of enhanced monitoring device 140 may include one or more environmental sensors 125, such as, for example, an ambient temperature sensor, an ambient pressure sensor, a humidity sensor, an altitude sensor (altimeter), a UV index sensor, an ambient light sensor, or combinations thereof. Any suitable environmental sensor may be included as the one or more environmental sensors 125.

The inventor has determined that enhanced monitoring devices, systems, and methods described herein provide values indicative of a plurality of physiological signs of a subject 100 using electronic signals generated by physiological sensors included in one or more of the plurality of the physiological sign portions (e.g., 110, 120) of an enhanced monitoring device (e.g., 140). For example, values indicative of blood oxygen saturation (i.e. pulse oximetry (SpO$_2$)) may be determined from PPG waveform data (e.g., in electronic signals generated by PPG sensor 115 in first physiological sign portion 110), and as further detailed below. Values indicative of end tidal CO$_2$ may be determined from such SpO$_2$ values and such PPG waveform data, and as further detailed below. Values indicative of heart rate (HR) may be determined from such PPG waveform data and/or measured directly with physical blood pulses, and as further detailed below. Values indicative of coughing and/or sneezing may be determined from such PPG waveform data and neck motion data (e.g., in electronic signals generated by neck motion sensor 113 in first physiological sign portion 110 and/or by neck motion sensor 123 in second physiological sign portion 120), and as further detailed below.

Values indicative of electrocardiogram (ECG) pulse rate, of premature ventricular complexes, of R-R interval, and/or of heart rate variability (HRV) may be respectively determined from ECG waveform data (e.g., in electronic signals generated by ECG sensor 111 in first physiological sign portion 110 and/or by ECG sensor 121 in second physiological sign portion 120), and as further detailed below. Values indicative of pulse deficit may be determined from such heart rate data and such ECG pulse rate data, and as further detailed below. Values indicative of pulse transit time (PTT) may be determined from calculations to determine the amount of time blood takes to traverse a known distance using ECG R-peaks as the starting timeframe and such PPG waveform data, ballistocardiogram waveform data (e.g., in electronic signals generated by BCG sensor 107 in first physiological sign portion 110, by BCG sensor 127 in second physiological sign portion 120, by head motion sensor 114 in first physiological sign portion 110, and/or by head motion sensor 124 in second physiological sign portion 120), and physical blood pulses as the ending time point, and as further detailed below. Values indicative of arterial characteristics may be determined from such PPG waveform data, such ECG waveform data, arterial elasticity/stiffness data, and the physical motions of the skin that measure the blood's force waves present in the circulatory system and the ski (e.g. the forces of the heart systole (pulse wave) that propagate through the veins and arteries and get transferred to the skin), and as further detailed below. Values indicative of cuffless blood pressure (e.g., mean arterial pressure, systolic/diastolic pressures) may be determined from such pulse transit time data, such PPG waveform data, such arterial characteristics data, the subject's physical characteristics (e.g., height, weight, health metrics, etc.) and biometrics, personal correlation data, and population correlation data, and as further detailed below. Values indicative of pulse wave velocity (PWV) may be determined from such pulse transit time data, such arterial characteristics data, the subject's physical characteristics and biometrics, and population correlation data, and as further detailed below.

Values indicative of respiratory rate may be determined from such ECG waveform data and such PPG waveform data and/or measured directly with physical respiration motion data observed from the neck (e.g., in electronic signals generated by neck motion sensor 113 in first physiological sign portion 110 and/or by neck motion sensor 123 in second physiological sign portion 120), and as further detailed below. Values indicative of subject (e.g., subject 100) activity levels may be determined from such ECG waveform data, such respiratory rate data, and general motion data (e.g., in electronic signals generated by motion sensor 112 in first physiological sign portion 110 and/or by motion sensor 122 in second physiological sign portion 120), and as further detailed below. Values indicative of maximal oxygen uptake ($VO_2$ Max) may be determined from such heart rate data, such respiratory rate data, such physical respiration motion data, such subject activity level data, the subject's physical characteristics and biometrics, and population correlation data, and as further detailed below. Values indicative of core body temperature may be determined from such subject activity level data, skin temperature data (e.g., in electronic signals generated by skin temperature sensor 106 in first physiological sign portion 110 and/or by skin temperature sensor 126 in second physiological sign portion 120), and ambient weather data (e.g., in electronic signals generated by an environmental sensor 135 in second physiological sign portion 120), and as further detailed below. Values indicative of cranial temperature may be determined from such core body temperature data, and/or from such subject activity level data, such skin temperature data, and such ambient weather data, and as further detailed below.

Values indicative of galvanic skin response (GSR), and values indicative of bioimpedance (BioZ), may be respectively determined from skin resistivity/skin conductivity data (e.g., in electronic signals generated by a skin conductance and resistance sensor 109 in first physiological sign portion 110 and/or by a skin conductance and resistance sensor 129 in second physiological sign portion 120), and as further detailed below. Values indicative of glucose levels may be determined from sweat chemistry/sweat composition data (e.g., in electronic signals generated by a sweat chemistry/sweat composition sensor 116 in second physiological sign portion 120), and as further detailed below. Values indicative of hydration may be determined from such sweat chemistry/composition data and such skin resistivity/skin conductivity data, and as further detailed below. Values indicative of stress may be determined from such ECG data, such heart rate variability (HRV) data, such arterial characteristics from PPG data, such subject activity level data, such respiratory rate data, such physical respiration motion data, such sweat chemistry/composition data and/or such skin resistivity/skin conductivity data, and as further detailed below.

In various embodiments, photoplethysmogram (PPG) sensor 115 includes an optical sensor including a light emitter and a light receptor 116. In various embodiments, photoplethysmogram (PPG) sensor 115 includes an optical sensor including an infrared light emitting diode (LED), red LED, other color LED, a red vertical-cavity surface-emitting laser (VCSEL) diode, an infrared VCSEL diode, other color VCSEL, a multi-wavelength/color LED, a multi-wavelength/color VCSEL diode, and/or a photodiode. In various embodiments, an activated red and infrared LED can be utilized to emit red and infrared light respectively, onto and/or through a surface such as, for example, an area on the back of a respective ear (e.g., opposite a concha) of subject 100, a surface of subject 100 over a mastoid region of the neck of the subject 100, or a surface over another region of the neck of a subject 100 (e.g., USP, LSP1, LSP2). In various embodiments, an activated red, green and infrared LED can be utilized to emit red, green, and infrared light respectively, onto and/or through such a surface of subject 100 suitable for sensing relevant physiological signals. The inventor has determined that using green LEDs, in addition to red and infrared LEDs provides an additional measurement at the same time that allows for motion-based error correction while keeping power consumption at approximately the same rate.

The inventor has determined a technique to accurately reconstruct motion-compromised PPG, blood oxygen saturation (i.e. pulse oximetry ($SpO_2$)), heart rate (HR), and/or heart rate variability (HRV) signals based on time-varying spectral analysis using a spectral filter algorithm. In various embodiments, the power spectral density of PPG (e.g., from PPG sensor 115) and accelerometer signals (e.g., from PPG sensor 115, from head motion sensor (114, 124), neck motion sensor (113, 123), general motion sensor (112, 122)) for each time shift of a windowed data segment is calculated. In various embodiments, frequency peaks resulting from motion artifacts are distinguished from the PPG spectrum by comparing time-varying spectra of PPG and accelerometer data. In various embodiments, a technique to accurately reconstruct motion-compromised PPG, $SpO_2$, HR, and/or HRV signals includes time-varying power spectral density (PSD) calculations; spectral filtering; motion artifact detection; HR and $SpO_2$ reconstruction, and signal reconstruction. In various embodiments, a first method is performed in which window-segmented power spectral density (PSD) of PPG and accelerometer signals is calculated in real-time to scale each estimate of the PSD by the equivalent noise bandwidth of the window. In various embodiments, a second method is performed in which PPG waveforms from green and infrared LED signals are used in motion artifact detection; HR and $SpO_2$ reconstruction, and signal reconstruction. The green PPG waveform is used for HR and SpO2 monitoring and the IR PPG signal waveform is used as the motion reference. In various embodiments, the motion removal process of the second method utilizes continuous wavelet transformations. In various embodiments, the two (2) calculated waveform sets from the first and second methods are compared and, if motion artifacts are positively identified, the first and second method results are blended with weight-based averages. In various embodiments, the value corresponding to the amount of carbon dioxide ($CO_2$) in the blood is estimated by applying a linear formula, linear correlation index, or machine learning bot opportunity to a collected sample size of the aforementioned vital sign measurement data.

In various embodiments, photoplethysmogram (PPG) sensor 115 includes a pulse oximetry sensor including a light emitter and light receptor. In various embodiments, one or more photodiodes can be utilized to receive and convert light reflected from a surface of a subject 100 into electric current that can be processed by a pulse oximetry sensor for the purpose of measuring and quantifying physiological signals from the area of the subject illuminated by the infrared LED, red LED, green LED and photodiode. In some embodiments, one or more photodiodes can be utilized to receive and convert light that is transmitted through a surface of a subject 100 into electric current. In various embodiments, a light emitter of PPG sensor 115 is configured to emit light in a direction toward the cavum concha of a subject 100 and a light receptor of PPG sensor 115 is configured to receive light reflected from the one or more sources (e.g., skin, blood, tissue) in the direction. In various embodiments, a light emitter of PPG sensor 115 is configured to emit light in a direction away from a surface of the neck over a mastoid region of a subject 100, or from another surface of the neck (e.g., USP, LSP1, LSP2), or of the skull, nose, or face (e.g., opposite a portion of an eyeglasses physiological sign monitoring portion) of the subject 100, and a light receptor of PPG sensor 115 is configured to receive light reflected from the one or more sources (e.g., skin, blood, tissue) in the direction. In various embodiments, a pulse oximetry sensor of PPG sensor 115 is configured to generate an electronic pulse oximetry signal based on the received, reflected light. In various embodiments, PPG sensor 115 includes one or more filters that are pre-programmed or pre-configured to filter reflected light from sources other than blood. In various embodiments, PPG sensor 115 is configured to detect and filter intermittent light and the first physiological sign portion 110 of monitoring device 140 is configured to use picket fence algorithms to reduce errors introduced by motion of a subject. In various embodiments, the second physiological sign portion 120 of enhanced monitoring device 140, in communication with first physiological sign portion 110 of enhanced monitoring device 140, is configured to use picket fence algorithms to reduce errors introduced by motion of a subject. In various embodiments, PPG sensor 115 may sense and/or process ambient light to calibrate readings of a light emitter and light receptor. In various embodiments, PPG sensor 115 is a minimal footprint (e.g., 0.05-75 millimeter (mm) (length), 0.05-75 mm (width), 0.05-25 mm (height)) and low-power (e.g., 0.1-5 milliwatts (mW)) analog and/or digital front-end integrated circuit including supporting electronics, designed, fabricated, and assembled on one or more layers of one or more flexible printed circuit and/or printed circuit board that constitutes part of an electronic subsystem of a physiological sign portion of enhanced monitoring device 140 (e.g., first physiological sign portion 110).

In various embodiments, PPG sensor 115 includes a plurality of interfaces to external electronics and/or external physical parameters such as, for example, a first interface to enable the supply of electricity to the sensor via electromechanical interconnect 105 and from a power source subsystem 128 that is part of an electronic subsystem of another portion of enhanced monitoring device 140 (e.g., second physiological sign portion 120), a second interface to coordinate transmission and/or reception of electronic signals such as, for example, digital control signals, variable analog signals, etc., to and/or from a light emitter and light receptor (e.g., infrared LED, red LED and photodiode), and a third interface to coordinate transmission and/or reception of electronic signals such as a clock, processed physiological signals data, etc., to and/or from a processor subsystem 132 that is part of an electronic subsystem of another portion of enhanced monitoring device 140 (e.g., second physiological sign portion 120). In various embodiments, PPG sensor 115 provides an electronic signal input to a respiratory rate sensor (not shown) or a pulse oximetry sensor (not shown) in one or more portions of enhanced monitoring device 140 (e.g., in second physiological sign portion 120). In various embodiments, PPG sensor 115 provides an electronic signal input to a heart rate sensor, a pulse transit time sensor, a pulse wave velocity sensor, a cuffless blood pressure sensor, an end-tidal $CO_2$ sensor, a coughing sensor, a sneezing sensor, and/or an arterial characteristics sensor. In various embodiments, PPG sensor 115 is configured to generate an electronic signal usable as an input (e.g., as one input of a plurality of inputs) to generate respective machine readable values indicative of a plurality of physiological signs for subject 100 including heart rate, respiratory rate, pulse transit time, pulse wave velocity, cuffless blood pressure, end-tidal $CO_2$ concentration within a subject's blood, coughing activity, sneezing activity, and/or arterial characteristics.

In various embodiments, head motion sensor (114, 124), neck motion sensor (113, 123), and motion sensor (112, 122) includes, for example, a multi-motion axis gyroscope, a multi-motion axis accelerometer, a multi-motion axis magnetometer, or combinations thereof. Any suitable number of axes can be utilized for the multi-motion axis motion sensor (112, 113, 114, 122, 123, 124). In various embodiments, the motion sensor (112, 113, 114, 122, 123, 124) includes a tri-axis accelerometer providing nine (9) axes of motion. In various embodiments, the number of axes for the multi-motion axis motion sensor (112, 113, 114, 122, 123, 124) is six (6). In some embodiments, the number of axes for the multi-motion axis motion sensor (112, 113, 114, 122, 123, 124) is eight (8). In various embodiments, BCG sensor (107, 127) includes a head motion sensor (114, 124). In various embodiments, head motion sensor (114, 124), neck motion sensor (113, 123), and motion sensor (112, 122) are each a minimal footprint (e.g., 0.05-75 mm (length), 0.05-75 mm (width), 0.05-25 mm (height)) and low-power (e.g., 0.1-10 mW) motion tracking integrated circuit including supporting electronics, designed, fabricated, and assembled on one or more layers of one or more flexible printed circuit and/or printed circuit board that constitutes part of an electronic subsystem of first portion 110. In various embodiments, head motion sensor (114, 124), neck motion sensor (113, 123), and motion sensor (112, 122) each include a plurality of interfaces to external electronics and/or external physical parameters such as, for example, a first interface to enable the supply of electricity to the respective sensor via electromechanical interconnect 105 and from a power source subsystem 128 that is part of an electronic subsystem of another portion of enhanced monitoring device 140 (e.g., second physiological sign portion 120) of enhanced monitoring device 140, a second interface to a plurality of intricate microelectromechanical structures internal to the integrated circuit of the respective motion sensor (112, 113, 114, 122, 123, 124) which include structures configured to be physically displaced in response to movement (head movement, neck movement, general movement) at the deployed surface of subject 100 such as, for example, a series of overlapping cantilever structures, and a third interface to coordinate transmission and/or reception of electronic signals such as a clock, processed physiological signals data, etc., to and/or from a processor subsystem 132 that is part of an electronic subsystem of another portion of enhanced monitoring device 140 (e.g., second physiological sign portion 120) of enhanced monitoring device 140.

In various embodiments, head motion sensor (114, 124), neck motion sensor (113, 123), and motion sensor (112, 122) are each configured to monitor respective motion of a subject relative to a motion axis and to generate an electronic motion signal based on the monitored motion. In various embodiments, head motion sensor (114, 124) and/or BCG sensor (107, 127) is configured to detect motion of a subject's head in response to heart beat to generate an electronic ballistocardiogram (BCG) signal. In various embodiments, motion sensor (112, 122) provides an electronic signal input to a blood pressure sensor, and as further detailed below. In various embodiments, one or more physiological sign portions (110, 120) of enhanced monitoring device 140 includes a blood pressure sensor including a motion sensor (112, 122). In various embodiments, motion sensor (112, 122) provides an electronic signal input to a subject activity level sensor, and/or arterial characteristics sensor. In various embodiments, an electronic ballistocardiogram (BCG) signal provided by a BCG sensor (107, 127), or a head motion sensor (114, 124) may be used to generate respective machine readable values indicative of the number of steps that a subject 100 has taken over a period of time, and/or taps and pulses to first physiological sign portion 110 of enhanced monitoring device 140 (and/or to second physiological sign portion 120 of enhanced monitoring device 140).

In various embodiments, neck motion sensor (113, 123) provides an electronic signal input to a respiratory rate sensor, a maximal oxygen uptake sensor, a stress sensor, a coughing sensor, and/or a sneezing sensor. In various embodiments, neck motion sensor (113, 123) is configured to respectively generate electronic signals which may be used as an input (e.g., as one of a plurality of inputs) to generate respective machine readable values indicative of a plurality of physiological signs for subject 100 including respiratory rate, maximal oxygen uptake, stress, coughing activity, and/or sneezing activity. The inventor has observed that the physical act of coughing or sneezing causes specific motions to the side of the neck. In various embodiments, neck motion sensor (113, 123) may be configured to measure these motions at a "Sempulse Point" (e.g., USP, LSP1, LSP2) by accelerometer motion patterns in a plurality of axes (e.g., in all 3 axes). The inventor has determined that these specific motions indicate and deliver coughing and sneezing metrics, including but not limited to coughing and sneezing rates, coughing and sneezing waveforms, and coughing and sneezing alarms. Coughing and sneezing have become critically important indicators with the rise of COVID-19 and future pandemics, because they can indicate early-onset symptoms or flag subjects as asymptomatic carriers. In various embodiments, head motion sensor (114, 124) provides an electronic signal input to a BCG sensor, a pulse transit time sensor, and/or a pulse wave velocity sensor.

In various embodiments, first and second physiological sign portions (110, 120) of enhanced monitoring device 140 each include an electrocardiogram (ECG) sensor (111, 121) configured to generate respective electronic signals which may be used as an input (e.g., as one of a plurality of inputs) to generate respective machine readable values indicative of a plurality of physiological signs for subject 100 including respiratory rate, pacemaker edge detection (e.g., with three chamber pacing with data logging and ECG tagging for three rising and falling edges), the time elapsed between successive heartbeats (R-R interval), pulse transit time, pulse wave velocity, ECG pulse rate, pulse deficit, premature ventricular complexes, heart rate variability, stress, subject activity level, and/or arterial characteristics. The inventor has determined that such values may be respectively generated accurately with ECG waveform inputs from at least two surface points of subject 100 as described above (e.g., first physiological sign portion 110 deployed on a surface on a back of a subject's ear (e.g., opposite a concha) or a surface of subject 100 over a mastoid region of the neck of subject 100, and second physiological sign portion 120 deployed on a surface of a subject 100 over another region of the neck of subject 100 (e.g., USP, LSP1, LSP2), or a skull, nose, or face surface of the subject 100 opposite a portion of an eyeglasses physiological sign monitoring portion 1620 (e.g., FIG. 16)). In various embodiments, ECG sensor is configured to calculate R-R interval using an adaptation of the Pan-Tompkins QRS detection algorithm as described below. In various embodiments, ECG sensor is configured to generate electronic signals which may be used to generate respective machine readable values indicative of R-R interval using an adaptation of the Pan-Tompkins QRS detection algorithm as described below.

In various embodiments, ECG sensor (111, 121) includes an electrical potential sensor and is configured to respectively generate electronic signals which may be used as an input (e.g., as one of a plurality of inputs) to generate respective machine readable values indicative of a plurality of physiological signs for subject 100 including stroke volume, heart rate, cardiac output, ventricular ejection time, and/or pre-ejection period. In various embodiments, ECG sensor (111, 121) includes an electrical potential sensor 111 that may be utilized to measure electrical potential at a respective surface of the subject 100. In various embodiments, one or more physiological sign portions (110, 120) of enhanced monitoring device 140 may include an electromyograph (EMG) sensor, and/or an electroencephalograph (EEG) sensor, which may respectively include an electrical potential sensor.

In various embodiments, ECG sensor (111, 121) is a minimal footprint (e.g., 0.05-75 mm (length), 0.05-75 mm (width), 0.05-25 mm (height)) sensor including one or more electrodes having rectilinear and/or non-rectilinear forms that are designed, fabricated, and assembled on one or more layers of one or more flexible printed circuit and/or printed circuit board that constitute part of an electronic subsystem of a respective physiological sign portion (110, 120). In various embodiments, ECG sensor (111, 121) includes a plurality of interfaces to external electronics and/or external physical parameters such as, for example, a first interface to enable the supply of electricity to the sensor via electromechanical interconnect 105 and from a power source subsystem 128 that is part of an electronic subsystem of another portion of enhanced monitoring device 140 (e.g., second physiological sign portion 120) of enhanced monitoring device 140, a second interface to one or more electrodes, and/or a capacitive touch controller subsystem of enhanced monitoring device 140 to coordinate transmission and reception of electronic signals such as changes in ambient capacitance to/from ECG sensor (111, 121), and a third interface to coordinate transmission and/or reception of electronic signals such as a clock, processed physiological signals data, etc., to and/or from a processor subsystem 132 that is part of an electronic subsystem of another portion of enhanced monitoring device 140 (e.g., second physiological sign portion 120) of enhanced monitoring device 140. In various embodiments, ECG sensor (111, 121) can be configured to monitor an electrical potential at a surface of a subject 100 and to generate an electronic electrical potential signal based on the monitored electrical potential.

In various embodiments, a physiological sign portion (110, 120) of enhanced monitoring device 140 (e.g., second physiological sign portion 120) may include an interface (e.g., snap button 160, FIG. 4) configured to receive a disposable electrode which may also serve as the attachment mechanism to attach the physiological sign portion to the surface of subject 100. In some embodiments, the interface is formed in a side of the physiological sign portion. In some embodiments, the interface is an attachment to the physiological sign portion. As illustrated in the example in FIG. 4, in some embodiments, second physiological sign portion 120 of enhanced monitoring device 140 may include a snap button including, for example, a female end configured to receive a male end of a disposable electrode (e.g., ECG electrode) of a suitable size (e.g., 2 mm, 3 mm, 4 mm, 6 mm, etc.) and suitable type (e.g., electrical skin electrode, transcutaneous electrical nerve stimulation (TENS) electrode, etc.). In various embodiments, the disposable electrode provides a clean electrical signal from the surface of subject 100 based on one or more respective monitored physiological parameters of subject 100, and holds the second physiological sign portion 120 of enhanced monitoring device 140 securely onto the subject 100.

Different disposable electrodes (e.g., ECG electrodes, TENS electrodes, etc.) have different adhesive characteristics, including, but not limited to, duration of wear, skin sensitivity, size, pliability, and holding strength to name a few. The physiological sign portions (110, 120) of enhanced monitoring device 140 will work with all of them, so the user of enhanced monitoring device is free to select the appropriate disposable electrode for their needs. In various embodiments, the interface (e.g., snap button 160, FIG. 4) may be configured to receive a compressible, foam ring (not shown) configured to be placed around the interface before attaching the corresponding electrode end to the interface of the physiological sign portion (110, 120). In some embodiments, this foam ring (not shown), when installed in place, is configured to compress and apply pressure to both the physiological sign portion (110, 120) and the disposable electrode, to limit the circular rotation, around the joined interface ends, of the physiological sign portion (110, 120) and the disposable electrode relative to each other. In various embodiments, the foam ring is a permanent feature on a custom-designed disposable electrode.

In various embodiments, one or more of the physiological sign portions (110, 120) of enhanced monitoring device 140 is configured to use both a wet electrode and a dry electrode. In various embodiments, the same electrode may detect and provide a plurality of measurement readings for a plurality of physiological parameters including, for example, ECG waveform data, Galvanic Skin response data, Bioimpedance (BioZ) data, skin resistivity/conductivity data, sweat chemistry/composition data, and skin temperature data. The inventor has determined that all such measurement readings can be collected by the respective physiological sign portion simultaneously and without interference or electrical issues. A dry electrode may be formed from any suitable electrically- and thermally-conductive substance such as, for example, 316-grade stainless steel.

As is known in the art, metal electrodes are typically chosen for medical devices, and virtually all conventional metal electrodes have flat surfaces and oblique angles that are not conducivetorecordingskinelectricalpropertiessinceskinis sopliableandflexiblewhilethebodyisinmotion.Also,asfurther detailedbelow,mostmetalscreateabatterywiththesaltsofthe skin,whichin-turnproducesfluctuatingandineffectiveread- ingswhilethischargeequalizationoccursforuptosixtyminutes. Invariousembodiments,oneormoreofthephysiologicalsign portions(110,120)ofenhancedmonitoringdevice140are configuredtousedisposableelectrodes(e.g.,silversilver-chlo- rideelectrodesincorporatingaflexible,electricallyconduc- tivegelforuseinestablishingalowresistancecontactwitha subject'sskinsurface)tomonitorskinresistanceand conductivitywhileasubject(e.g.,subject100)isactive.

As is known in the art, electrode-to-skin impedance plays a major role in biological signal quality. There inventor determined and observed a direct current (DC) potential difference as high as ±300 mV between biopotential electrodes caused by chemical interactions at the skin-electrode interface. Electrically- and thermally-conductive substances take a period of time for chemical interactions at the skin-electrode interface to come to charge equilibrium with the skin. The inventor has determined that high electrode-skin impedance negatively influences biological signal quality since it produces low SNR ratios and because it forms a strong barrier for the biopotentials to cross the highly-resistant skin layer, e.g., stratum corneum, that is in contact with electrodes and the low electron/ion exchange at electrode sites. The inventor has determined that this strong barrier for the biopotentials to cross the highly-resistant skin layer causes weak conductivity between the electrodes and the skin, and reduces the biological signal amplitude when vital signs monitors already need to measure such small differential signals between 3 μVpp-2 mVpp. As is known in the art, a mismatch in impedance between the electrodes at the skin surface during the recording of a biological signal would reduce the common mode rejection ratio of the recording system, increase common mode interference, and decrease the SNR ratio.

To reduce the time to skin-electrode equilibrium and eliminate variability between samples, in various embodiments, one or more of the physiological sign portions (110, 120) of enhanced monitoring device 140 may be configured to use an electrode with a thin layer of conductive carbon followed by a coating of Silver-Silver Chloride (Ag—AgCl). The inventor has determined that conductive carbon effectively seals the base material and insulates the second coating from any potential chemical reactions. The inventor has also determined that silver-silver chloride electrodes may act as non-polarizable electrodes and have low electrode-skin impedance, low noise, low motion artifacts, and have the ability to increase common mode rejection. The inventor has further determined that silver-silver chloride electrodes also have the lowest known interactions with skin, are skin-safe, and lower the impedance between a dry electrode and the skin.

As is known in the art, the world is heavily-flooded with radio frequencies and other forms of common mode interference. In various embodiments, and as described below, one or more portions of enhanced monitoring device 140 (e.g., second physiological sign portion 120) includes a communications interface (139). In various embodiments, communications interface 139 may include a Bluetooth LE wireless communication interface, which can saturate an input amplifier. To reduce and/or eliminate common mode interference around the portions of enhanced monitoring device 140, in various embodiments, signals from the plurality of electrodes for the physiological sign portions (110, 120) may be run in parallel between each other including, without limitation, traces on the PCB, the respective electrode path across the interconnect 105 between the physiological sign portions (110, 120), and the connection to an electrode interface of a physiological sign portion (e.g., snap button 160 of second physiological sign portion 120). The inventor has determined that this parallel trace acts as an antenna to ensure that each electrode cable receives the same common mode interference, and to ensure that the inputs are balanced. The inventor has also determined that, since the common mode interference is balanced on both electrodes, it can then effectively be eliminated as the remaining, balanced common mode interference may be filtered and rejected by, for example, an instrumentation amplifier for both electrodes equally. The inventor has further determined that, keeping each input balanced (i.e., same impedance, length, and susceptibility to noise), while also minimizing the capacitance to ground (e.g., <47 nF) and avoiding excessive parasitic capacitance to ground, allows, for example, an instrumentation amplifier to reject common mode signals.

In various embodiments, one or more physiological sign portions (110, 120) of enhanced monitoring device 140 may include a blood pressure sensor (not shown) that is configured to generate an electronic blood pressure signal. In various embodiments, a blood pressure sensor (not shown) is an arterial blood pressure sensor configured to monitor a subject's systolic and/or diastolic blood pressures and to generate an electronic systolic and/or diastolic blood pressure signal based on the monitored systolic and/or diastolic blood pressures. In various embodiments, a blood pressure sensor (not shown) is configured to receive an input from a PPG sensor 115 and a motion sensor (112, 122). For example, as is known to those skilled in the art, the pulse wave is a physiological phenomenon that occurs within the circulatory system during blood flow. During one heart systole, a volume of blood is expelled and this volume propagates through the arteries and veins. The motion of this propagation is due to the reciprocal transformation between the kinetic energy of a segment of the expelled blood volume and the potential energy of a stretched segment of the pliable vascular wall. The changes in pressure, blood flow, velocity, and vascular profile (diameter, shape, etc.) throughout the whole pulse wave can be directly measured and observed and can be used for classification of arterial elasticity and the blood's pressure. As is known to those skilled in the art, physicians were trained to estimate systolic blood pressure with their fingertips placed on the femoral artery. From this point the force distribution from the pressure wave in the blood vessel to the skin can be directly felt and measured.

The enhanced monitoring devices, systems, and methods described herein modernize this prior training and monitoring technique with advanced skin mechanics and technology hundreds of times more sensitive than the human fingertip. The forces exerted by the underlying arterial pressure (pulse) wave create arterial and venous elasticity waves and skin surface motions. In various embodiments, the enhanced monitoring devices, systems, and methods described herein may measure these elasticity waves and skin motions spatiotemporally and in three dimensions through the use of one or more of optical sensors that direct and receive light waves reflected off of the arterial and venous walls, sensitive accelerometers that can directly sense the pulse wave through its transferred force to the skin's surface, cameras that can detect the pulse wave through its transferred force to the skin's surface, and/or distance-sensing techniques (e.g., SONAR, LIDAR, etc.) that can detect pulse wave through its transferred force to the skin's surface.

In various embodiments, enhanced monitoring device 140 includes a PPG sensor 115, including an optical sensor with infrared, red, and green LEDs and a photodetector, and a motion sensor (112, 122) including a 3-axis accelerometer (e.g., configured to be deployed at a respective point of at least one physiological sign portion (e.g., 110)). In various embodiments, a physiological sign portion (110, 120) of enhanced monitoring device 140 may include a camera (not shown) and/or distance-sensing technique system (not shown). As described herein, the respective sensing points (e.g., on the back of an ear, over a mastoid region, USP, LSP1, LSP2) are over the superficial arteries of subject 100, corresponding sensors in one or more physiological sign portions (110, 120) of enhanced monitoring device 140 may continuously detect blood pressure waveforms and other physiological parameters such as heart rhythm, respiratory rhythm, and pulse rate directly from the vascular system. In various embodiments, PPG sensor 115, and a motion sensor (112, 122) and/or BCG sensor (107, 127), can provide, in combination, a resilient, opto-mechanical sensor that is configured to use the force waves detected in both methods to provide a single, clean blood pressure force waveform. In various embodiments, in the case of high general motion of the subject 100, such as in running, weighting factors may be used in the motion-based techniques so more of an emphasis is placed on the arterial wall methodologies.

In various embodiments, as an added layer of measurement, the known distance between the physiological sign measurement points of subject 100 (e.g., distance between the first physiological sign monitoring portion 110 and second physiological sign monitoring portion 120) may be used to further refine and clarify the force waveforms by way of creating a composite waveform over the multiple measurements that provides more accurate pattern and pulse wave data. The inventor has determined, through test subject data, that the enhanced monitoring devices, systems, and methods described herein provide clear pulse waveforms with distinct peaks and shapes that were characteristic of arterial pulses taken with more-invasive techniques. The inventor has also catalogued specific optical signatures, motion patterns, and force waveform patterns that have been shown to directly correlate to systolic and diastolic blood pressure and, as the force vectors are represented as spatiotemporal information, the inventor has performed this measurement continuously at low power.

In various embodiments, one or more physiological sign portions (110, 120) of enhanced monitoring device 140 may include a heart rate sensor (not shown) that is configured to be utilized to sense and/or process heart rate of a subject 100. In various embodiments, heart rate sensor may be configured to take measurements directly with physical blood pulses. In various embodiments, heart rate sensor may receive an input from PPG sensor 115. In various embodiments, heart rate sensor may include, for example, an electrical potential sensor as described above, a motion sensor as described above, a light emitter and light receptor as described above, or combinations thereof. In various embodiments, heart rate sensor is a minimal footprint (e.g., 0.05-75 mm (length), 0.05-75 mm (width), 0.05-25 mm (height)) and low-power (e.g., 0.1-5 mW) integrated circuit including supporting electronics, designed, fabricated, and assembled on one or more layers of one or more flexible printed circuit and/or printed circuit board that constitutes part of an electronic subsystem of a portion of enhanced monitoring device 140 (e.g., of first physiological portion 110). In various embodiments, heart rate sensor may include an integrated math engine configured to process electronic signals received from PPG sensor 115 within an integrated circuit. In various embodiments, heart rate sensor may include a plurality of interfaces to external electronics and/or external physical parameters such as, for example, a first interface to enable the supply of electricity to the sensor via electromechanical interconnect 105 and from a power source subsystem 138 that is part of an electronic subsystem of a portion of enhanced monitoring device 140 (e.g., of second physiological sign portion 120), a second interface to a PPG sensor 115 (or, for example, to a light emitter and light receptor, motion sensor, electrical potential sensor, etc.), and a third interface to coordinate transmission and/or reception of electronic signals such as a clock, processed physiological signals data, etc., to and/or from a processor subsystem 132 that is part of an electronic subsystem of a portion of enhanced monitoring device 140 (e.g., of second physiological sign portion 120). In various embodiments, heart rate sensor can be configured to monitor a pulse rate of a subject 100 and to generate an electronic heart rate signal based on the monitored pulse rate.

In various embodiments, one or more physiological sign portions (110, 120) of enhanced monitoring device 140 may include a respiratory rate sensor (not shown) configured to sense and/or process respiratory rate of a subject 100. In various embodiments, respiratory rate sensor may receive an input from an ECG sensor (111, 121), PPG sensor (115), and/or neck motion sensor (113, 123). In various embodiments, respiratory rate sensor may include a neck motion sensor and take measurements directly with physical respiration motion data observed from the neck (e.g., in electronic signals generated by neck motion sensor 113 in first physiological sign portion 110 and/or by neck motion sensor 123 in second physiological sign portion 120). In various embodiments, respiratory rate sensor includes, for example, an acoustic transducer integrated circuit configured to sense respiratory rate. In various embodiments, respiratory rate sensor is a minimal footprint (e.g., 0.05-75 mm (length), 0.05-75 mm (width), 0.05-25 mm (height)) and low-power (e.g., 0.1-5 mW) integrated circuit including supporting electronics, designed, fabricated, and assembled on one or more layers of one or more flexible printed circuit and/or printed circuit board that constitutes part of an electronic subsystem of a portion of enhanced monitoring device 140 (e.g., of first physiological sign portion 110). In various embodiments, respiratory rate sensor may include an integrated math engine configured to process electronic signals received from one or more of ECG sensor (111, 121), PPG sensor (115), neck motion sensor (113, 123), an acoustic transducer integrated circuit, within an integrated circuit. In various embodiments, respiratory rate sensor includes a plurality of interfaces to external electronics and/or external physical parameters such as, for example, a first interface to enable the supply of electricity to the sensor via electromechanical interconnect 105 and from a power source subsystem 128 that is part of an electronic subsystem of a portion of enhanced monitoring device 140 (e.g., of second physiological sign portion 120), a second interface to ECG sensor (111, 121), PPG sensor (115), neck motion sensor (113, 123), and/or an acoustic transducer integrated circuit, and a third interface to coordinate transmission and/or reception of electronic signals such as a clock, processed physiological signals data, etc., to and/or from a processor subsystem 132 that is part of an electronic subsystem of a portion of enhanced monitoring device 140 (e.g., of second physiological sign portion 120). In various embodiments, respiratory rate sensor may be configured to monitor a breathing rate of a subject 100 and to generate an electronic respiratory rate signal based on the monitored respiratory rate.

In various embodiments, a physiological sign portion (e.g., 110) of enhanced monitoring device 140 may include an orientation sensor 108 that includes, for example, a multi-orientation axis gyroscope, a multi-orientation axis accelerometer, a multi-orientation axis magnetometer, or combinations thereof. Any suitable number of axes can be utilized for the multi-orientation axis orientation sensor 108. In various embodiments, orientation sensor 108 may sense and/or process movements of the subject such as, for example, movements associated with sitting, standing, walking, lying face down, laying face up, or any other suitable orientation, including subtle localized body movements that can be correlated to internal biological activities or signals such as breathing rate, etc. In various embodiments, orientation sensor 108 includes a tri-axis accelerometer providing nine (9) axes of orientation. In various embodiments, the number of axes for the multi-orientation axis orientation sensor 108 is six (6). In some embodiments, the number of axes for the multi-orientation axis orientation sensor 108 is eight (8). In various embodiments, orientation sensor 108 is a minimal footprint (e.g., 0.05-75 mm (length), 0.05-75 mm (width), 0.05-25 mm (height)) and low-power (e.g., 0.1-10 mW) orientation tracking integrated circuit including supporting electronics, designed, fabricated, and assembled on one or more layers of one or more flexible printed circuit and/or printed circuit board that constitutes part of an electronic subsystem of a portion of enhanced monitoring device 140 (e.g., of first physiological sign portion 110). In various embodiments, an orientation sensor 108 includes a plurality of interfaces to external electronics and/or external physical parameters such as, for example, a first interface to enable the supply of electricity to the sensor via electromechanical interconnect 105 and from a power source subsystem 128 that is part of an electronic subsystem of a portion of enhanced monitoring device 140 (e.g., of second physiological sign portion 120), a second interface to a plurality of intricate microelectromechanical structures internal to the integrated circuit of orientation sensor 108 which include structures configured to be physically displaced in response to movement at the deployed surface of subject 100 such as, for example, a series of overlapping cantilever structures, and a third interface to coordinate transmission and/or reception of electronic signals such as a clock, processed physiological signals data, etc., to and/or from a processor subsystem 132 that is part of an electronic subsystem of a portion of enhanced monitoring device 140 (e.g., of second physiological sign portion 120). In various embodiments, orientation sensor 108 is configured to monitor an orientation of a subject relative to an orientation axis and to generate an electronic orientation signal based on the monitored orientation. In various embodiments, orientation sensor 108 is configured to monitor an orientation of a subject relative to a plurality of orientation axes and to generate an electronic orientation signal based on the monitored orientation and indicative of the subject 100 standing, walking, running, kneeling, sitting, lying face up, lying face down, laying on a side, and/or in a vehicle. In various embodiments, motion sensor 112 and orientation sensor 108 are the same sensor. In various embodiments, motion axes of motion sensor 112 and orientation axes of orientation sensor 108 are the same axes.

In various embodiments, at least one physiological sign portion (e.g., 110 and 120) of enhanced monitoring device 140 may include a temperature sensor (e.g., skin temperature sensor 106, 126) and may be utilized to sense and/or process physiological parameters such as, for example, body temperature or skin temperature. In some embodiments, a temperature sensor (e.g., skin temperature sensor 106, 126) may also be configured to process environmental parameters such as, for example, ambient temperature. In various embodiments, a temperature sensor (e.g., skin temperature sensor 106, 126) of enhanced monitoring device 140 may include, for example, a transducer integrated circuit configured to utilize silicon structures contained therein to sense ambient temperature, a resistance temperature detector (RTD), a thermistor, a thermocouple, or combinations thereof. In various embodiments, a temperature sensor (e.g., skin temperature sensor 106, 126) of enhanced monitoring device 140 may include an infrared thermopile sensor. In various embodiments, skin temperature sensor (106, 126) may provide an electronic signal input to a core body temperature sensor (not shown) or a cranial temperature sensor (not shown) in one or more portions of enhanced monitoring device 140 (e.g., in second physiological sign portion 120). In various embodiments, skin temperature sensor (106, 126) is configured to generate an electronic signal usable as an input (e.g., as one input of a plurality of inputs) to generate respective machine readable values indicative of a plurality of physiological signs for subject 100 including core body temperature and cranial temperature. In various embodiments, a temperature sensor (e.g., skin temperature sensor 106, 126) of enhanced monitoring device 140 is a minimal footprint (e.g., 0.05-75 mm (length), 0.05-75 mm (width), 0.05-25 mm (height)) and low-power (e.g., 0.1-5 mW) infrared thermopile sensor integrated circuit including supporting electronics, designed, fabricated, and assembled on one or more layers of one or more flexible printed circuit and/or printed circuit board that constitutes part of an electronic subsystem of first portion 110. In various embodiments, a temperature sensor (e.g., skin temperature sensor 106, 126) of enhanced monitoring device 140 includes an integrated math engine configured to process electronic signals received from one or more infrared thermopile sensors within an integrated circuit. In various embodiments, a temperature sensor includes a plurality of interfaces to external electronics and/or external physical parameters such as, for example, a first interface to enable the supply of electricity to the sensor via electromechanical interconnect 105 and from a power source subsystem 128 that is part of an electronic subsystem of a portion of enhanced monitoring device 140 (e.g., of second physiological sign portion 120), a second interface to materials such as, for example, a thermopile, having physical properties sensitive to variations in ambient temperature, and a third interface to coordinate transmission and/or reception of electronic signals such as a clock, processed physiological signals data, etc., to and/or from a processor subsystem 132 that is part of an electronic subsystem of a portion of enhanced monitoring device 140 (e.g., of second physiological sign portion 120). In various embodiments, skin temperature sensor (106, 126) may be configured to monitor a temperature at a surface, and/or a temperature around a surface, of a subject 100 and to generate an electronic temperature signal based on the monitored temperature.

In various embodiments, at least one physiological sign portion (e.g., 110 and 120) of enhanced monitoring device 140 may include a skin conductance and/or skin resistance sensor (e.g., 109, 129) that may be utilized to sense and/or process skin conductance and/or skin resistivity. In various embodiments, skin conductance and/or skin resistance sensor (e.g., 109, 129) may include, for example, an electrical potential sensor as described above configured to measure electrical conductivity between the skin cells on the surface of subject 100. In various embodiments, skin conductance and/or skin resistance sensor (e.g., 109, 129) may be configured to provide an electronic signal input to a galvanic skin response sensor (not shown), a hydration sensor (not shown), a stress sensor (not shown), or a bioimpedance sensor (not shown) in one or more portions of enhanced monitoring device 140 (e.g., in second physiological sign portion 120). In various embodiments, skin conductance and/or skin resistance sensor (e.g., 109, 129) may be configured to generate electronic signals which may be used as an input (e.g., as one input of a plurality of inputs) to generate respective machine readable values indicative of a plurality of physiological signs for subject 100 including galvanic skin response, hydration level, stress level, or bioimpedance (bioZ).

In various embodiments, a physiological sign portion (e.g., 120) of enhanced monitoring device 140 may include a sweat chemistry/composition sensor (e.g., 116) that may be utilized to sense and/or process sweat chemistry and/or sweat composition. In various embodiments, sweat chemistry/composition sensor (e.g., 116) may include, for example, a molecular chemical receptor, a physico-chemical detector element (e.g., a transducer such as, for example, an optical, impedance-based, ion-selective electrode, and/or piezoelectric transducer), an enzyme recognition element, and/or an electrical potential sensor as described above. In various embodiments, sweat chemistry/composition sensor (e.g., 116) may be configured to provide an electronic signal input to a hydration sensor (not shown), a stress sensor (not shown), or a glucose level sensor (not shown) in one or more portions of enhanced monitoring device 140 (e.g., in second physiological sign portion 120). In various embodiments, skin conductance and/or skin resistance sensor (e.g., 109, 129) may be configured to generate electronic signals which may be used as an input (e.g., as one input of a plurality of inputs) to generate respective machine readable values indicative of a plurality of physiological signs for subject 100 including hydration level, stress level, or glucose level.

As discussed above, in various embodiments, second physiological sign monitoring portion 120 of enhanced monitoring device 140 may be configured for deployment on a different, respective surface of subject 100 than first physiological sign monitoring portion 110 of enhanced monitoring device 140 such as, for example, on a surface over a region of the neck of the subject 100 (e.g., surface in USP, LSP1, or LSP2, FIG. 2A-2C), or a skull, nose, or face surface of the subject 100 opposite a portion of an eyeglasses physiological sign monitoring portion 1620 (e.g., FIG. 16), for sensing one or more physiological parameters of such subject 100. In various embodiments, as discussed above, second physiological sign portion 120 of enhanced monitoring device 140 may include an adhesive surface to attach a surface of second physiological sign portion 120 of enhanced monitoring device 140 to a surface of a subject 100. In some embodiments, second physiological sign portion 120 of enhanced monitoring device 140 includes additional adhesive for reusability such as, for example, as attached to a battery cover of a second physiological sign portion 120 or other slide device of a second physiological sign portion 120.

In various embodiments, another portion (not shown) of enhanced monitoring device 140 may include a device such as, for example, a clip or a pin, to attach the other portions (not shown) to an item of clothing, lanyard, etc., worn by subject 100 such as, for example, the collar or pocket of a shirt. In various embodiments, enhanced monitoring device 140 includes one or more environmental sensors. In various embodiments, in addition to physiological sensors (e.g., one or more of ECG sensor 121, BCG sensor 127, skin temperature sensor 126, skin conductance and/or resistance sensor 129, sweat chemistry/composition sensor 116, head motion sensor 124, neck motion sensor 123, motion sensor 122), second physiological sign portion 120 of enhanced monitoring device 140 may include one or more environmental sensors. In some embodiments, another portion (not shown) of enhanced monitoring device 140 may include one or more environmental sensors. In various embodiments, the environmental sensors are non-invasive.

In various embodiments, as illustrated in FIG. 4, an electronic subsystem of second physiological sign portion 120 of enhanced monitoring device 140 may include, in addition to physiological sensors, one or more environmental sensors 135, a location (e.g., global positioning system (GPS)) subsystem 132, an audio input/output subsystem 133, a biometric subsystem 134, a radio frequency identification (RFID) subsystem 136, a liquid (e.g., blood) sensor 137, communications interface 139, processor 142, memory 143, and/or a power subsystem 148. In various embodiments, enhanced monitoring device 140 may include first 110 and second 120 physiological sign portions and another portion (not shown) including one or more environmental sensors 135, a location (e.g., global positioning system (GPS)) subsystem 132, an audio input/output subsystem 133, a biometric subsystem 134, a radio frequency identification (RFID) subsystem 136, a liquid (e.g., blood) sensor 137, communications interface 139, processor 142, memory 143, and/or a power subsystem 148. In various embodiments, the one or more environmental sensors 135 may include, for example, an ambient temperature sensor, an ambient pressure sensor, a humidity sensor, an altitude sensor (altimeter), a UV index sensor, an ambient light sensor, or combinations thereof.

Any suitable environmental sensor may be included as the one or more environmental sensors. For example, in various embodiments, second 120 physiological sign portion of enhanced monitoring device 140 may include an ambient temperature sensor (e.g., embedded digital thermometer), an ambient pressure sensor (e.g., embedded barometric pressure sensor), a humidity sensor (e.g., embedded humidistat sensor), an altitude sensor (e.g., receiving signals from an embedded pressure sensor and location subsystem (e.g., GPS)), and a UV index sensor (e.g., embedded ambient light sensor). The inventor has observed that ambient temperature impacts the human body through its thermoregulation systems which can impact a subject's physiological signs through changes in arterial and venous diameters and through sweat, impacting skin surface sensing of physiological signs. The inventor has observed that barometric pressure changes directly impact blood pressure because of the difference in pressure in and around a subject's body, and that elevation impacts a subject's blood pressure for the same reason. The inventor has observed that elevation also changes a subject's respiration patterns and in turn the subject's PPG waveforms and pulse oximetry waveforms. The inventor has also observed that relative humidity changes impact skin sensing physiological signs through an increase in sweat and also negatively impact skin resistivity/conductivity. The inventor has further observed that UV Index can directly impact optical sensors that use light sources and detectors to determine physiological signs. The inventor has also observed that a light sensor's ability to discern natural light from artificial light can also determine impacts to the skin and the ability to sense physiological signs from it due to different light and heat combinations' effects on the skin. In various embodiments, an electronic subsystem of second physiological sign portion 120 may include a unique identification value such as, for example, a predetermined resistor value, that is identifiable by an electronic subsystem of electromechanical interconnect 105 and/or an electronic subsystem of first physiological sign portion 110.

In various embodiments, second physiological sign portion 120 of enhanced monitoring device 140 (or another portion (not shown) of enhanced monitoring device 140) may include a pressure sensor (not shown) configured to monitor ambient pressure (e.g., atmospheric pressure) around the deployed, respective surface of the subject 100. In various embodiments, pressure sensor includes one or more minimal footprint (e.g., 0.05-75 mm (length), 0.05-75 mm (width), 0.05-25 mm (height)) and low-power (e.g., 0.1-5 mW) barometer integrated circuits including supporting electronics, designed, fabricated, and assembled on one or more layers of one or more flexible printed circuit and/or printed circuit board that constitutes part of an electronic subsystem of second physiological sign portion 120 of enhanced monitoring device 140 (or another portion (not shown) of enhanced monitoring device 140). In various embodiments, such one or more barometer integrated circuits can include analog and/or digital front-end circuitry configured to process electronic signals from a pressure sensing element within the integrated circuit. In various embodiments, a pressure sensor includes a plurality of interfaces to external electronics and/or external physical parameter such as, for example, a first interface to enable the supply of electricity to the sensor from power source subsystem 138 that is part of an electronic subsystem of second physiological sign portion 120 of enhanced monitoring device 140 (or another portion (not shown) of enhanced monitoring device 140), a second interface to a plurality of microelectromechanical structures internal to said integrated circuit that may be configured to be physically displaced and/or deflected in response to variation in ambient pressure around the deployed respective surface of subject 100 such as, for example, a suspended diaphragm, and a third interface to coordinate transmission and/or reception of electronic signals such as a clock, processed environmental signals data, etc., to and/or from processor 142. In various embodiments, a pressure sensor may be configured to sense and/or process environmental signals such as air pressure around the deployed, respective surface of subject 100. In various embodiments, a pressure sensor can be configured to monitor ambient pressure around a surface of a subject 100 and to generate an electronic ambient pressure signal based on the monitored ambient pressure. In various embodiments, a pressure sensor may be configured to operate as an altimeter and monitor altitude of a subject 100. In various embodiments, a pressure sensor may sense and/or process ambient pressure to calibrate, or provide a quantified context for, sensed blood oxygen saturation data received by second portion 120 via electromechanical interconnect 105 in the form of electronic signals generated by a PPG sensor 115 of first physiological sign portion 110.

In various embodiments, second physiological sign portion 120 of enhanced monitoring device 140 (or another portion (not shown) of enhanced monitoring device 140) may include a humidity sensor (not shown) configured to monitor humidity around the deployed, respective surface of the subject 100. In various embodiments, humidity sensor includes one or more minimal footprint ((e.g., 0.05-75 mm (length), 0.05-75 mm (width), 0.05-25 mm (height)) and low-power (e.g., 0.1-5 mW) humidity sensor integrated circuits including supporting electronics, designed, fabricated, and assembled on one or more layers of one or more flexible printed circuit and/or printed circuit board that constitutes part of an electronic subsystem of second physiological sign portion 120 of enhanced monitoring device 140 (or another portion (not shown) of enhanced monitoring device 140). In various embodiments, such humidity sensor integrated circuits can include a temperature sensor and an integrated signal processor configured to process electronic signals received from one or more humidity sensor devices within said integrated circuit. In various embodiments, a humidity sensor includes a plurality of interfaces to external electronics and/or external physical parameters such as, for example, a first interface to enable the supply of electricity to the sensor from power source subsystem 138 that is part of an electronic subsystem of second physiological sign portion 120 of enhanced monitoring device 140 (or another portion (not shown) of enhanced monitoring device 140), a second interface to materials that are designed and assembled in such a manner as to be sensitive to humidity-related variations in their localized environment such as, for example, a dielectric material (e.g., polyamide), and a third interface to coordinate transmission and/or reception of electronic signals such as a clock, processed environmental signals data, etc., to and/or from processor 142. In various embodiments, a humidity sensor may be configured to sense and/or process environmental signals such as, for example, humidity and temperature around a surface of a subject. In various embodiments, a humidity sensor can be configured to monitor ambient humidity around a respective, deployed surface of a subject 100 and to generate an electronic ambient humidity signal based on the monitored ambient humidity. In various embodiments, a humidity sensor may sense and/or process ambient humidity to calibrate, or provide a quantified context for, liquid data monitored at liquid (e.g., blood) sensor 137 of second physiological sign portion 120 of enhanced monitoring device 140 (or another portion (not shown) of enhanced monitoring device 140).

In various embodiments, second physiological sign portion 120 of enhanced monitoring device 140 (and/or another portion (not shown) of enhanced monitoring device 140) may include a UV index sensor, an ambient light sensor, and an altitude sensor (altimeter), respectively configured to monitor UV index and ambient light around the respective, deployed surface of the subject 100, and to monitor altitude of the subject 100. In various embodiments, UV index sensor and ambient light sensor include one or more minimal footprint (e.g., 0.05-75 mm (length), 0.05-75 mm (width), 0.05-25 mm (height)) and low-power (e.g., 0.1-5 mW) integrated circuits including supporting electronics, designed, fabricated, and assembled on one or more layers of one or more flexible printed circuit and/or printed circuit board that constitutes part of an electronic subsystem of second physiological sign portion 120 of enhanced monitoring device 140 (or another portion (not shown) of enhanced monitoring device 140). In various embodiments, such integrated circuits can include a proximity sensor, analog and/or digital front-end circuitry, and a signal processor configured to process electronic signals from UV sensor, ambient light, and proximity sensor elements within the integrated circuit. In some embodiments, the UV index sensor, the ambient light sensor, and the proximity sensor are implemented in separate integrated circuits or combinations thereof. In various embodiments, a UV index sensor and/or an ambient light sensor include a plurality of interfaces to external electronics and/or external physical parameters such as, for example, a first interface to enable the supply of electricity to the sensor from power source subsystem 138 that is part of an electronic subsystem of second physiological sign portion 120 of enhanced monitoring device 140 (or another portion (not shown) of enhanced monitoring device 140), a second interface to structures of, for example, one or more light (e.g., infrared) emitters, photodiodes, light receptors, that are internal to an integrated circuit and may be configured to emit light and/or receive light from their respective environment, and a third interface to coordinate transmission and/or reception of electronic signals such as a clock, processed environmental signals data, etc., to and/or from processor 142. In various embodiments, a UV index sensor, an ambient light sensor, and/or an altimeter may be configured to sense and/or process environmental signals such as, for example, UV index and/or ambient light around a respective, deployed surface of a subject and/or altitude of a subject. In various embodiments, a UV index sensor and/or an ambient light sensor can be configured to monitor UV index and/or ambient light around a respective, deployed surface of a subject 100 and to generate an electronic UV index and/or ambient light signal based on the monitored UV index and/or ambient light. In various embodiments, an altitude sensor may be configured to monitor altitude of a subject and to generate an electronic altitude signal based on the monitored altitude. In various embodiments, a UV index sensor, ambient light sensor, and/or an altitude sensor may sense and/or process UV index, ambient light, and/or altitude to calibrate, or provide a quantified context for, sensed blood oxygen saturation data monitored by a PPG sensor in physiological sign portion 120 of enhanced monitoring device 140 or received by second physiological sign portion 120 via electromechanical interconnect 105 in the form of electronic signals generated by a PPG sensor (115) of first physiological sign portion 110.

In various embodiments, second physiological sign portion 120 of enhanced monitoring device 140 (and/or another portion (not shown) of enhanced monitoring device 140) may include an ambient temperature sensor configured to monitor ambient temperature around a respective, deployed surface of a subject 100. In various embodiments, ambient temperature sensor includes, for example, a transducer integrated circuit configured to utilize silicon structures contained therein to sense ambient temperature, a resistance temperature detector (RTD), a thermistor, a thermocouple, or combinations thereof, as described above for temperature sensor 106, 126. In various embodiments, ambient temperature sensor includes an infrared thermopile sensor. In various embodiments, an ambient temperature sensor may be configured to sense and/or process environmental signals such as air temperature around a respective, deployed surface of a subject. In various embodiments, an ambient temperature sensor can be configured to monitor ambient temperature around a respective, deployed surface of a subject 100 and to generate an electronic ambient temperature signal based on the monitored ambient temperature. In various embodiments, an ambient temperature sensor may sense and/or process ambient temperature to calibrate, or provide a quantified context for, skin, body, and/or cranial temperature data of a subject and monitored by, and/or calculated using signals from, a temperature sensor (e.g., skin temperature sensor 126) in second physiological sign portion 120 of enhanced monitoring device 140 or received by second physiological sign portion 120 via electromechanical interconnect 105 in the form of electronic signals generated by a temperature sensor (e.g., skin temperature sensor 106) of first physiological sign portion 110.

In various embodiments, second physiological sign portion 120 of enhanced monitoring device 140 (and/or another portion (not shown) of enhanced monitoring device 140) may include a motion tracking subsystem configured to monitor motion of the subject 100. In various embodiments, a motion tracking subsystem 121 includes a head motion sensor 124, neck motion sensor 123, and/or motion sensor 122 as described above. In various embodiments, a motion tracking subsystem is configured to monitor motion of a subject relative to a motion axis and to generate an electronic motion signal based on the monitored motion. In various embodiments, including embodiments in which at least one motion sensor (e.g., 114, 113, 112) is also provided in first physiological sign portion 110, a motion tracking subsystem (in second physiological sign portion 120 and/or another portion of enhanced monitoring device 140) may receive motion data via electromechanical interconnect 105 in the form of electronic signals generated by a motion sensor in first physiological sign portion 110. In various embodiments, a motion tracking subsystem (e.g., in second physiological sign portion 120 of enhanced monitoring device 140 (and/or another portion (not shown) of enhanced monitoring device 140) provides an electronic signal input to a location subsystem (e.g., 132).

In various embodiments, first physiological sign portion 110 includes at least one motion sensor (e.g., 114, 113, 112), and second physiological sign portion 120 of enhanced monitoring device 140 includes a motion tracking subsystem including at least one motion sensor (e.g., 124, 123, 122), where each motion sensor is configured to generate electronic motion signals. In various embodiments, the generated electronic motion signals may be used to calibrate, or provide a quantified context for, one or more physiological parameters and/or physiological signs of one or more subjects. For example, the generated electronic motion signals may be used to double-check heart rate, and/or maximal oxygen uptake, calculations from the PPG sensor (and/or ECG sensor), to double-check respiratory rate, and/or maximal oxygen uptake, calculations from the PPG and/or ECG sensor, to double-check blood pressure calculations using the combination of the PPG sensor and ECG sensor, and/or using the combination of the PPG sensor and the BCG sensor. In various embodiments, the generated electronic motion signals may be used to validate that each sensor reading is within tolerances. In various embodiments, the second physiological sign portion 120 of enhanced monitoring device 140 includes a motion tracking subsystem including at least one motion sensor (e.g., 124, 123, 122) to filter out motion errors in at least one motion sensor (e.g., 114, 113, 112) of first physiological sign portion 110 while a monitored subject 100 is moving. For example, the motion value (e.g., in respectively generated electronic motion signals) of a motion sensor (e.g., 124, 123, 122) of second physiological sign portion 120 may be subtracted from the motion value (e.g., in respectively generated electronic motion signals) of a motion sensor (e.g., 114, 113, 112) of first physiological sign portion 110.

In various embodiments, second physiological sign portion 120 of enhanced monitoring device 140 (and/or another portion (not shown) of enhanced monitoring device 140) may include a location subsystem 132 configured to monitor location of the subject 100. In various embodiments, location subsystem 132 includes a global navigation satellite system (e.g., GPS) receiver, another suitable location sensor, or combinations thereof. In various embodiments, location subsystem 132 utilizes a non-GPS protocol (e.g., Galileo, GLONASS, Beidou, etc.). In various embodiments, location subsystem 132 includes a GPS receiver that is configured to use the global GPS network to determine global coordinates of a subject within a predetermined tolerance. In various embodiments, location subsystem 132 includes a plurality of interfaces to external electronics and/or external physical parameters such as, for example, a first interface to enable the supply of electricity to the sensor from power source subsystem 138 that is part of an electronic subsystem of second physiological sign portion 120 of enhanced monitoring device 140 (or another portion (not shown) of enhanced monitoring device 140), a second interface to electronics configured to receive and/or process high-frequency electronic signals directly from, for example, a satellite navigation system, an antenna, an electronic filter, a low-noise amplifier, or combinations thereof, and a third interface to coordinate transmission and/or reception of electronic signals such as a clock, data, etc., to and/or from processor 142. In various embodiments, location subsystem 132 may be configured to sense and/or process the geolocation of a subject 100. The inventor has observed that a GPS receiver consumes a large amount of power from power source subsystem 138. Thus, in various embodiments, location subsystem 132 may include a mechanism such as, for example, a timing circuit, to switch power to the GPS receiver on and off periodically to obtain a reference location of subject 100 for location subsystem 132. In various embodiments, location subsystem 132 includes a compass and receives motion data in the form of electronic signals generated by a motion sensor (e.g., 124, 123, 122) of second physiological sign portion 120, or received via electromechanical interconnect 105 in the form of electronic signals generated by a motion sensor (e.g., 114, 113, 112) of first physiological sign portion 110. In various embodiments, location subsystem 132 includes an integrated math engine configured to process electronic signals including reference location data received from a GPS receiver, electronic signals including motion data from a motion sensor (e.g., 124, 123, 122) of second physiological sign portion 120, and electronic signals including direction data from a compass. In various embodiments, location subsystem 132 may be configured to monitor location of a subject 100, and to generate an electronic location signal based on the monitored location.

In various embodiments, second physiological sign portion 120 of enhanced monitoring device 140 (and/or another portion (not shown) of enhanced monitoring device 140) may include an audio in/out subsystem 133 configured to monitor sound around a surface of the subject 100. In various embodiments, audio in/out subsystem 133 may include one or more minimal footprint (e.g., 0.05-75 mm (length), 0.05-75 mm (width), 0.05-25 mm (height)) and low-power (e.g., 0.1-10 mW) integrated circuits including supporting electronics including, for example, a microphone, a speaker, a buzzer, a noisemaker, or combinations thereof, designed, fabricated, and assembled on one or more layers of one or more flexible printed circuit and/or printed circuit board that constitutes part of an electronic subsystem of second physiological sign portion 120 of enhanced monitoring device 140 (or another portion (not shown) of enhanced monitoring device 140). In various embodiments, such integrated circuits can include, for example, an electronic filter, an amplifier, an analog-to-digital converter, a digital-to-analog converter, and a processor configured to process electronic signals from one or more microphones and/or processors, and electronic signals transmitted to one or more speakers within the integrated circuit. In various embodiments, audio in/out subsystem 133 includes a plurality of interfaces to external electronics and/or external physical parameters such as, for example, a first interface to enable the supply of electricity to the subsystem from power source subsystem 138 that is part of an electronic subsystem of second physiological sign portion 120 of enhanced monitoring device 140 (or another portion (not shown) of enhanced monitoring device 140), a second interface to receive and/or process electronic signals from, for example, a microphone and/or a processor, a third interface to electronics configured to transmit and/or process electronic signals to be transmitted to one or more speakers, and a fourth interface to coordinate transmission and/or reception of electronic signals such as a clock, data, etc., to and/or from processor 142. In various embodiments, audio in/out subsystem 133 may capture, process, and/or transmit audio data such as user voice commands, alarm and/or status audio indicators, heart sounds, lung sounds, breathing sounds, sounds that indicate severe pain such as screams, other biological sounds, etc., from and/or to an ambient environment of the audio in/out subsystem. In various embodiments, audio in/out subsystem 133 can capture and/or process internal body sounds, and/or external sounds from subject 100. In various embodiments, audio in/out subsystem 133 is configured to provide active and/or passive monitoring of subject 100 by an operator of a mobile communication and display device (e.g., 800) and/or remote physician. In various embodiments, audio in/out subsystem 133 is configured to provide for communication between a monitored subject 100 and an operator of a mobile communication and display device (e.g., 800) (and/or remote physician). In various embodiments, audio in/out subsystem 133 is configured to provide recording of the scene locally and/or remotely (e.g., at a mobile communication and display device (e.g., 800).) In various embodiments, audio in/out subsystem 133 is configured to provide echo location of the scene and/or aid in locating subject 100. In various embodiments, audio in/out subsystem 133 is configured to provide for consciousness checking of the subject 100 by an operator of a mobile communication and display device (e.g., 800) and/or remote physician. For example, if an alert is made, the subject 100 can prove that they are conscious by tapping the device or pressing the button the requested number of times or by repeating the requested phrase. In various embodiments, and as described below, audio in/out subsystem 133 is configured to improve the severity scoring of subject 100 by listening for motion, talking, or screams.

In various embodiments, second physiological sign portion 120 of enhanced monitoring device 140 (and/or another portion (not shown) of enhanced monitoring device 140) may include a liquid (e.g., blood) sensor 137 configured to detect liquid at and/or around a surface of the subject 100. In various embodiments, liquid sensor 137 includes one or more minimal footprint (e.g., 0.05-75 mm (length), 0.05-75 mm (width), 0.05-25 mm (height)) and low-power (e.g., 0.1-5 mW) integrated circuits including supporting electronics, designed, fabricated, and assembled on one or more layers of one or more flexible printed circuit and/or printed circuit board that constitutes part of an electronic subsystem of second physiological sign portion 120 of enhanced monitoring device 140 (and/or another portion (not shown) of enhanced monitoring device 140). In various embodiments, such integrated circuits may include a liquid sensor such as a liquid leakage sensor (e.g., light emitter, light receptor, photodiode), a liquid sensor amplifier, analog and/or digital front-end circuitry, and/or a signal processor, configured to process electronic signals from liquid sensor elements within the integrated circuit. In various embodiments, liquid sensor 137 may include a plurality of interfaces to external electronics and/or external physical parameters such as, for example, a first interface to enable the supply of electricity to the sensor from power source subsystem 138 that is part of an electronic subsystem of second physiological sign portion 120 of enhanced monitoring device 140 (and/or another portion (not shown) of enhanced monitoring device 140), a second interface to coordinate transmission and/or reception of electronic signals such as, for example, digital control signals, variable analog signals, etc., to and/or from, for example, light emitter, light receptor, photodiode, liquid sensor amplifier, that are internal to an integrated circuit and may be configured to emit light and/or receive light to detect the presence of a liquid, and a third interface to coordinate transmission and/or reception of electronic signals such as a clock, processed environmental signals data, etc., to and/or from processor 142. In various embodiments, liquid sensor 137 may be configured to sense, detect, and/or process environmental signals such as, for example, the presence of a liquid, and/or a liquid type, at and/or around a respective, deployed surface of the subject 100. In various embodiments, liquid sensor 137 can be configured to detect liquid at and/or around a deployed surface of a subject 100 and to generate an electronic liquid signal based on the detected liquid.

In various embodiments, second physiological sign portion 120 of enhanced monitoring device 140 (and/or another portion (not shown) of enhanced monitoring device 140) may include an indicator subsystem (not shown) and one or more indicators such as, for example, light emitting diodes (LEDs). In various embodiments, an indicator subsystem includes one or more minimal footprint (e.g., 0.05-75 mm (length), 0.05-75 mm (width), 0.05-25 mm (height)) and low-power (e.g., 0.1-5 mW) integrated circuits including supporting electronics such as, for example, LEDs, piezoelectric or other suitable vibrator, user input interfaces such as, for example, touch screen controllers, buttons, or switches, digital displays such as, for example, liquid crystal display (LCD), or organic light emitting diode (OLED) display, tactile sensors, haptic technology, or combinations thereof, designed, fabricated, and assembled on one or more layers of one or more flexible printed circuit and/or printed circuit board that constitutes part of an electronic subsystem of second physiological sign portion 120 of enhanced monitoring device 140 (and/or another portion (not shown) of enhanced monitoring device 140). In various embodiments, such integrated circuits can include, for example, a digital-to-analog converter, an analog-to-digital converter, a control logic subsystem, power management subsystem, electronic signal drivers, or combinations thereof. In various embodiments, an indicator subsystem includes a plurality of interfaces to external electronics and/or external physical parameters such as, for example, a first interface to enable the supply of electricity to the subsystem from power source subsystem 138 that is part of an electronic subsystem of second physiological sign portion 120 of enhanced monitoring device 140 (and/or another portion (not shown) of enhanced monitoring device 140), a second interface to receive and/or process electronic signals from, for example, processor, a button, a switch, and/or a haptic sensor, a third interface to electronics configured to transmit and/or process electronic signals to be transmitted to, for example, one or more LEDs, digital displays such as, for example, LCD and/or OLED displays, and/or a vibrator, and a fourth interface to coordinate transmission and/or reception of electronic signals such as a clock, data, etc., to and/or from processor 142. In various embodiments, an indicator subsystem (not shown) may capture, process, and/or transmit capture and/or process inputs such as, for example, user commands, and to display and/or communicate status information such as, for example, remaining battery capacity and/or signal threshold crossings. In various embodiments, indicator subsystem (not shown) may include multi-color LEDs to alert the subject 100 and caregivers of the subject's status levels and to aid in locating the subject 100.

In various embodiments, second physiological sign portion 120 of enhanced monitoring device 140 (and/or another portion (not shown) of enhanced monitoring device 140) may include a radio-frequency identification (RFID) subsystem 136. In various embodiments, RFID subsystem 136 includes an RFID tag associated to a unique identification string for each enhanced monitoring device 140. In various embodiments, RFID subsystem 136 may broadcast its unique identification string for registration purposes with a mobile communication and display device (described in more detail below). In various embodiments, RFID subsystem 136 includes one or more minimal footprint (e.g., 0.05-75 mm (length), 0.05-75 mm (width), 0.05-25 mm (height)) and low-power (e.g., 0.1-5 mW) integrated circuits including supporting electronics such as, for example, antenna, power supply circuitry, or combinations thereof, designed, fabricated, and assembled on one or more layers of one or more flexible printed circuit and/or printed circuit board that constitutes part of an electronic subsystem of second physiological sign portion 120 of enhanced monitoring device 140 (and/or another portion (not shown) of enhanced monitoring device 140). In various embodiments, such integrated circuits can include, for example, control logic subsystem, a power management subsystem, transmitter, and receiver circuitry, memory, or combinations thereof. In various embodiments, RFID subsystem 136 may be a passive implementation such that it obtains power wirelessly from radio waves received from an external RFID reader and/or near field communication (NFC) subsystem. In various embodiments, RFID subsystem 136 may be an active implementation such that it obtains power from a local power source. In various embodiments, RFID subsystem 136 includes a NFC integrated circuit and a NFC antenna. In various embodiments, RFID subsystem 136 includes a Zigbee integrated circuit and a Zigbee antenna. In various embodiments, RFID subsystem 136 includes an ANT integrated circuit and an ANT antenna. In various embodiments, RFID subsystem 136 includes a Bluetooth LE integrated circuit and a Bluetooth LE antenna. In various embodiments, RFID subsystem 136 includes a RFID integrated circuit and a RFID antenna. In various embodiments, RFID subsystem 136 includes a plurality of interfaces to external electronics and/or external physical parameters such as, for example, a first interface to enable the supply of electricity to the subsystem from power source subsystem 138 that is part of an electronic subsystem of second physiological sign portion 120 of enhanced monitoring device 140 (and/or another portion (not shown) of enhanced monitoring device 140) and/or an external radio-frequency identification reader subsystem, a second interface to antenna and/or electronics configured to receive and/or transmit radio waves from and/or to an internal and/or external RFID and/or NFC subsystem, a third interface to coordinate transmission and/or reception of electronic signals such as a clock, data, etc., to and/or from processor 142. In various embodiments, RFID subsystem 136 may be configured to activate or wake up electronic subsystem of second physiological sign portion 120 of enhanced monitoring device 140 (and/or another portion (not shown) of enhanced monitoring device 140). In various embodiments, RFID subsystem 136 may be configured to wirelessly relay stored information such as date of manufacture, model number, etc., between an electronic subsystem 116 of first 110 and/or second physiological sign portions and an external radio-frequency identification reader or near-field communication subsystem. In various embodiments, RFID subsystem 136 can include a Quick Response (QR) code, or other suitable barcode, disposed, for example, on a surface of a housing of enhanced monitoring device 140. In various embodiments, the QR code, or other suitable barcode, may be configured to store information such as, for example, a date of manufacture of enhanced monitoring device 140 or second physiological sign portion 120 of enhanced monitoring device 140 (and/or another portion (not shown) of enhanced monitoring device 140), model number of enhanced monitoring device 140 or second physiological sign portion 120 of enhanced monitoring device 140 (and/or another portion (not shown) of enhanced monitoring device 140), that can be communicated to (e.g., wirelessly and/or optically read by) an external reader configured to read and process the QR code or other suitable barcode.

In various embodiments, second physiological sign portion 120 of enhanced monitoring device 140 (and/or another portion (not shown) of enhanced monitoring device 140) may include a biometric subsystem 134. In various embodiments, biometric subsystem 134 includes one or more biometric sensors such as, for example, a fingerprint sensor, or retina sensor. In various embodiments, biometric subsystem 134 includes one or more minimal footprint (e.g., 0.05-75 mm (length), 0.05-75 mm (width), 0.05-25 mm (height)) and low-power (e.g., 0.1-5 mW) integrated circuits including supporting electronics designed, fabricated, and assembled on one or more layers of one or more flexible printed circuit and/or printed circuit board that constitutes part of an electronic subsystem of second physiological sign portion 120 of enhanced monitoring device 140 (and/or another portion (not shown) of enhanced monitoring device 140). In various embodiments, such integrated circuits can include, for example, analog and/or digital front-end circuitry, memory, light emitter, light receptor, piezoelectric transducer, capacitor, and a signal processor configured to process electronic signals from light emitter, light receptor, piezoelectric transducer, and/or capacitor elements, within the integrated circuit, or combinations thereof. In various embodiments, biometric subsystem 134 includes a plurality of interfaces to external electronics and/or external physical parameters such as, for example, a first interface to enable the supply of electricity to the subsystem from power source subsystem 138 that is part of an electronic subsystem of second physiological sign portion 120 of enhanced monitoring device 140 (and/or another portion (not shown) of enhanced monitoring device 140), a second interface to structures of, for example, one or more light (e.g., infrared) emitters, photodiodes, light receptors, piezoelectric transducers, capacitors, that are internal to an integrated circuit and may be configured to emit light and/or receive light including biometric data, emit and/or receive acoustic energy including biometric data, from a finger (or an eye) of a subject 100, a third interface to electronics configured to receive and/or transmit electronic signals including biometric data (e.g., fingerprint data, retina data), from and/or to biometric subsystem 134 and external electronic subsystems of monitoring device 140 including, for example, processor 142 and memory 143, and a fourth interface to coordinate transmission and/or reception of electronic signals such as a clock, data, etc., to and/or from processor 142. In various embodiments, biometric subsystem 134 may be configured to sense and/or process light, acoustic energy, etc. including biometric data, for processing, storage, and/or transmission to a mobile communication and display device (e.g., 800).

In various embodiments, second physiological sign portion 120 of enhanced monitoring device 140 (and/or another portion (not shown) of enhanced monitoring device 140) may include a power source subsystem 138. In various embodiments, power source subsystem 138 includes one or more minimal footprint (e.g., 1-20 mm diameter, 1-20 mm (length), 1-20 mm (width), 0.1-20 mm (height)) rechargeable and/or non-rechargeable, replaceable and/or non-replaceable batteries. In various embodiments, power source subsystem 138 includes one or more of such batteries and supporting electronics such as, for example, battery protection circuitry. Any suitable chemistry, shape, and form, of battery can be used such as, for example, lithium ion, lithium polymer, zinc air, coin cell, prismatic, bendable, or combinations thereof. In various embodiments, power source subsystem 138 includes a rechargeable lithium ion battery. In various embodiments, power source subsystem 138 includes rechargeable coin cell batteries. In various embodiments, power source subsystem 138 includes a battery, a photovoltaic cell, energy harvesting subsystems utilizing physical properties such as, for example, thermal or piezoelectricity, a super-capacitor, or combinations thereof, and supporting electronics. Power source subsystem 138 may be directly or indirectly connected to the subsystems within the electronic subsystems of the enhanced monitoring device including electronic subsystems of the first physiological sign portion 110 and second physiological sign portion 120

(and/or other portions (not shown) of enhanced monitoring device 140), to facilitate providing such subsystems with energy.

In various embodiments, power source subsystem 138 includes a plurality of interfaces to external electronics and/or external physical parameters such as, for example, a first interface to enable the conversion of non-electrical energy into electrical energy, for example as implemented in a photovoltaic cell, a second interface to facilitate the dissemination of energy from the power source subsystem 138 to the subsystems within the electronic subsystems of the enhanced monitoring device including electronic subsystems of the first physiological sign portion 110 and second physiological sign portion 120 (and/or other portions (not shown) of enhanced monitoring device 140). In various embodiments, power source subsystem 138 includes a removable battery. In various embodiments, power source subsystem 138 includes a non-removable battery. In various embodiments, power source subsystem 138 includes a USB connection to receive power from a remote source while charging rechargeable coin cell batteries as described below for the power source charger subsystem (not shown). In various embodiments, power source subsystem 138 may be operably coupled to a tactile switch of second physiological sign portion 120 of enhanced monitoring device 140 (and/or another portion (not shown) of enhanced monitoring device 140) (not shown) with a long hold to measure consciousness of subject 100, to power on/off enhanced monitoring device 140, and/or to switch operating modes of enhanced monitoring device 140. The enhanced monitoring devices, systems, and methods described herein may acquire subject physiological signs without the need for corded charging or battery replacements such as, for example, by using a combination of body power, solar power, and wireless charging. In various embodiments, depending upon the immediate power needs of any particular enhanced monitoring device, any or a combination of all of these methods may be used. In various embodiments, power source subsystem 138 harnesses power from the subject's body via thermoelectric generators, piezoelectricity, etc. The inventor has determined that, since the subject's body is expending energy through movement and by producing endothermic heat, this energy can be captured by power source subsystem 138 and used to power and/or recharge low-voltage devices like an enhanced monitoring device 140 that is deployed on a surface of the subject's body. In various embodiments, power source subsystem 138 harnesses power from outside light sources via photovoltaic cells. In various embodiments, the outside of one or more portions (e.g., 110, 120) may be lined with photovoltaic cells and be configured to be used to power and/or recharge low-voltage devices that reside on the body. Another benefit of photovoltaic cells observed by the inventor is their ability to act as ambient light sensors. In various embodiments, power source subsystem 138 utilizes varying wireless charging techniques to allow for the charging of the enhanced monitoring device without having to remove the enhanced monitoring device such as, for example, a pad under a subject's pillow that charges a device on a subject's head or a transmitter that charges an enhanced monitoring device while at a distance and within the range of a transmitter of the enhanced monitoring device.

In various embodiments, second physiological sign portion 120 of enhanced monitoring device 140 (and/or another portion (not shown) of enhanced monitoring device 140) may include a processor 142. In various embodiments, processor 142 includes one or more minimal footprint (e.g., 0.05-75 mm (length), 0.05-75 mm (width), 0.05-25 mm (height)) and low-power (e.g., 0.1-20 mW) integrated circuits and supporting electronics, for example, oscillator circuitry, designed, fabricated, and assembled on one or more flexible printed circuit and/or printed circuit board that constitutes part of an electronic subsystem of second physiological sign portion 120 of enhanced monitoring device 140 (and/or another portion (not shown) of enhanced monitoring device 140). In various embodiments, such integrated circuits can include, for example, clock management subsystem, an energy management subsystem, a memory subsystem, an input and/or output port subsystem, a serial interface subsystem, a timer subsystem, an encryption subsystem, an amplifier, an analog signal processor, a digital signal processor, a floating point unit, a central processing unit (CPU), or combinations thereof. For example, processor 142 may include a micro-controller unit (MCU) with digital signal processing (DSP) functionality. In various embodiments, processor 142 includes a plurality of interfaces to external electronics and/or external physical parameters such as, for example, a first interface to enable the supply of electricity to processor 142 from power source subsystem 138 that is part of an electronic subsystem of second physiological sign portion 120 of enhanced monitoring device 140 (and/or another portion (not shown) of enhanced monitoring device 140), a second interface to coordinate one or more electronic signal links between processor 142 and one or more oscillators configured to influence the operational frequency of processor 142, a third interface to coordinate transmission and/or reception of electronic signals such as a clock, analog and/or digital data, between processor 142 and other subsystems within the electronic subsystems of the enhanced monitoring device 140 including electronic subsystems of the first physiological sign portion 110 and second physiological sign portion 120 such as, for example, memory 143, communications interface 139, PPG sensor 115, ECG sensor (116, 126), pulse rate sensor 117, head motion sensor (114, 124), neck motion sensor (113, 123), motion sensor (112, 122), skin temperature sensor (106, 126), skin conductance and resistance sensor (109, 129), orientation sensor 108, the one or more environmental sensors 135, location subsystem 132, audio input/output subsystem 133, biometric subsystem 134, radio frequency identification (RFID) subsystem 136, liquid sensor 137, and a third interface to coordinate transmission and/or reception of electronic signals such as a clock, data, etc., to and/or from processor 142 and external electronic systems such as a personal computer (PC) and/or other mobile computing devices. In various embodiments, processor 142 may be programmed to acquire, aggregate, process, and/or transmit electronic signals from and/or to other subsystems within and/or external to electronic subsystems within second portion 120. In various embodiments, processor 142 may be programmed to implement a plurality of algorithms such as, for example, power optimization, physiological, environmental and/or other signal processing, real-time operating system, algorithms, or combinations thereof. In various embodiments, processor 142 may be programmed to coordinate local and/or external data storage in memory.

In various embodiments, second physiological sign portion 120 of enhanced monitoring device 140 (and/or another portion (not shown) of enhanced monitoring device 140) may include memory 143. In various embodiments, memory 143 includes one or more minimal footprint (e.g., 0.05-75 mm (length), 0.05-75 mm (width), 0.05-25 mm (height)) and low-power (e.g., 0.1-10 mW) integrated circuits and supporting electronics, designed, fabricated, and assembled on one or more flexible printed circuit and/or printed circuit board that constitutes part of an electronic subsystem of second physiological sign portion 120 of enhanced monitoring device 140 (and/or another portion (not shown) of enhanced monitoring device 140). In various embodiments, such integrated circuits can include, for example, a control logic subsystem, electrical switches, electrical storage elements, high voltage generator, or combinations thereof. In various embodiments, memory 143 includes a plurality of interfaces to external electronics and/or external physical parameters such as, for example, a first interface to enable the supply of electricity to memory 143 from power source subsystem 138 that is part of an electronic subsystem of second physiological sign portion 120 of enhanced monitoring device 140 (and/or another portion (not shown) of enhanced monitoring device 140), a second interface to coordinate transmission and/or reception of electronic signals such as a clock, analog and/or digital data, between memory 143 and other subsystems within the electronic subsystems of the monitoring device including electronic subsystems of the first physiological sign portion 110 and second physiological sign portion 120 such as, for example, processor 142. In various embodiments, memory 143 may include a volatile and/or non-volatile random access memory (RAM) and/or read only memory (ROM) device configured to store information such as, for example, instructions, processed and/or raw data, or combinations thereof. In various embodiments, memory 143 may store processed biological and/or environmental signal data until a time when such data is transferred to other subsystems within and/or external to electronic subsystems within enhanced monitoring device 140 including subsystems within second physiological sign portion 120 of enhanced monitoring device 140 (and/or another portion (not shown) of enhanced monitoring device 140).

In various embodiments, second physiological sign portion 120 of enhanced monitoring device 140 (and/or another portion (not shown) of enhanced monitoring device 140) may include a communications interface 139. In various embodiments, communications interface 139 includes one or more minimal footprint (e.g., 0.05-75 mm (length), 0.05-75 mm (width), 0.05-25 mm (height)) and low-power (e.g., 0.1-20 mW) integrated circuits and supporting electronics, such as, for example, an electronic filter, an antenna, or combinations thereof, designed, fabricated, and assembled on one or more flexible printed circuit and/or printed circuit board that constitutes part of an electronic subsystem of second physiological sign portion 120 of enhanced monitoring device 140 (and/or another portion (not shown) of enhanced monitoring device 140). In various embodiments, communications interface 139 can include one or more wireless transceivers combined into a single integrated circuit. In various embodiments, communications interface 139 can include one or more wireless transmitters, and one or more wireless receivers, in respective, separate integrated circuits. In various embodiments, such integrated circuits include, for example a 802.11 subsystem, a Wi-Fi subsystem, a Bluetooth subsystem, a Zigbee subsystem, an ANT subsystem, an NFC subsystem, a near field magnetic induction subsystem, a 3G/4G/5G cellular subsystem, a RF, VHF/UHF or other high frequency radio subsystem, a wireless USB subsystem, a wired subsystem, an electronic filter, a processor, a power management subsystem, an oscillator, or combinations thereof. In various embodiments, communications interface 139 includes a plurality of interfaces to external electronics and/or external physical parameters such as, for example, a first interface to enable the supply of electricity to memory 143 from power source subsystem 138 that is part of an electronic subsystem of second physiological sign portion 120 of enhanced monitoring device 140 (and/or another portion (not shown) of enhanced monitoring device 140), a second interface to one or more antenna and/or electronics configured to receive and/or transmit radio waves from and/or to an internal and/or external electronic subsystem of enhanced monitoring device 140, a third interface to coordinate the transmission and/or reception of electronic signals such as clock, data, etc., to and/or from processor 142 that is part of an electronic subsystem of second physiological sign portion 120 of enhanced monitoring device 140 (and/or another portion (not shown) of enhanced monitoring device 140), and a fourth interface to coordinate one or more electronic signal links between communications interface 139 and one or more oscillators configured to influence the operational frequency of communications interface 139. In various embodiments, communications interface 139 can be configured to wirelessly transfer raw and/or processed physiological, environmental, and/or system status data between an external electronic device and an electronic subsystem of enhanced monitoring device 140. In various embodiments, communications interface 139 can be configured to wirelessly upgrade programs and/or data embedded in an electronic subsystem of enhanced monitoring device 140. In various embodiments, communications interface 139 can be configured to transfer raw and/or processed physiological, environmental, and/or system status data over a wired connection between an external electronic device (e.g., mobile phone, computer) and an electronic subsystem of enhanced monitoring device 140. In various embodiments, one or more enhanced monitoring devices may be configured to act as a monitoring device hub in which a plurality of enhanced monitoring devices in communication range of each other form an ad hoc network via respective communications interfaces 139. In various embodiments, the communications interface 139 of the monitoring device hub in such an ad hoc network may be configured to receive respective electronic signals based on respective monitored physiological parameters of respective subjects from each of the other enhanced monitoring devices in the ad hoc network. In various embodiments, the communications interface 139 of the monitoring device hub is configured to communicate the aggregated electronic signals to one or more mobile communication and display devices (e.g., 800).

In various embodiments, and as described in more detail below, enhanced monitoring devices may work independently, may work in mesh networks, may be linked with physical connections, or may be virtually linked with each virtually-linked, enhanced monitoring device having a respective independent Internet Protocol (IP) connection to an intranet or the Internet via its respective communications interface 139. In various embodiments, each enhanced monitoring device of a plurality of enhanced monitoring devices may be configured to operate as an independent beacon, act as a repeater and a range extender, and be configured to communicate with emergency management devices within their respective operating range. In various embodiments, each such enhanced monitoring device then caches and repeats this communication either directly to its intended target (if the target is also communicatively connected to this enhanced monitoring device repeater), or the cached communication is routed across the network until it reaches its destination. For example, in a disaster scene (e.g., a natural disaster such as a tsunami, tornado, etc., a man-made disaster such as a mass shooting, structure fire, etc.), the first responders, EMTs, fire fighters, police, and any other emergency personnel will have varying equipment that will saturate the available bandwidth and also complicate the logistics of centralizing the data from disparate devices. The inventor has determined that the enhanced monitoring devices, systems, and methods described herein permit smaller cells of devices to communicate in their immediate vicinity, interconnect the devices within such cells, and handle the long-range communications to an intranet or the Internet. The inventor has determined that the enhanced monitoring devices, systems, and methods described herein serve to both extend the range of emergency devices and extend the capabilities of emergency management consoles and devices. As is known in the art, in practice, Bluetooth, Bluetooth LE, and WiFi devices have physical limitations due to memory restrictions, operating restrictions, and power restrictions. The inventor has determined that repeater devices described herein reduce the number of wireless connections handled by the user devices and simply feed them the data of the emergency devices (e.g., enhanced monitoring devices, other electronic devices used for evaluating, triaging, servicing, treating, helping, and surveying a disaster area, emergency medicine area, any area of distress, or any area with a gathering of people, etc.), effectively giving them an unlimited number of virtual connections.

In various embodiments, the power subsystem 138 of enhanced monitoring device 140 is battery-powered, but accommodates wired/wireless charging and running off of external power, as described below. In various embodiments, the communications interface 139 of enhanced monitoring device 140 has multiple radios and antennas to handle very high numbers of Bluetooth, Bluetooth LE, and WiFi wireless signals. In various embodiments, the communications interface 139 of enhanced monitoring device 140 is equipped with global and satellite IP connectivity via cellular and satellite networks that allow it to communicate with intranets and/or the Internet. In various embodiments, the communications interface 139 of enhanced monitoring device 140 includes a port, as described below, to connect to a cell phone or private radio for the purposes or communicating on intranets and/or the Internet, either in an encrypted or unencrypted manner. In various embodiments, the communications interface 139 of enhanced monitoring device 140 includes and operates using physical and information security through the encryption of data at rest and in motion.

In various embodiments, second physiological sign portion 120 of enhanced monitoring device 140 (and/or another portion (not shown) of enhanced monitoring device 140) may include a power source fuel gauge subsystem (not shown). In various embodiments, a power source fuel gauge subsystem includes one or more minimal footprint (e.g., 0.05-75 mm (length), 0.05-75 mm (width), 0.05-25 mm (height)) and low-power (e.g., 0.1-5 mW) integrated circuits including supporting electronics, designed, fabricated, and assembled on one or more flexible printed circuit and/or printed circuit board that constitutes part of an electronic subsystem of second physiological sign portion 120 of enhanced monitoring device 140 (and/or another portion (not shown) of enhanced monitoring device 140). In various embodiments, such integrated circuits can include, for example, an analog-to-digital converter, memory, a central processing unit (CPU) configured to facilitate calculating battery discharge rate, remaining energy capacity, or combinations thereof. In various embodiments, a power source fuel gauge subsystem includes a plurality of interfaces to external electronics and/or external physical parameters such as, for example, a first interface to enable the supply of electricity to the subsystem from power source subsystem 138 that is part of an electronic subsystem of second physiological sign portion 120 of enhanced monitoring device 140 (and/or another portion (not shown) of enhanced monitoring device 140), and a second interface to coordinate transmission and/or reception of electronic signals such as a clock, data, etc., to and/or from processor 142. In various embodiments, a power source fuel gauge subsystem may be configured to process, for example, battery capacity, state-of-charge, battery voltage, or combinations thereof.

In various embodiments, second physiological sign portion 120 of enhanced monitoring device 140 (and/or another portion (not shown) of enhanced monitoring device 140) may include a power source charger subsystem (not shown). In various embodiments, a power source charger subsystem includes one or more minimal footprint (e.g., 0.05-75 mm (length), 0.05-75 mm (width), 0.05-25 mm (height)) and low-power (e.g., 0.1-5 mW) integrated circuits including supporting electronics, designed, fabricated, and assembled on one or more flexible printed circuit and/or printed circuit board that constitutes part of an electronic subsystem of second physiological sign portion 120 of enhanced monitoring device 140 (and/or another portion (not shown) of enhanced monitoring device 140). In various embodiments, such integrated circuits can include, for example, a control logic subsystem, a short-circuit recovery subsystem, electronic switches, or combinations thereof. In various embodiments, a power source charger subsystem includes a plurality of interfaces to external electronics and/or external physical parameters such as, for example, a first interface to enable the wired or wireless supply of electricity from an external power source such as, for example, a Universal Serial Bus (USB) port, a main power adapter, a photovoltaic cell, a thermal or piezoelectric energy harvester, a wireless charging pad, a second interface to coordinate the transmission of electricity from the power source charger subsystem to the power source subsystem 138 that is part of an electronic subsystem of second physiological sign portion 120 of enhanced monitoring device 140 (and/or another portion (not shown) of enhanced monitoring device 140), and a third interface to coordinate transmission and/or reception of electronic signals such as a clock, data, etc., to and/or from processor 142. In various embodiments, power source charger subsystem may be configured to charge a rechargeable power source subsystem 128. In various embodiments, power source charger subsystem may be configured to independently or simultaneously supply power a rechargeable power source subsystem 138 and other subsystems within the electronic subsystems of the monitoring device including electronic subsystems of the first physiological sign portion 110 and second physiological sign portion 120.

In various embodiments, second physiological sign portion 120 of enhanced monitoring device 140 (and/or another portion (not shown) of enhanced monitoring device 140) may include a power distribution subsystem (not shown). In various embodiments, a power distribution subsystem includes one or more minimal footprint (e.g., 0.05-75 mm (length), 0.05-75 mm (width), 0.05-25 mm (height)) and low-power (e.g., 0.1-20 mW) integrated circuits and supporting electronics, designed, fabricated, and assembled on one or more flexible printed circuit and/or printed circuit board that constitutes part of an electronic subsystem of second physiological sign portion 120 of enhanced monitoring device 140 (and/or another portion (not shown) of enhanced monitoring device 140). In various embodiments, such integrated circuits can include, for example, a linear regulator circuitry, a switching regulator circuitry, a voltage and/or current monitor circuitry, an analog-to-digital converter, a digital-to-analog converter, a voltage reference circuitry, or combinations thereof. In various embodiments, a power distribution subsystem includes one or more networks of specialized circuitry that may be configured to, for example, distribute appropriate voltage and/or current characteristics to appropriate subsystems, monitor voltage and/or current characteristics delivered to various subsystems, monitor and/or optimize power consumption and/or other related parameters of various subsystems, within the electronic subsystems of the monitoring device including electronic subsystems of the first physiological sign portion 110 and second physiological sign portion 120.

In various embodiments, second physiological sign portion 120 of enhanced monitoring device 140 (and/or another portion (not shown) of enhanced monitoring device 140) may include a computer port subsystem (not shown). In various embodiments, a computer port subsystem includes one or more minimal footprint (e.g., 0.05-75 mm (length), 0.05-75 mm (width), 0.05-25 mm (height)) and low-power (e.g., 0.1-10 mW) connectors, electronics and/or program interface, implemented in one or more subsystems of enhanced monitoring device 140, such as, for example, processor 142. In various embodiments, such connectors, electronics and/or program interface, are designed, fabricated and implemented on one or more flexible printed circuit and/or printed circuit board and/or cable assembly, that constitutes part of an electronic subsystem of monitoring device, including an electronic subsystem of second physiological sign portion 120 of enhanced monitoring device 140 (and/or another portion (not shown) of enhanced monitoring device 140). In various embodiments, a computer port subsystem may include one or more ports configured to facilitate the transfer of electronic signals between electronic subsystems of enhanced monitoring device 140, and one or more external electronics such as, for example, an external power supply, an external mobile or non-mobile computing device, external bio-potential electrodes, for example, external bio-potential electrodes for EEG, ECG, EMG, measurements, a partial or complete capnometer, or combinations thereof. In various embodiments, a computer port subsystem may be configured to facilitate the transfer of electronic signals between electronic subsystems of enhanced monitoring device 140. In various embodiments, a computer port subsystem may include a port such as, for example, a universal serial bus (USB) port, or other suitable serial or parallel communication ports, configured to transfer power, clock, and data, etc. signals between electronic subsystems of enhanced monitoring device 140 to, for example, charge power source subsystem 138, transfer data into and/or out of processor 143. In various embodiments, a computer port subsystem may include one or more of such ports that are configured connect external EEG (e.g., cap plugin module), ECG (e.g., multi-lead plugin module), EMG, $CO_2$ breath monitor plugin module, blood pressure cuff plugin module, or other suitable bio-potential electrodes, and/or other devices and/or electronics such as, for example, a capnometer, to electronic subsystems of enhanced monitoring device 140.

In various embodiments, electronic subsystems of first physiological sign portion 110 and second physiological sign portion 120 can be rearranged, repositioned, and/or further integrated into one or more compact designed housings configured to fit ergonomically, minimally-intrusively, and entirely on two or more surface areas available on the back of a subject's ear (e.g., opposite a concha), on a neck surface over a mastoid region of the neck of a subject, on another neck surface of a subject (e.g., USP, LSP1, LSP2), on a skull, nose, or face surface of the subject 100 opposite a portion of an eyeglasses physiological sign monitoring portion 1620 (e.g., FIG. 16), and/or other alternative relevant subject body location suitable for sensing relevant physiological and/or environmental parameters, generating respective electronic signals based on such monitored parameters, determining relevant physiological and/or environmental signs, and/or generating machine-readable and/or human-readable values indicative of such physiological and/or environmental signs, such as, for example, photoplethysmogram, electrocardiogram, ballistocardiogram, skin temperature, ambient temperature, blood oxygen saturation, electrical potential, skin conductance, skin resistance, altitude, humidity, UV index, body temperature, heart rate, ECG pulse rate, pulse deficit, premature ventricular complexes, ambient light, respiratory rate, blood pressure, head motion, neck motion, general motion, orientation, geolocation, audio, biometric, liquid (e.g., blood), mean arterial blood pressure, systolic blood pressure, diastolic blood pressure, R-J interval, cranial temperature, heart rate variability, pulse transit time, pulse wave velocity, pacemaker edge detection, R-R interval, stroke volume, heart rate, cardiac output, ventricular ejection time, pre-ejection period, maximal oxygen uptake, galvanic skin response, hydration level, stress level, bioimpedance, glucose level, subject activity level, coughing, sneezing, blood, arterial characteristics, and/or end-tidal carbon dioxide content.

In various embodiments, at least a portion of enhanced monitoring device 140 (not shown) may be configured to be deployed in or as a variety of form factors such as, for example, a helmet, glasses, headsets, hats, around the ear devices, over the ear clips, headbands, jewelry, earrings, scarfs, necklaces, hearing aids, etc.

For example, referring now to FIG. 16, a perspective view of an example of a physiological sign portion of an enhanced monitoring device according to some embodiments of the present disclosure is provided. In various embodiments, a second physiological sign portion 120 of enhanced monitoring device 140 may be deployed in eyeglasses 1620. In various embodiments, eyeglasses physiological sign portion 1620 may include a plurality of physiological sensors such as, for example, one or more ECG sensors (e.g., 121) and an electrooculography (EOG) sensor 1628. In some embodiments, the plurality of physiological sensors eyeglasses physiological sign portion 1620 may include one or more ECG sensors (e.g., 121), an EOG sensor 1628, a sweat chemistry/composition sensor (e.g., 116), a skin temperature sensor (e.g., 126), a motion sensor (e.g., 122), and/or a skin conductance and resistance sensor (e.g., 129). In various embodiments, the electronic signal values of physiological sensors in eyeglasses physiological sign portion 1620 may add to the electronic signal values of physiological sensors in a plurality of other physiological sign monitoring portions (e.g., 110, 120) deployed on, for example, two or more surfaces of a surface on the back of an ear of the subject 100, a surface over a mastoid region of the subject 100, and a surface over another region of the neck of the subject 100, to provide a super set of physiological sign values.

In various embodiments, one or more ECG sensors (e.g., 121) of eyeglasses physiological sign portion 1620 may be deployed in one or more arms of the eyeglasses and, for example, where the arms of the glasses bend for securing along the skull and the top of the ears of a subject 100, and may accordingly be configured for deployment on a surface on the back and top of an ear of the subject, or on a corresponding skull surface of a subject. In various embodiments, one or more ECG sensors (e.g., 121) of eyeglasses physiological sign portion 1620 may be deployed in one or more nose pads of the eyeglasses, and may accordingly be configured for deployment on a surface on the nose of a subject opposite the nose pads. The inventor has determined that deploying one or more ECG sensors (e.g., 121) in eyeglasses physiological sign portion 1620, and other ECG sensors (e.g., 111) in first physiological sign portion 110, may remove limitations on ECG sensitivity described herein. In some embodiments, the one or more ECG sensors (e.g., 121) of eyeglasses physiological sign portion 1620 may include corresponding ECG electrodes. In various embodiments, the one or more ECG sensors (e.g., 121) of eyeglasses physiological sign portion 1620 are also configured to collect skin temperatures (e.g., combined ECG sensor 121-skin temperature sensor 126) from one or more touchpoint surfaces on a subject's 100 head. In various embodiments, the eyeglasses physiological sign portion 1620 is configured to provide clean ECG waveform signals, EOG waveform signals, and skin temperature signals.

In various embodiments, eyeglasses physiological sign portion 1620 may include a multi-point (e.g., 3-point) EOG sensor 1628 on the bridge of the eyeglasses that is configured to monitor eye movements of a subject 100. As is known in the art, eye movements are controlled by the six extrinsic muscles of each eye; these muscles allow the eyes to track moving objects or to fixate on a stationary object while a subject's 100 head moves, and to interpret these activities as electrical signals. As is known in the art, electrooculography is a method for sensing eye movement and is based on recording the standing corneal-retinal potential arising from hyperpolarizations and depolarizations existing between the cornea and the retina, e.g. EOGs. This potential can be considered as a steady electrical dipole with a negative pole at the fundus and a positive pole at the cornea. The inventor has observed that the standing potential in the eye may be estimated by measuring as the eye-gaze changes, thus obtaining the EOG (measurement of the electric signal of the ocular dipole). In various embodiments, EOG sensor 1628 is configured to record these electrical signals as an electrooculogram (EOG) waveform.

The inventor has determined that the EOG values monitored by EOG sensor 1628 may vary from 50 to 3500 µV with a frequency range of about DC-100 Hz. The inventor has also determined that the behavior of EOG values monitored by EOG sensor 1628 is practically linear for gaze angles of ±30 degrees and changes approximately 20 µV for each degree of eye movement. The inventor has further determined that the variability of EOG values monitored by EOG sensor 1628 depends on many factors (e.g., electromyography (EMG) potentials), and that determining the level of perturbations in the eyes corresponds to EMG potentials in the head and face of a subject 100, and provides electrical signal data to clean up ECG signals provided from one or more ECG sensors (e.g., 121) of enhanced monitoring device 140. The inventor has determined that using an AC high-gain differential amplifier (1000-5000), together with a high-pass filter with cut-off frequency at approximately 0.05 Hz and a relatively long time constant, a low pass filter with cut-off frequency at approximately 35 Hz, and a signals sampling rate of 100 times/s or more, has been shown to overcome this variability. The inventor has observed that other eye movements, including gaze, pupil dilation, blinking, head movements, lighting conditions, and other eye features, are indicative of mood, stress, fatigue, concentration, and external environmental variables. In various embodiments, EOG sensor 1628 is configured to monitor eye muscle movements/potentials, gaze, pupil dilation, blinking, head movements, lighting conditions, and other eye features. In various embodiments, EOG sensor 1628 communicates electrical signal data to biometric subsystem (e.g., 134).

In various embodiments, eyeglasses physiological sign portion 1620 may include one or more environmental sensors (e.g., 135), a location subsystem (e.g., 132), and audio input/output subsystem (e.g., 133), a biometric subsystem (e.g., 134), an RFID subsystem (e.g., 136), a liquid subsystem (e.g., 137), a communications interface subsystem (e.g., 139), a processor (e.g., 142), a memory (e.g., 143), and/or a power subsystem (e.g., 138). In various embodiments, a power subsystem (e.g., 138) of eyeglasses physiological sign portion 1620 may include a battery 1638 (e.g., a rechargeable lithium ion battery), a power and data delivery interface 1652 (e.g., a charging micro USB port), and a power button 1601. In various embodiments, an indicator subsystem of eyeglasses physiological sign portion 1620 may include a system LED. In various embodiments, eyeglasses physiological sign portion 1620 may exchange signals with another physiological sign monitoring portion of enhanced monitoring device 140 (e.g., with first physiological sign monitoring portion 100, with another second physiological sign monitoring portion 120) via a wired connection or via wireless communications. For example, eyeglasses physiological sign portion 1620 may be configured to be connected to another physiological sign monitoring portion of enhanced monitoring device 140 via electromechanical interconnect 105 and via an interface in the respective arm of eyeglasses 1620 (e.g., left arm, right arm) that is on the same side of subject 100 where the other physiological sign portion is configured to be deployed. In various embodiments, eyeglasses physiological sign portion 1620 includes a communications interface (e.g., 139, FIG. 4) and is configured to communicate wirelessly (e.g., via Bluetooth LE, near field magnetic induction, and/or another suitable low-power wireless communication standard protocol) with another physiological sign monitoring portion of enhanced monitoring device 140.

Figure 5:
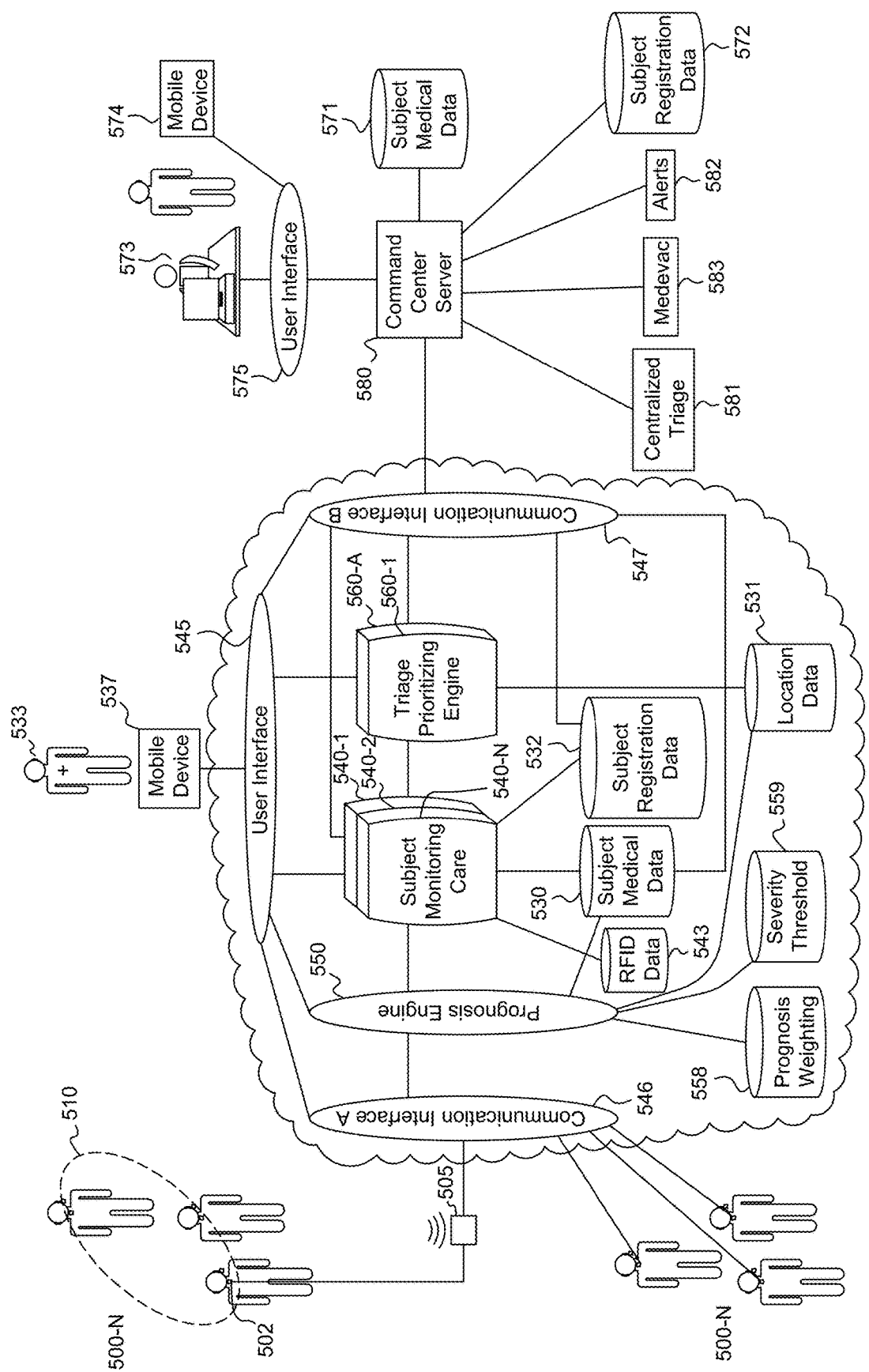
FIG. 5 is a block diagram of an example of a system for remote physiological monitoring of subjects, and for automated triage prioritization, according to some embodiments.

Various embodiments of the present disclosure provide a networked environment as shown in FIG. 5 that includes a plurality of monitoring devices deployed on a plurality of subjects 500-N, one or more mobile communication and display devices in communication over a first network (e.g., a Bluetooth network) with the plurality of monitoring devices via communications interface A 546 and in communication with a central command center over a second network (e.g., a wireless network) via communications interface B 547. In various embodiments, mobile communication and display device 537 may include any suitable device such as, for example, a laptop, a personal computer, a smart phone, a smart watch, a personal digital assistant, a cellular phone, a tablet, an electronic personal planner, a slate tablet, a booklet computer, a convertible notebook, a phablet, a command and control system having a common operational picture (COP) or other situational awareness display, a human-wearable computing device, etc. In various embodiments, mobile communication and display device 537 operates an application (e.g., a software application, web application, native application, or mobile application) that is configured to display via user interface 545, a triage-prioritized list of one or more subjects' physiological signs by severity, subject descriptive data, subject and user (e.g., medic, EMT, first responder) geolocation data, monitoring device registration and binding to subject, alerts/ messaging/notification features, and/or various customization options. In various embodiments, an application operating on mobile communication and display device 537 displays a record for each subject 500-N via user interface 545 and subject monitoring core 540-N, including, for example, identifying information for the subject 500-N, identifying information for the corresponding monitoring device (140), gender, age, medical records, fitness records, photos, videos, descriptive data, geolocation, prognosis scores, triage prioritization order, and available physiological signs data (e.g., as provided by, and/or determined from, respective electronic signals generated by physiological sensors in first 110 and second 120 physiological sign portions of enhanced monitoring device 140 deployed on respective, different surfaces of subject 500-N). In various embodiments, one or more of the features of the central command center (e.g., command center server 580, subject medical data 571, subject registration data 572, etc.) may be accessed by the one or more mobile communication and display devices, and one or more computing devices (e.g., device 573, mobile device 574) of the central command center, over a cloud computing network. The one or more mobile communication and display devices 537 may include a mobile application or software application operating on the one or more mobile communication and display devices and including multiple blocks of logical software cores referred to as subject monitoring cores (denoted subject monitoring cores 550-1, 550-2, . . . , 550-N; these may be referred to collectively as "subject monitoring cores 550") and various software modules operating in a networked environment including a user interface 545, a prognosis engine module 550, triage prioritizing engine 560-A, that provide real-time, in-memory collection and analysis of generated and cached respective machine readable values corresponding to respective physiological parameters of subjects 500-N, respective environmental parameters around such subjects, respective physical parameters (e.g., location, orientation) of such subjects, respectively monitored in real-time by corresponding monitoring devices 140, to generate respective prognosis scores for each of the monitored subjects, and a triage prioritization order for the monitored subjects, based on complex algorithms, predetermined severity thresholds, predetermined prognosis weighting factors, and the generated machine readable values, the cached machine readable values, and to display, and/or change a display, of generated respective human readable values for a predetermined number of subjects on respective portions of user interface 545 based on the generated triage prioritization order.

In various embodiments, prognosis weighting factor module 558, and/or severity threshold module 559, receive, retrieve, and store in memory, respective prognosis weighting factors (e.g., pain index, predetermined sound type (e.g., scream) detection, blood or liquid detection, heart beat issues, breathing issues, greater than a predetermined percentage of confidence in prognosis (e.g., 95%, 90%, 75%), intelligence alerts, etc.), and/or respective severity thresholds (e.g., high and/or low thresholds for pulse oximetry, respiratory rate, heart rate, skin temperature, body temperature, mean arterial blood pressure, systolic blood pressure, diastolic blood pressure, R-J interval, cranial temperature, heart rate variability, pulse transit time, pulse wave velocity, pacemaker edge detection, R-R interval, stroke volume, heart rate, respiratory rate, ECG pulse rate, pulse deficit, cardiac output, ventricular ejection time, pre-ejection period, premature ventricular complexes, maximal oxygen uptake, end tidal carbon dioxide, galvanic skin response, hydration level, stress level, bioimpedance, glucose level, subject activity level, coughing, sneezing, arterial characteristics, monitoring device remaining battery capacity, distance between subject and user, a plurality of subject orientations, monitoring device signal strength, etc.). In various embodiments, prognosis weighting factors and/or severity thresholds are predetermined. In various embodiments, predetermined prognosis weighting factors and/or severity thresholds are dynamically updated based on, for example, inputs from a user (e.g., medic, EMT, physician, first responder) 533 accessing the system via user interface 545, inputs from a remote administrative or medical user (e.g., 573, 574) accessing the system via user interface 575 and communications interface B 547, environmental parameters detected and/or transmitted to the mobile communication from one or more monitoring devices, intelligence (e.g., HUMINT, SIGINT, ELINT, FMV, Automatic Identification System (AIS) inputs) alerts received by a mobile communication and display device via communications interface B 547 (e.g., from a command center server 580), subject medical data (e.g., 530, 571), etc. In various embodiments, a weather module (not shown) may receive real-time environmental parameters (e.g., ambient pressure, ambient temperature, humidity, UV index, altitude), and, for example, real-time location data, from a plurality of enhanced monitoring devices (140) deployed on a plurality of subjects 500-N, and provide real-time, accurate weather forecasting at locations specific to each of the plurality of subjects 500-N.

In various embodiments, RFID data module 543 receives, retrieves, and stores in memory, RFID data (or bar code, QR code, or other device identifying data) from one or more enhanced monitoring devices via communications interface A 546, via an RFID (or bar code, QR code, or other device identifier) reader of, or in serial communication with, mobile communications and display device. In various embodiments, location data module 531, receives, retrieves, and stores in memory, location data (e.g., GPS coordinates) of the mobile communication and display device 537, subject location data (e.g., GPS coordinates, compass heading and motion) received from one or more monitoring devices via communications interface A 546, and/or locations of nearby and local medical facilities, hospitals, bases, and any and all other pertinent geolocation values. In various embodiments, subject medical data module 530 receives, retrieves, and stores in memory, historical medical data (e.g., data in electronic medical records, data in medical history, prior physiological parameters, orientation, etc. received via communications interface A 546 from monitoring device(s) deployed, medical data received via communications interface B 547 such as from subject medical data 571, subject descriptive (e.g., photos, videos, age, gender, height, weight, hair, eye color, race, body type, body size, text-based visual description, and any known identifying features such as scars or tattoos) data received via communications interface B 547 (e.g., subject medical data 571), via a camera (e.g., photo, video) of, or in communication with (e.g., serial, over communications interface A 546), mobile communications and display device 537, and/or via user interface 545 regarding subject 500-N, and/or more subjects. In various embodiments, subject registration data module 532 receives, retrieves, and stores in memory, registration information binding respective monitoring devices (e.g., QR code, RFID, unique identification strings, bar code, pseudorandomly generated value, or other suitable unique identifying information) to respective subjects 500-N (e.g., subject name, social security number, date of birth, pseudorandomly generated value, or other suitable unique identifying information). In various embodiments, a pseudorandomly generated value is generated using, for example, a C RAND or RAND_S function, a PHP hypertext preprocessor function microtine or mt_rand, an Unix function/dev/random, a Java function SecureRandom, an Open SSL RAND_screen( ) function, or other suitable function, to return a pseudorandom sequence with a period long enough so that a finite sequence of reasonable length is not periodic and with an information entropy that is high enough to resist a brute force attack by a cryptanalyst. In various embodiments, a pseudorandomly generated value is generated using, for example, a secret key, or seed, to set the initial state of the pseudorandom sequence generator, a combination of the seed and, for example, a counter output, to provide an input to a hash function such as, for example, MD5 or SHA-1, to increase cryptographic security in the generated pseudorandom sequence.

Mobile communication and display device 537 may also include a forensics module for recording, reporting, tuning, and playback of collected data (e.g., RFID Data 543, subject medical data 530, 571, location data 531, prognosis scores, triage prioritization orders, severity scores, audio data (e.g., received from microphone of a portion (e.g., second physiological sign portion 120) of enhanced monitoring device 140), etc.). In some embodiments, forensics module may store recorded data in a non-transitory, tangible machine readable storage medium. The non-transitory, tangible storage medium can be a non-transitory computer readable storage medium. The computer readable medium can be a machine-readable storage device, a machine-readable storage medium, a memory device (e.g., flash or random access memory), a hard disk drive, a tape drive, an optical drive (such as, but not limited to CDROM, DVD, or BDROM) or the like, or a combination of one or more of them. In various embodiments, forensics module stores RFID Data 543, subject medical data 530, 571, location data 531, audio data, prognosis scores, triage prioritization orders, and/or severity scores, in persistent storage. In various embodiments, forensic module manages playback operations such that stored data is provided as an input to prognosis engine and/or triage prioritization engine to perform all or some of the functions described herein for data received from monitoring devices for subjects 500-N. In various embodiments, forensic module manages playback operations and permits users to speed up or slow down playback of the stored data. For example, forensic module may manage playback operations to permit a user to visually review 6 months of stored data via user interface 545, 575 in a significantly shorter period of time such as 6 hours or 60 minutes. In some embodiments, results based on using stored data provided by forensics module may be used by a user to perform trend analysis, after-action reports, revise prognosis weighting and/or severity thresholds for a respective subject, and/or revise or update a subject's medical history, such that the prognosis weighting factors, severity thresholds, and subject medical data (530, 571) can be further optimized. In some embodiments, a user may use data and trends provided by operations managed by forensics module to build up a knowledge base of information. In various embodiments, forensics module enables artificial intelligence services which are configured to learn from past data sets with known outcomes and prognoses and which may automatically modify severity thresholds and/or prognosis weighting factors.

Although three subject monitoring cores, and two triage prioritizing engines, are shown in this illustrated example, any number of subject monitoring cores, and triage prioritizing engines, may be used. Operational personnel 533 (e.g., medics, EMTs, first responders, physicians, fitness supervisors) may access the prognosis engine 550, subject monitoring core 540-N, and/or triage prioritizing engine 560-A, via the user interface 545. In various embodiments, operational personnel 533 may access other modules (e.g., forensics module (not shown), RFID data module 543, subject medical data module 530, subject registration data module 532, prognosis weighting factor module 558, severity threshold module 559, location data module 531, etc.) via the user interface 545.

Figure 6:
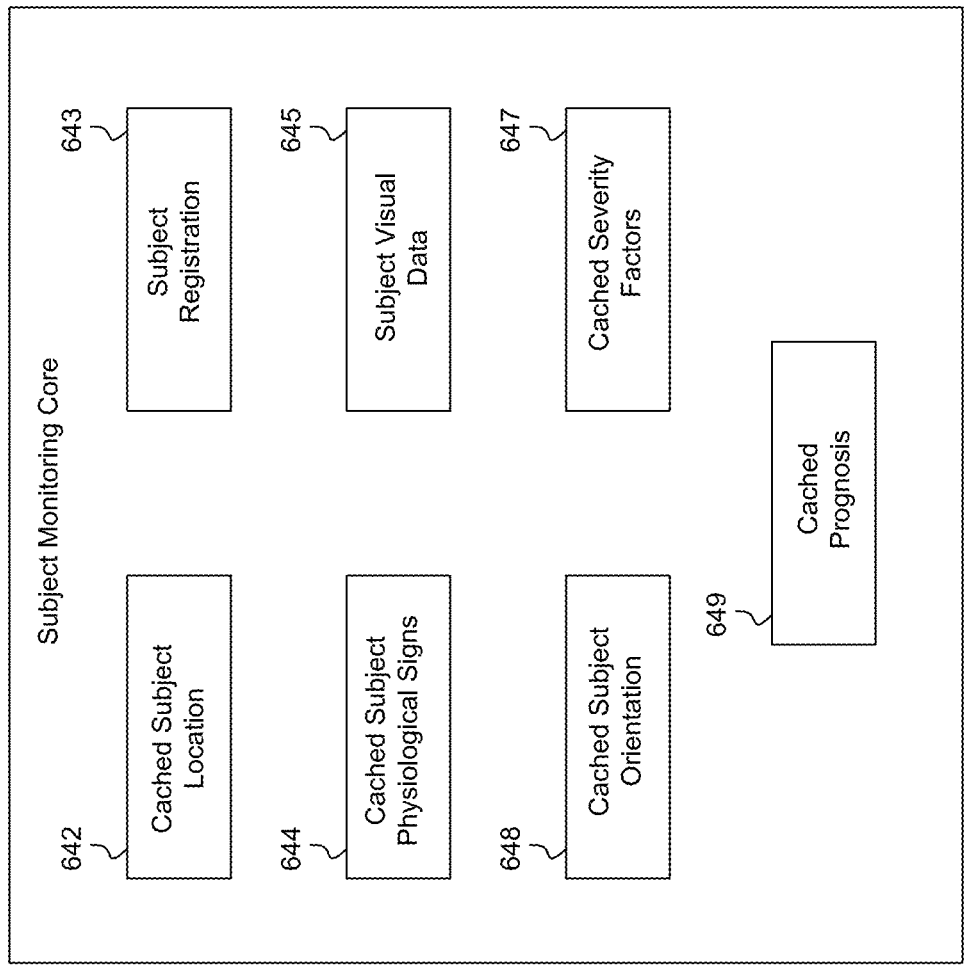
FIG. 6 is a block diagram of an example of a subject monitoring core of a mobile communication and display device in accordance with some embodiments of the present subject matter.

FIG. 6 shows an example of a subject monitoring core 550-N that includes location 642 of subject 500-N cached in memory of a mobile communication display device (e.g., RAM, in-memory data grids, retrieved from location data module 531, in-memory database (e.g., IMDB, MMDB, memory resident database, etc.)), physiological signs 644 for subject 500-N cached in memory of a mobile communication display device (e.g., RAM, in-memory data grids, retrieved from subject medical data module 530, in-memory database (e.g., IMDB, MMDB, memory resident database, etc.)), orientation 648 for subject 500-N cached in memory of a mobile communication display device (e.g., RAM, in-memory data grids, retrieved from orientation data module (not shown), in-memory database (e.g., IMDB, MMDB, memory resident database, etc.)), registration 643 for subject 500-N stored in memory of a mobile communication display device (e.g., RAM, ROM, in-memory data grids, retrieved from subject registration data module 532, NoSQL database, in-memory database (e.g., IMDB, MMDB, memory resident database, etc.)), visual data for subject 500-N stored in memory of a mobile communication display device (e.g., RAM, ROM, in-memory data grids, retrieved from subject medical data module 530, NoSQL database, in-memory database (e.g., IMDB, MMDB, memory resident database, etc.)), severity scores (e.g., pulse oximetry, respiratory rate, heart rate, skin temperature, body temperature, mean arterial blood pressure, systolic blood pressure, diastolic blood pressure, R-J interval, cranial temperature, heart rate variability, pulse transit time, pulse wave velocity, pacemaker edge detection, R-R interval, stroke volume, heart rate, respiratory rate, eye movement, ECG pulse rate, pulse deficit, cardiac output, ventricular ejection time, pre-ejection period, premature ventricular complexes, maximal oxygen uptake, end tidal carbon dioxide, galvanic skin response, hydration level, stress level, bioimpedance, glucose level, subject activity level, coughing, sneezing, arterial characteristics, corresponding monitoring device remaining battery capacity, distance between subject and user, a plurality of subject orientations, corresponding monitoring device signal strength, etc., severity scores) for subject 500-N cached in memory of a mobile communication display device (e.g., RAM, in-memory data grids, retrieved from prognosis engine 550, in-memory database (e.g., IMDB, MMDB, memory resident database, etc.)), prognosis scores for subject 500-N cached in memory of a mobile communication display device (e.g., RAM, in-memory data grids, retrieved from prognosis engine 550, in-memory database (e.g., IMDB, MMDB, memory resident database, etc.)).

In various embodiments, a mobile communications and display device 537 includes one or more network switches, and/or encryption switches, memory (e.g., active memory 1122 (FIG. 11), which may include a persistent storage unit (e.g., NoSQL, MySQL cluster, database), a distributed working memory (e.g., software running on processor 1120 (FIG. 11) and including a plurality of in-memory data grids such as, for example, a distributed R-tree index, Quadtree index, Rete diagram, Gna tree, Octree, Grid, Z-order, timesplit B-tree, multi-version B-tree, etc., architecture in memory, in-memory database (e.g., IMDB, MMDB, memory resident database, etc.)), processor (e.g., 1120 (FIG. 11)) running the distributed working memory software and communicating with user interface module 545 via an object-oriented data interchange format such as, for example, JavaScript Object Notation (JSON) and providing, for example, NoSQL, MySQL cluster, persistence. In various embodiments, processor (e.g., 1120 (FIG. 11)) of mobile communication and display device stores instructions in a non-transient, tangible machine readable storage medium. The non-transient, tangible storage medium can be a non-transient computer readable storage medium. The computer readable medium can be a machine-readable storage device, a machine-readable storage medium, a memory device (e.g., flash or random access memory), a hard disk drive, a tape drive, an optical drive (such as, but not limited to CDROM, DVD, or BDROM) or the like, or a combination of one or more of them.

Referring again to FIG. 5, the user interface module 545 provides an interface between users 533 (e.g., medics, EMTs, physicians, first responders, fitness supervisors), the functionality of the mobile communication and display device, data received from the plurality of monitoring devices deployed on subjects 500-N via communications interface A 546 and over a first network (e.g., a Bluetooth network), and data received from a command center server 580 via communications interface B 547 and over a second network (e.g., a wireless network, the Internet, a cloud computing network (e.g., a public or secure cloud), etc.). In various embodiments, the user interface 545 is a representational state transfer (REST) application programming interface (API) based on a JSON model to provide access to many types of clients (e.g., thick and thin clients, mobile device clients). In various embodiments, user interface module 545 provides a Web-based interface (e.g., via a web-based application) to interface with command center server 580. In various embodiments, user interface 545 provides platform/device independent visualization. In various embodiments, user interface 545 provides portal services to many types of clients to interface with command center server 580. In various embodiments, user interface module 545 includes web services to interface with command center server 580. In various embodiments, user interface module 545 provides a command driven interface (e.g., DOS, Linux, etc. command driven interface) to interface with command center server 580. The user interface module 545 can include a portal to interface with command center server 580. In various embodiments, suitable secure communication techniques may be utilized to communicate data between over the first and/or second network such as, for example, secure communication methods employing asymmetric or symmetric encryption techniques, message authentication codes, secure hashing algorithms, or combinations thereof using, for example, a network security protocol such as, for example, SSL or TLS.

Referring back to FIG. 5, mobile communication and display device 537 includes communication interface A 546 communicating with monitoring devices deployed on subjects 500-N (and/or monitoring device hub 502, relay devices 505) and communications interface B 547 communicating with one or more command center servers 580. Communications interface modules 546, 547 allow software and data to be transferred between monitoring devices deployed on subjects 500-N, one or more command center servers 580, various modules of mobile communication and display device 537, and/or external devices including, for example, devices associated with external sensors, external readers, and/or external assets (e.g., MEDEVAC, CASEVAC assets). In various embodiments, communications interface modules 546, 547 provide machine-to-machine (MTM) communications such as, for example, in an Internet of Things (IoT) infrastructure. In various embodiments, communications interface modules 546, 547 provide indications (e.g., notifications, communications, and/or signals) to external devices (e.g., via command center server 580, alerts 582, other mobile communications and display devices, etc.) based on specifications predefined for prognosis engine 550, triage prioritizing engine 560-A, subject monitoring core 540-N, Medevac 583, Alerts 582, etc., for a subject 500-N and when prognosis engine 550, triage prioritizing engine 560-A, subject monitoring core 540-N, provides an indication that an event has been identified and/or triggered. In various embodiments, such as, for example, for government and/or military applications, communications interface B 547 module may include a satellite or RF radio, such as, for example, military radios, including via a Single Channel Ground and Airborne Radio System (SINCGARS), and/or NASA MGRS-compliant communications. In various embodiments, such as, for example, for commercial applications, communications interface B 547 module may include a connection such as, for example, a Wi-Fi, Ethernet, analog phone, or digital leased line networking connection.

Examples of communications interface modules 546, 547 can include a modem, Ethernet card, wireless network card, a Personal Computer Memory Card International Association (PCMCIA) slot and card, or any suitable network interface module. Software and data transferred via communications interface communications interface modules 546, 547 can be in the form of signals, which can be electronic, electromagnetic, optical, or the like that are configured to being received by communications interface communications interface modules 546, 547. These various types of signals are collectively referred to herein as electronic signals. These electronic signals can be provided to communications interface modules 546, 547 via a communications path (e.g., channel), which can be implemented using wire, cable, fiber optics, a telephone line, a cellular link, a radio frequency (RF) link, a satellite link, a Bluetooth link, and other communication channels.

In various embodiments, a plurality of monitoring devices for a plurality of subjects 500-N can simultaneously connect wirelessly to mobile communication and display device 537 via communications interface A 546. In various embodiments, one or more monitoring devices (e.g., enhanced monitoring device 140) may be configured to act as a monitoring device hub 502 in which a plurality of monitoring devices (e.g., plurality of enhanced monitoring devices 140, combination of one or more enhanced monitoring devices 140 and other monitoring devices (including, for example, monitoring devices described in U.S. patent application Ser. Nos. 16/593,354, 15/889,992, 14/812,696 which are incorporated by reference herein in their entirety)) in communication range of each other form an ad hoc network 510 (e.g., an ad hoc mesh network). In various embodiments, the monitoring device hub 502 in such an ad hoc network 510 may be configured to receive respective electronic signals based on respective monitored physiological parameters of respective subjects from each of the other monitoring devices in the ad hoc network. In various embodiments, the monitoring device hub 502 communicates the aggregated electronic signals to a mobile communication and display device 537 over a first network via communications interface A 546. In various embodiments, a secure (e.g., encrypted) wireless connection between a monitoring device and a mobile communication and display device 537, monitoring device hub 502, and/or relay network device 505 (e.g., beacon), securely identifies the respective monitoring device to the mobile communication and display device 537, monitoring device hub 502, and/or relay network device 505. In various embodiments, the system including monitoring device and a mobile communication and display device 537, monitoring device hub 502, and/or relay network device 505, is configured to search for and change transmission frequencies on the monitoring device and a mobile communication and display device 537, monitoring device hub 502, and/or relay network device 505, due to interference or prohibitive/denied electromagnetic environment by using a randomized, but previously synchronized algorithm that defines a set of transmission frequencies to cycle through. In various embodiments, relay network device 505 can be used to receive and rebroadcast monitoring device transmissions to mobile communication and display device 537. In various embodiments, relay network device 505 may be, for example, a battery or externally powered mobile device that may receive monitoring device transmissions, cache them in memory, and then submit them to a configured application (e.g., a mobile application) for display on relay network device. In various embodiments, including a relay network device 505 in the system increases the range of the system to any environment where a network connection (e.g., intranet, Internet) can be made via Wi-Fi, cellular connectivity, satellite connectivity, or any other IP or similar connectivity of relay network device 505. In various embodiments, relay network device 505 includes a mechanism such as, for example, via on-screen displays and/or lights, to signal the strength of other relay network devices (not shown) in a surrounding area of the relay network device 505 to enable comprehensive coverage for an installation. In various embodiments, relay network device 505 is a search and rescue drone dispatched to a remote region with a plurality of subjects 500-N wearing monitoring devices. The inventor has identified that the systems and methods described herein and including a relay network device search and rescue drone 505 permits search and rescue operators to determine the condition of casualties before dispatching costly operations (including medical personnel) into remote (and possibly actively hostile) locations. In various embodiments, a plurality of relay network nodes (not shown) may redundantly work in parallel, each caching a complete set of monitoring device data transmissions to be transmitted when either the addressed, appropriate mobile communication and display device 537 or a new, replacement mobile communication and display device 537 becomes available via the relay network. In various embodiments, a plurality of relay network nodes (not shown) includes a series of relay network devices (not shown) configured to authenticate with, and receive data from, a plurality of monitoring devices that may be centrally aggregated and presented for either global or localized views of subjects on an application (e.g., mobile application, native application) running on one or more mobile communication and display devices 537, and/or an application running on one or more remote computing devices (573, 574). For example, in a disaster scene (e.g., a natural disaster such as a tsunami, tornado, etc., a man-made disaster such as a mass shooting, structure fire, etc.), the first responders, EMTs, fire fighters, police, and any other emergency personnel will have varying equipment that will saturate the available bandwidth and also complicate the logistics of centralizing the data from disparate devices. The inventor has determined that the enhanced monitoring devices, systems, and methods described herein permit smaller cells of devices to communicate in their immediate vicinity, interconnect the devices within such cells, and handle the long-range communications to an intranet or the Internet. The inventor has determined that the enhanced monitoring devices, systems, and methods described herein serve to both extend the range of emergency devices and extend the capabilities of emergency management consoles and devices (e.g., 545, 537, 575, 573, 574). The inventor has determined that repeater devices described herein (e.g., 505) reduce the number of wireless connections handled by the user devices and simply feed such devices the data of the emergency devices (e.g., enhanced monitoring devices, other electronic devices used for evaluating, triaging, servicing, treating, helping, and surveying a disaster area, emergency medicine area, any area of distress, or any area with a gathering of people, etc.), effectively giving them an unlimited number of virtual connections. In various embodiments, each enhanced monitoring device (140), and/or a separate external subject notification device, deployed on the subject (500-N), communicated with mobile communication and display device 537 directly, or indirectly via one or more relay network devices (not shown), and notifies the respective subject (500-N) such as, for example, by vibrations, flashing lights, auditory sounds, etc., as to the status of communications between the enhanced monitoring device (140) deployed on the subject and a mobile communication and display device 537.

In various embodiments, centralized triage 581 is a logical representation of a centralized triage station including one or more physicians/specialists, a hospital or second-level care facility, an ambulatory facility, or other suitable facility, where one or more subjects 500-N are transferred to via MEDEVAC, CASEVAC, or other suitable transportation services (e.g., ambulance), and where medical data, location data, registration data, orientation data, etc., regarding such subjects (e.g., stored in subject medical data module 530, subject registration data module 532, subject location data module 531, subject orientation data module 531, etc.) is transferred via communications interface B 547 and made accessible to users (e.g., 573, 574) at such facilities (e.g., ambulatory service, emergency room, operating room) via user interface 575. In various embodiments, Medevac 583 is a logic representation of the logistics of ambulatory services (e.g., via MEDEVAC, CASEVAC, Ambulance, etc.) that the system may assign to various, disparate medical facilities based on, for example, their facilities and their current patient loads. Command Center server 580 and services from Command Center server 580 (e.g., Centralized triage 581) are readily scalable. For example, in various embodiments, a building/community/city/county/district/state/nation/global (e.g., for a mass casualty event) may be organized with each separate municipality having continuous monitoring of subjects 500-N in a respective region of concern fed into respective command center servers 580 with coordinating the control, logistics, and dispatch of Medevac 583 services when help was predicted/seen to be needed and the assignment of healthcare services/beds/personnel to treat such subjects. In various embodiments, user interface 575 may provide a selectable and scalable view of regional activity (e.g., subjects, medics, medevacs) such as, for example, building, municipality, city, county, district, state, nation, global including to provide command and control for mass casualty events. Command center server 580 services are also readily accessible as a centralized software-as-a-service platform. In various embodiments, each entity receiving access to command center server 580 services (e.g., hospital, second-level care facility, ambulatory facility, municipality etc.) may subscribe to such services and, for example, pay a subscription fee to have centralized medical personnel available to assist with their triage and patient monitoring. In various embodiments, subjects, either through the subscription of a service or through the conscription of an organizational entity, would either wear an enhanced monitoring device at all times, or during specific times, or for spot-checking purposes. In various embodiments, data from this monitoring may be transmitted to a centralized repository (e.g., respective subject monitoring core, command center server) for analysis. In various embodiments, if analysis suggested that a particular subject needed medical attention from their short- or long-term physiological signs data, and/or from motion, orientation, and/or environmental data, that suggested an injury, a slip and fall, or other situations that require medical intervention, then the subject may be contacted by a user (e.g., 533, 573) and by voice (e.g., via communication interface 546 and audio in/out 133 (FIG. 4)) or electronic communication to either setup a doctor's visit, come into an urgent care, or to have an ambulance summoned to bring them to the hospital. In various embodiments, the lack of the ability to communicate with the subject, when data suggests a medical situation is imminent or currently in-progress, may also prompt an ambulance (e.g., 583) summons.

Referring again to FIG. 5, the user interface module 545 provides an interface between users 533 (e.g., medics, EMTs, physicians, first responders, fitness supervisors), the functionality of the mobile communication and display device, data received from the plurality of monitoring devices deployed on subjects 500-N via communications interface A 546 and over a first network (e.g., a Bluetooth network), and data received from a command center server 580 via communications interface B 547 and over a second network (e.g., a wireless network, the Internet, a cloud computing network (e.g., a public or secure cloud), etc.). In various embodiments, the user interface 575 is a representational state transfer (REST) application programming interface (API) based on a JSON model to provide access to many types of clients (e.g., thick and thin clients, mobile device clients, desktop clients). In various embodiments, user interface module 575 provides a Web-based interface (e.g., via a web-based application) to interface with command center server 580. In various embodiments, user interface 575 provides platform/device independent visualization. In various embodiments, user interface 575 provides portal services to many types of clients to interface with command center server 580. In various embodiments, user interface module 575 includes web services to interface with command center server 580. In various embodiments, user interface module 575 provides a command driven interface (e.g., DOS, Linux, etc. command driven interface) to interface with command center server 580. The user interface module 575 can include a portal to interface with command center server 580. In various embodiments, centralized triage 581 provides a portal for a centralized triage group (e.g., one or more physicians/specialists) to enable users of the centralized triage group to review, override, or alert a user of a mobile communication and display device to evaluated changes in prognoses for subjects' monitored by monitoring devices communicating with the mobile communication and display device. In various embodiments, centralized medical personnel can interface with command center server 580 via user interface 575 to review subject data in real-time, review active subjects data in real time and receive subject trend and pattern analysis, connect to, review and annotate subjects' electronic records, edit subjects' medical information, add notes to subjects' medical records, add notes to subjects' fitness records, annotate prognoses for subjects, produce instant after action reports (AAR) from data collected, send instructions and alerts to subjects' medics, EMTs, first responders at a respective mobile communication and display device, and/or initiate two-way communications via voice, text, video, e-mail, or any suitable communication technique, with patients' medics, EMTs, first responders at a respective mobile communication and display device.

In various embodiments, Alerts 582 is a logical representation of the notes, instructions, records, and delivery, notification and messaging features of the system. In various embodiments, an alert can be provided based on, for example, a prognosis score and/or triage prioritization order (e.g., alert provided to a user display via user interface 545, 575). In various embodiments, a notification message based on the prognosis score and/or triage prioritization order can be transmitted (e.g., to an external device via communications interface B module 547). Any suitable notification message can be provided and is based on a user's definitions provided for the prognosis or triage prioritization order. In some embodiments, the notification message is a default notification message set by, for example, the administrator 573, 574. For example, the notification message transmitted via communications interface module B 547 can be an electronic mail message, a telephone call, an alphanumeric page, a numeric page, a text message, a short messaging service message, a video message, a voice message, and other suitable notification messages. In various embodiments, a command center is a logical representation of functions provided by an administrative user. In various embodiments, command center server 580 provides an administrative and medical role portal into the system and may be integrated with operational command centers. In various embodiments, an administrative user may develop an operational environment for the system, review medic/EMT/first responder and subject data and geolocations in real-time, annotate medics' and subjects' electronic records, edit subjects' medical information, add notes to subjects' medical records, add notes to subjects' fitness records, send instructions and alerts to subjects' medics, and initiate two-way communications via voice, text, video, email, or any suitable communication technique with subjects' medics, via user interface 575. For example, during combat operations, command center server 580 (Medevac 583), and administrative and/or medical role personnel interfacing with such server, can provide instructions to direct subjects 500-N to one of a plurality of operating posts with medical facilities depending on bed space, capabilities, and personnel. For example, during situations such as, for example, a natural disaster or mass casualty event, command center server 580 (Alerts 582), and administrative and/or medical role personnel interfacing with such server, may receive real-time notifications with respective prognosis scores and triage prioritization of various subjects, and may monitor and/or transmit instructions to direct/monitor the subjects' movement from the point of injury to the next level of care.

In various embodiments, command center server 580 and subject medical data 571 module may include a centralized data storage and system administration system. In various embodiments, subject medical data 571 module may include a secure subject data service 520 (not shown), such as, for example, a networked data provider for securely providing subject data such as, for example, subjects' medical and descriptive data accessed based on identifiable data of the subject, and other data such as, for example, locations of medical facilities, hospitals, bases, and any and all other pertinent geolocation values. In various embodiments, subject medical data 571 module may include one or more outside secure data providers, either in place of, or in addition to, a secure subject data service (not shown). In various embodiments, subject medical data 571 module may be a memory buffer of subject medical data that can be accessed via a secure subject data service including descriptive data, and medical data and via command center server 580 and user interface 575, 545. Command center server may include one or more servers 580 (e.g., Linux, windows, blade servers), a distributed working memory (e.g., software running on server), one or more network switches and/or encryption switches, a persistent storage unit (e.g., NoSQL, MySQL cluster, database). In various embodiments, command center server 580 may communicate with user interface module 575 via an object-oriented data interchange format such as, for example, JavaScript Object Notation (JSON) and provide, for example, NoSQL, or MySQL cluster, persistence. In various embodiments, command center server 580, subject medical data 571 module, and subject registration data 572 module, may include and provide suitable industry security and web services to facilitate data population and receipt. In various embodiments, subject medical data 571 module may include a transactional data warehouse, with analytical and operational data marts (now shown). In various embodiments, user interface 575 may provide a system administration portal for system administrative users and analyst users to perform maintenance and troubleshooting on the system. In various embodiments, command center server 580 provides a secure, high-speed connection between user interface 575, modules of mobile communication and display device 537 via communications interface B 547 module, subject medical data 571 module, and/or subject registration data 572 module.

In various embodiments, the prognosis engine 550 generates real-time prognosis scores for each of a plurality of subjects using generated machine readable values for each of a plurality of physiological, physical, and/or environmental parameters, and one or more prognosis weighting factors (from prognosis weighting modules 558). In various embodiments, the prognosis engine generates real-time respective severity scores for each of a plurality of physiological, physical, and/or environmental parameters, for each of a plurality of subjects using generated machine readable values for such parameters and a plurality of severity thresholds (from severity threshold module 559). In various embodiments, prognosis engine 550 interfaces with communications interface A module 546, prognosis weighting module 558, severity threshold module 559, subject monitoring core 540-N, subject medical data module 530, and/or user interface 545. In various embodiments, the triage prioritization engine 560-A selects a triage prioritization order of the subjects, including subjects in A monitoring groups, using the generated prognosis scores from prognosis engine 550. In various embodiments, the triage prioritization engine 560-A interfaces with prognosis engine 550, subject monitoring core 540-N, location data module 531, communications interface B module 547, and/or user interface 545.

Figure 7:
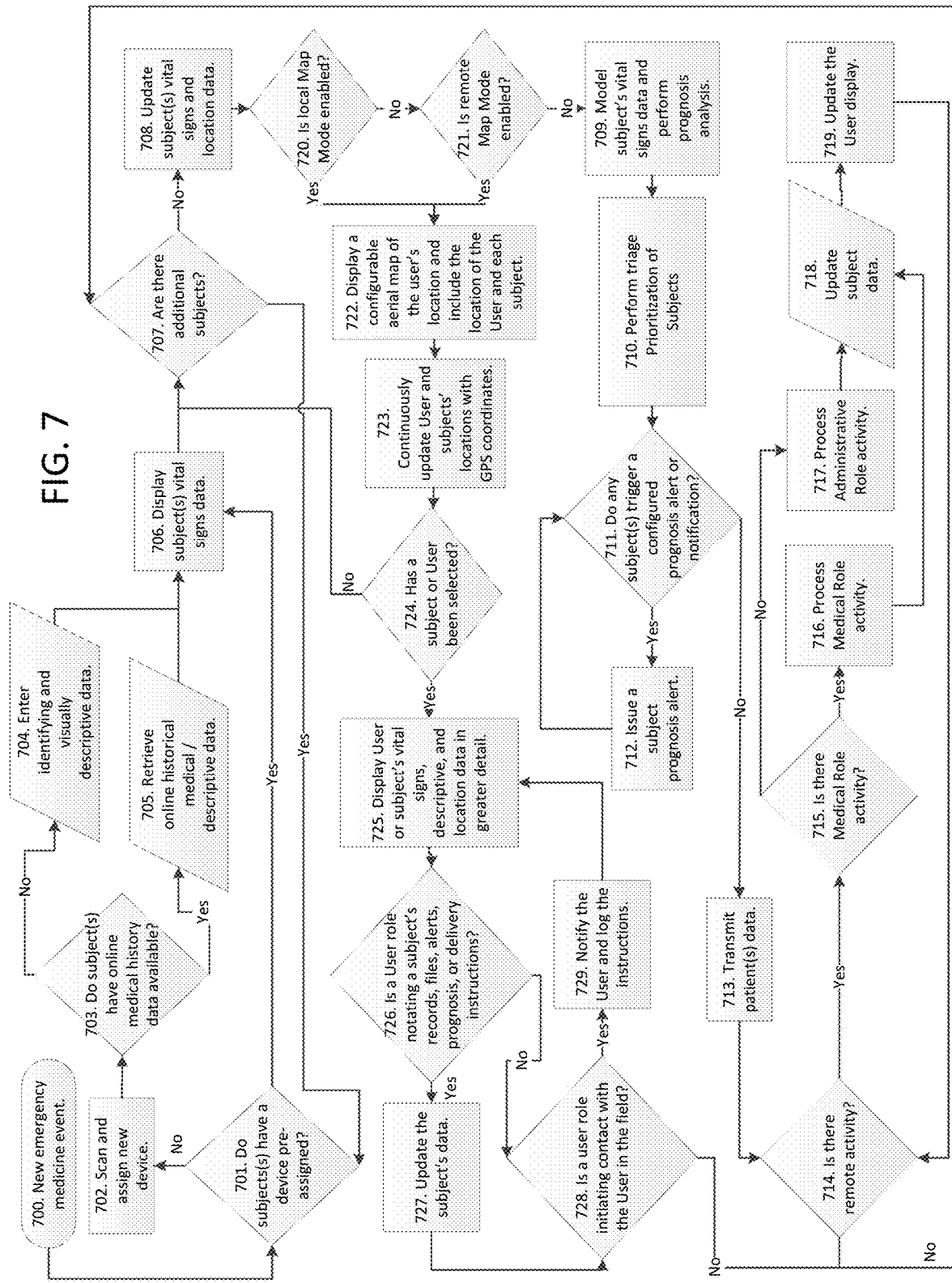
FIG. 7 is a flow chart illustrating a computer-implemented method of remote physiological monitoring of subjects, and of automated triage prioritization, according to some embodiments.

FIG. 7 is a flow chart illustrating a computer-implemented method of automated triage prioritization according to some embodiments. At block 700, an emergency medical event with casualties to a plurality of subjects occurs in accordance with some embodiments. At block 701, a first subject has an enhanced monitoring device (140) with each of its plurality of physiological sign portions applied to different, respective surfaces of his/her body, and a subject monitoring core (540) of a mobile communication display device (537) determines if the subject has been pre-assigned (e.g., pre-registered) to the applied enhanced monitoring device (140). In various embodiments, if the subject has not been pre-assigned the enhanced monitoring device (140), at block 702, a user (e.g., medic, first responder, EMT) may scan the enhanced monitoring device (140) on the mobile communication display device to read the enhanced monitoring device's (140) RFID (or barcode, or QR code) to obtain the enhanced monitoring device's unique identification string. In various embodiments, at block 702, an enhanced monitoring device may automatically transmit its respective RFID (or barcode, or QR code) to the mobile communication display device (e.g., 537) once the enhanced monitoring device has been removed from any packaging and/or activated by a user (e.g., 533). The subject monitoring core of the mobile communication display device then assigns (e.g., registers in in data repository 532) this enhanced monitoring device to this subject. At block 703, the subject monitoring core (e.g., 540) of the mobile communication display device (e.g., 537) queries online medical data repositories (e.g., subject medical data repository 571) via communications interface (e.g., 547) (e.g., over a wireless network, the Internet, a cloud computing network), and/or subject medical data repositories (e.g., 530) stored thereon, to determine if the subject's electronic medical record and/or fitness record is available to be retrieved by mobile communications and display device. If the subject's electronic medical record and/or electronic fitness record is not available to the mobile communications and display device, at block 704, the user (e.g., 533) may enter identifying and visually descriptive data to identify this subject which can be stored in memory of the mobile communication display device (e.g., 530, 532). If the subject's electronic medical record and/or electronic fitness record is available online (e.g., 571), or in a data repository (e.g., 530) of the mobile communication and display device (e.g., 537), at block 705, the subject monitoring core of the mobile communication display device retrieves this subject's electronic medical and descriptive data.

In various embodiments, once the physiological sign portions of an enhanced monitoring device are deployed on respective, different surfaces of a subject (e.g., on a surface of an ear opposite a concha of a subject, a surface over a mastoid region of the neck of the subject, a surface over another region of the neck of the subject, and/or a skull, nose, or face surface of the subject 100 opposite a portion of an eyeglasses physiological sign monitoring portion), a transmitter of the enhanced monitoring device transmits electronic signals including the subject's physiological data, environmental data, and/or location, orientation, motion, etc. data, to a receiver of the mobile communications and display device (e.g., 537). At block 704, 705, or if the subject had a pre-assigned enhanced monitoring device (e.g., 140) at block 701, the human readable values indicative of the registered subjects' physiological signs data are displayed, at block 706, on a display of the mobile communication display device via user interface 545. At block 707, the subject monitoring core of the mobile communication display device validates the existence of additional subjects to be registered to enhanced monitoring devices (e.g., 140). If there are additional subjects to register, the method returns to block 701. If there are no additional subjects to register, at block 708, prognosis engine 550, triage prioritizing engine 560-A, and/or subject monitoring core 540-N, updates the registered subjects' physiological signs data from respective electronic signals received via wireless communications of the corresponding enhanced monitoring devices (e.g., 140). At block 720, program code executable by a processor of the mobile communication display device, and encoded on a non-transient machine readable storage medium of the mobile communication display device, determines if the user (e.g., 533) local to the mobile communication display device (e.g., 537) has enabled a Map Mode on the mobile communication display device (e.g., 537) which is configured to display, for example, a configurable aerial map of the user and subjects' monitoring devices reporting their locations on a display of the mobile communication display device (e.g., 537). At block 721, program code executable by a processor of the command center server and/or by a processor of a remote computer, and encoded on a non-transient machine readable storage medium of the command center server or remote computer, determines if a remote administrative user or medical user (e.g., 573) has enabled a Map Mode on a display of a remote computer (e.g., 573, 574) which is configured to display, for example, a configurable aerial map of the user and subjects' monitoring devices reporting their locations on a display of the remote computer (e.g., 573, 574). At block 722, the mobile communication display device (e.g., 537), and/or remote computer (e.g., 573, 574), displays the Map Mode for the current user (e.g., 533, 573).

At block 723, subject monitoring core (e.g., 540-N) of the mobile communication display device (e.g., 537) updates the user's location data based on the location information (e.g., GPS coordinates) provided by the mobile communication display device and the subjects' location data based on the location information (e.g., GPS coordinates) provided by their enhanced monitoring devices (e.g., 140) from respective electronic signals received via network communications (e.g., Bluetooth network) of the corresponding enhanced monitoring devices (e.g., 140). At block 724, program code executable by a processor of the mobile communication display device (e.g., 537), and/or program code executable by a processor of command center server (e.g., 580) or a remote computer (e.g., 574), determines if a user or subject has been selected on the user interface 545 of the mobile communication display device, and/or a user interface 575 of a remote computer (e.g., 573, 574), in the Map Mode. If not, the method returns to block 722 and updates the user and the subjects' locations on the map. If a user or subject has been selected on the user interface 545 of the mobile communication display device, and/or a user interface 575 of a remote computer (e.g., 573, 574), in Map Mode, at block 725, a display of the mobile communication display device, and/or a display of a remote computer (e.g., 573, 574), displays, for example, additional physiological signs, medical records, fitness records, descriptive, administrative, alerts, notifications, instructions, location details, and other available and suitable data for the clicked selected user and/or subject. Users local to the mobile communication display device (e.g., 537), and/or remote administrative users or medical users (e.g., 573, 574), may then choose to add notes on the user or subject's medical records and/or fitness records, add files, communicate with the user, or other users, modify a prognosis for the subject, modify delivery instructions, add alerts, log what happened to a subject from the point of injury, enter and update interventions (e.g., CPR, medical administration, intubation, tourniquet applied, airway access, etc.) for logging in subject's medical records, or perform other suitable actions, at block 726. At block 727, program code executable by a processor of the mobile communication display device, and/or program code executable by a processor of a remote computer, performs the actions selected by the user. If such users do not perform one or more functions at block 726, such user may give instructions or orders with alerts at block 728. If such users choose to give instructions or orders with alerts at block 728, program code executable by a processor of the mobile communication display device, and/or program code executable by a processor of a remote computer, gives instructions or orders with alerts selected by the user at block 729. The method then returns to block 722 to update the user and subjects' locations on the map displayed on a display of the mobile communication display device, and/or displayed on a display of a remote computer.

At block 709, each subject's physiological signs data, environmental parameters data, location, orientation, motion, etc. data, and/or other suitable subject data, communicated to the mobile communication display device via communications interface A (e.g., 546), is data modeled, statistically analyzed, and/or predictively modeled, to generate prognosis scores by prognosis engine 550 of the mobile communication display device. At block 710, triage prioritizing engine 560-A generates a triage prioritization order of the subjects based on prognosis scores generated by prognosis engine 550 of the mobile communication display device at block 709. If block 709 or block 710 results in an alert condition, at block 711, program code executable by a processor of the mobile communication display device generates a suitable alert, and, at block 712, program code executable by a processor of the mobile communication display device displays, and/or communicates, the generated alert to the user via user interface 545, or an appropriate user (e.g., administrative role, or medical role) via user interface 575, depending on the conditions of the generated alert. If there are additional alerts to be handled by the mobile communication display device, block 711 repeats. If there are no additional alerts to be handled by the mobile communication display device, each subject's physiological signs data, environmental parameters data, location, orientation, motion, etc. data, and/or other suitable subject data received by the mobile communication display device, is stored in a data repository of the mobile communication display device, and/or transmitted to a centralized data repository (e.g., 571) at block 713. At block 714, program code executable by a processor of a command center server (e.g., 580), and/or by a processor of a remote computer/computing device (e.g., 573, 574) validates if remote activity is being performed by one or more users (e.g., 573, 574). If command center server (e.g., 580), and/or remote computer (e.g., 573, 574), validates remote activity, at block 715, program code executable by a processor of the command center server, and/or by a processor of remote computer (e.g., 573, 574), validates if the remote activity is from a medical or administrative role. If command center server (e.g., 580), and/or remote computer (e.g., 573, 574), validates the remote activity is from a medical role, at block 716, program code executable by a processor of the command center server, and/or by a processor of a remote computer (e.g., 573, 574), processes this activity. If command center server (e.g., 580), and/or remote computer (e.g., 573, 574), validates the remote activity is from an administrative role, at block 717, program code executable by a processor of the command center server, and/or by a processor of a remote computer, processes this activity. At blocks 716 and 717, program code executable by a processor of the command center server, and/or by a processor of a remote computer, updates respective subject data at block 718. At block 719, program code executable by a processor of the command center server, and/or by a processor of a remote computer, updates the subjects' data with the most up-to-date data, and a display of a remote computing device (e.g., 573, 574) displays the data to the user. The method returns to block 714 where program code executable by a processor of the command center server, and/or by a processor of a remote computer, validates additional remote activity. If the program code executable by a processor of the command center server, and/or by a processor of a remote computer, determined there is no remote activity at block 714, then the method returns to block 707 to determine if there are additional subjects to be registered with corresponding enhanced monitoring devices 140.

Figure 8A:
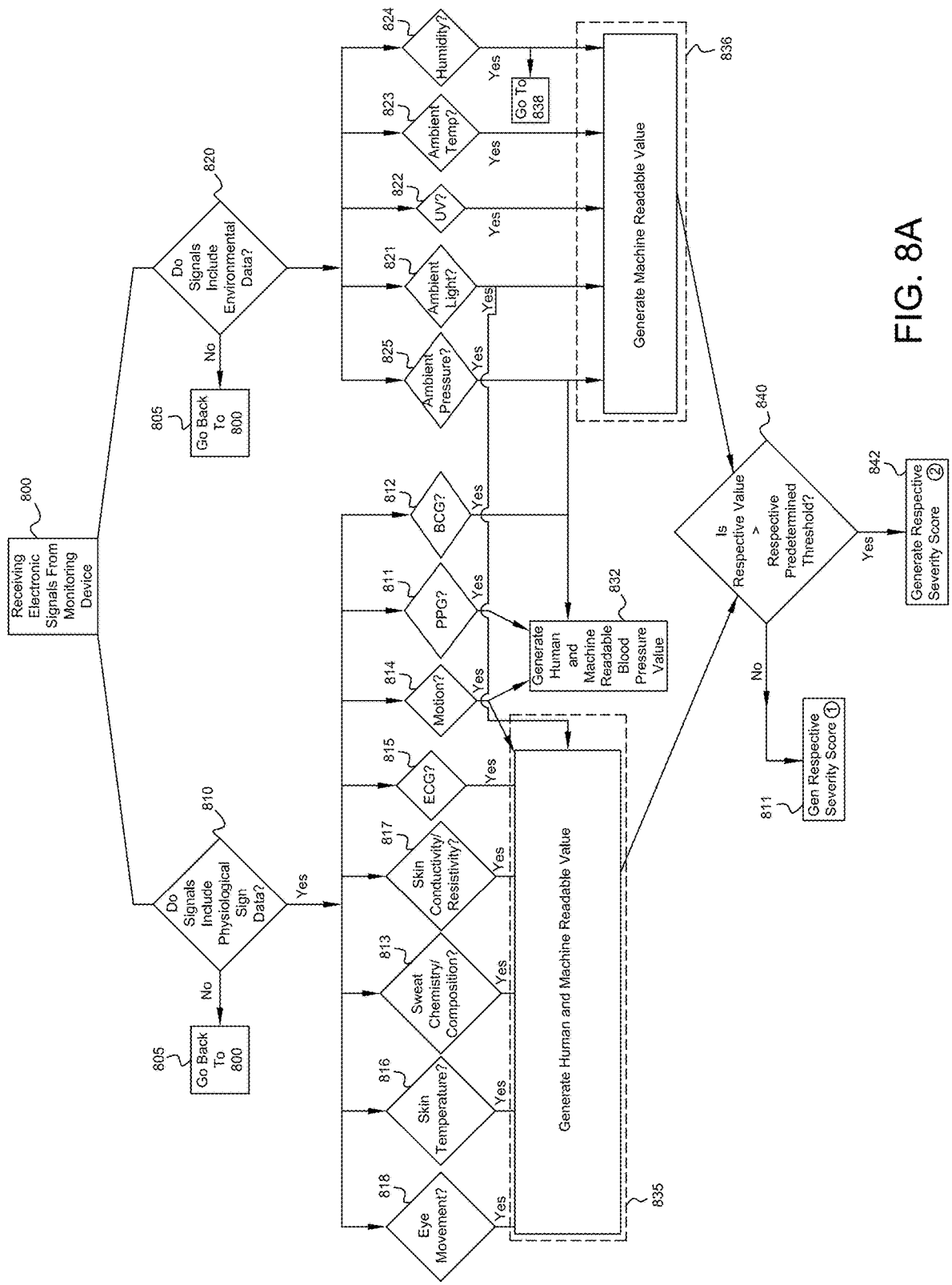
FIGS. 8A-8C are flow charts illustrating examples of a computer-implemented method of remote physiological monitoring of subjects, and of automated triage prioritization, according to some embodiments of the present disclosure.
Figure 8B:
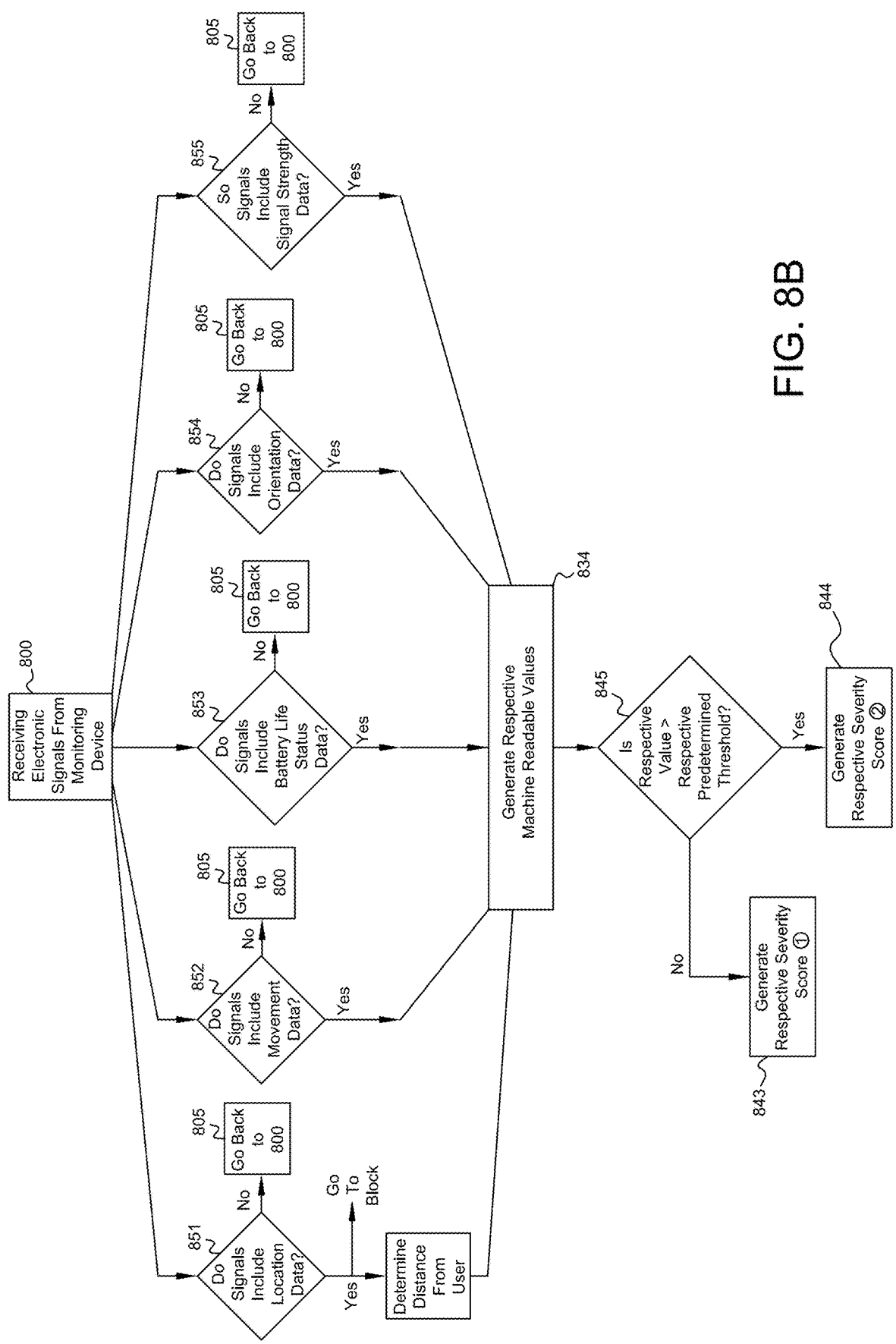
Figure 8C:
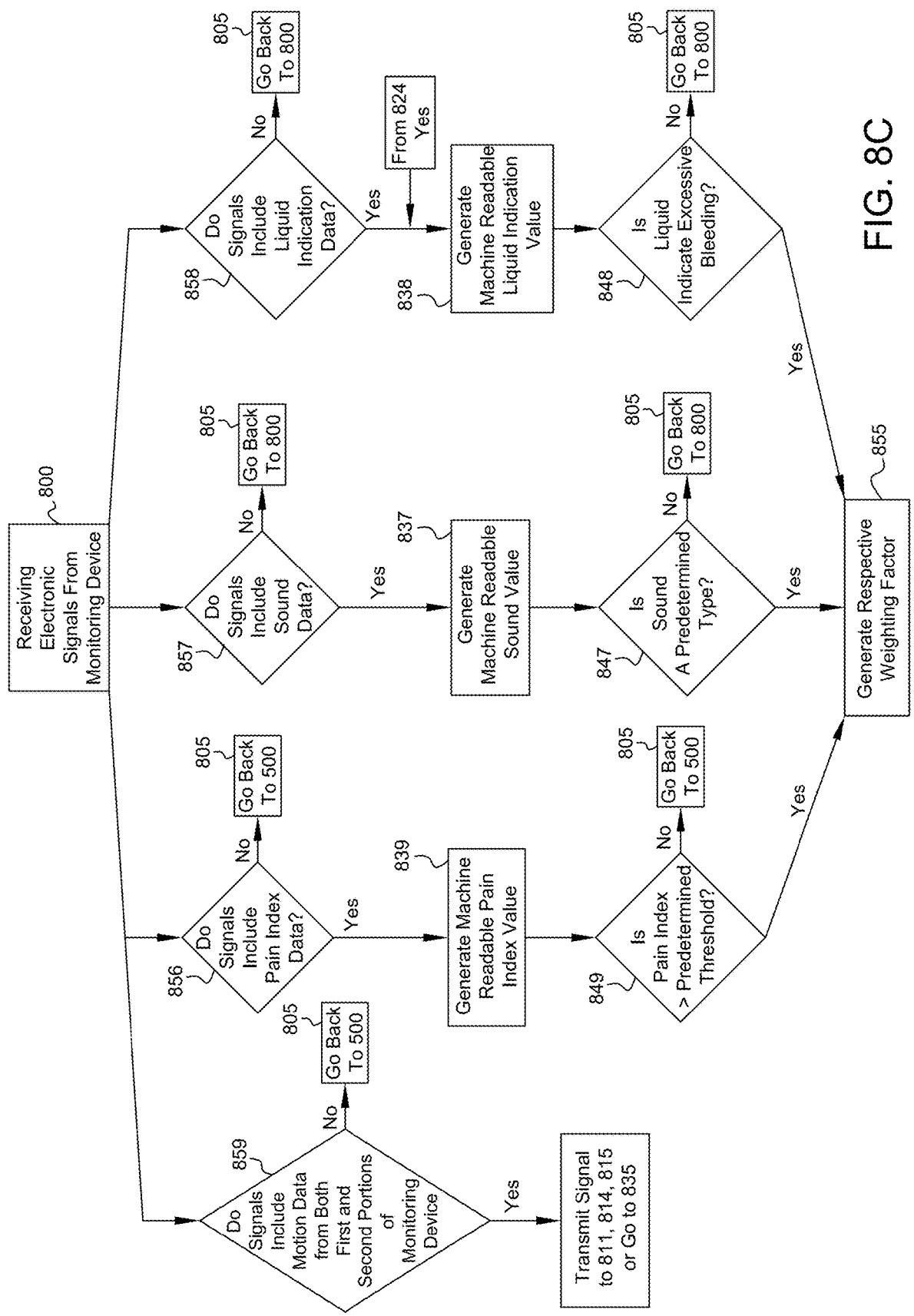

Referring now to FIGS. 8A-8C, computer-implemented methods of remote physiological monitoring of subjects, and of automated triage prioritization, are provided. In some embodiments, a plurality of enhanced monitoring devices are provided where each enhanced monitoring device includes a first physiological sign portion and a second physiological sign portion. In some embodiments, each first physiological sign portion of each enhanced monitoring device is configured for deployment on a surface of the back of a respective ear (e.g., opposite a concha) of a respective subject, and each second physiological sign portion is configured for deployment on a surface over a region of the neck of the subject (e.g., mastoid region, USP, LSP1, LSP2), or on a skull, nose, or face surface of the subject 100 opposite a respective portion of each eyeglasses second physiological sign monitoring portion. In some embodiments, each first physiological sign portion of each enhanced monitoring device is configured for deployment on a surface over a mastoid region of the neck of a subject, and each second physiological sign portion is configured for deployment on a surface over another region of the neck of the subject (e.g., USP, LSP1, LSP2), or on a skull, nose, or face surface of the subject 100 opposite a respective portion of each eyeglasses second physiological sign monitoring portion. In some embodiments, each physiological sign portion of each enhanced monitoring device includes a respective plurality of physiological sensors. For example, the plurality of physiological sensors in the first physiological sign portion may include a PPG sensor including an emitter configured to emit light in a direction toward the ear cavity (e.g., toward a concha such as the cavum concha) and a receptor configured to receive light reflected from one or more sources in the direction where the PPG sensor is configured to generate an electronic photoplethysmogram signal based on the received, reflected light. The plurality of physiological sensors in the first physiological sign portion (and/or in the second physiological sign portion) may also include an electrocardiogram sensor configured to monitor an electrical potential at the monitored surface (e.g., back of an ear, skin over a mastoid region of neck, skull, nose, or face surface opposite a portion of an eyeglasses second physiological sign monitoring portion), a BCG sensor, and a motion sensor configured to monitor motion (e.g., neck motion, head motion, general motion) at the respective monitored surface (e.g., back of an ear, skin over a mastoid region of neck, USP, LSP1, LSP2, skull, nose, or face surface opposite a portion of an eyeglasses second physiological sign monitoring portion) relevant to a motion axis. In some embodiments, the PPG sensor and one or more motion sensors are configured to generate respective signals usable to generate values indicative of blood pressure. The plurality of physiological sensors may also include, for example, a combination of an electrocardiogram sensor, a motion sensor, and a PPG sensor. The plurality of physiological sensors may also include a combination of a PPG sensor and a skin temperature sensor. The plurality of physiological sensors may also include a skin conductance sensor or a skin resistance sensor or combinations thereof. The plurality of physiological sensors may also include a sweat chemistry or sweat composition sensor or combinations thereof. Other suitable physiological sensors may be included in any of the physiological sign portions (e.g., 110, 120) of an enhanced monitoring device 140.

In some embodiments, one or more physiological sign portions of each enhanced monitoring device also includes an orientation sensor configured to monitor an orientation of the respective subject relative to an orientation axis and to generate an electronic orientation signal based on the monitored orientation. In various embodiments, one or more physiological sign portions of each enhanced monitoring device includes one or more environmental sensors including a pressure sensor configured to monitor ambient pressure around a surface of the respective subject and to generate an electronic ambient pressure signal based on the monitored pressure. In some embodiments, the one or more environmental sensors includes at least one of an ambient temperature sensor, a humidity sensor, a UV index sensor, an altitude sensor, and an ambient light sensor, such that each of the one or more environmental sensors is configured to monitor a corresponding environmental parameter around the surface of the respective subject and to generate a corresponding electronic signal based on the monitored environmental parameter.

In various embodiments, each enhanced monitoring device 140 also includes a transmitter configured to transmit the generated electronic signals over a first network such as, for example, a Bluetooth network (e.g., a Bluetooth Low Energy (LE) smart network). In some embodiments, the first physiological sign portion of the enhanced monitoring device is configured to transmit the first physiological sign portion generated electronic signals to the second physiological sign portion over a wired connection. At block 800, electronic signals from one or more of the plurality of enhanced monitoring devices 140 are received by a mobile communication and display device 537 (e.g., from each physiological sign monitoring device 140, from a monitoring device hub 502, from a relay network device 505). In various embodiments, the mobile communication and display device 537 includes a communications interface A module 546 configured to be coupled to the first network and to receive the transmitted electronic signals over the first network from each of the transmitters of each of the plurality of enhanced monitoring devices, a user interface 546, a processor coupled to the communications interface, and a non-transient machine-readable storage medium encoded with program code executable by the processor. At block 810, a determination is made as to whether the signals include physiological data (e.g., from a respective one or more of the respective plurality of physiological sign portions of an enhanced monitoring device). If the received electronic signals do not include physiological data, at block 805, the method returns to block 800. If the received electronic signals include physiological data, at block 812-817, a determination is made as to the type of physiological data in the received electronic signals.

At block 816, if the received electronic signals for a respective subject include skin temperature data for the subject, program code executable by the processor will generate respective human and machine readable values indicative of skin temperature, core body temperature, and/ or cranial temperature for the respective subject using the received electronic signals at block 835. At block 818, if the received electronic signals for a respective subject include eye movement for the subject (e.g., EOG data), program code executable by the processor will generate respective human and machine readable values indicative of eye movement, eye muscle movement/potential, gaze, pupil dilation, blinking, lighting conditions, and/or other eye features for the respective subject using the received electronic signals at block 835. At block 813, if the received electronic signals for a respective subject include sweat chemistry/composition data for the subject, program code executable by the processor will generate respective human and machine readable values indicative of hydration level, stress level, and/or glucose level for the respective subjects using the received electronic signals at block 835.

At block 817, if the received electronic signals for a respective subject include skin resistivity/conductivity data for the subject, program code executable by the processor will generate respective human and machine readable values indicative of galvanic skin response, hydration level, stress level, and/or bioimpedance for the subject using the received electronic signals at block 835. At block 815, if the received electronic signals for a subject include ECG data for the subject, program code executable by the processor will generate respective human and machine readable values indicative of at least one of respiratory rate, heart rate variability, pulse transit time, pulse wave velocity, ECG pulse rate, pulse deficit, premature ventricular complexes, R-R interval, maximal oxygen uptake, stress level, subject activity level, and/or arterial characteristics, for the respective subjects using the received electronic signals at block 835.

The inventor has determined that the enhanced monitoring devices, systems, and methods described herein provide a novel way to non-invasively and unobtrusively (e.g., without any tubing or devices near the nose or mouth) calculate a subject's respiratory rate, even while they perform physical activities. In various embodiments, a subject's respiratory rate may be calculated via different facets of human physiology, and by performing a weighted averaging of the techniques based on the subject's current motions and a determination of which waveform signals were best acquired during the previous time period and then prioritizing optimal waveform signals, and then by applying the subject's physical characteristics, parameters, and biometrics. In various embodiments, the respiratory rate results determined using each technique, along with previous input data and population correlation data, are then fed into a machine learning algorithm.

The inventor has determined that non-invasive, calculable methods of acquiring respiratory rate fall into these data and technique categories: PPG waveforms, ECG waveforms, hybrid solutions utilizing PPG waveforms and ECG waveforms, and physical breath motions. The inventor has observed that PPG and ECG waveforms both exhibit three respiratory modulations: baseline wander (BW), amplitude modulation (AM), and frequency modulation (FM), and the inventor's determined respiratory rate algorithms that utilize PPG or ECG waveforms estimate respiratory rate by analyzing one or more of these modulations. The inventor has observed that the physiological mechanisms that cause respiratory modulations can be summarized as: BW of the PPG is due to changes in tissue blood volume caused by changes in intrathoracic pressure transmitted through the arterial tree and vasoconstriction of arteries during the process of inhalation transferring blood to the veins; AM of the PPG is caused by reduced stroke volume during inhalation due to changes in intrathoracic pressure, reducing pulse amplitude; BW and AM of the ECG are caused by changes in the orientation of the heart's electrical axis relative to the electrodes and changes in thoracic impedance; and FM is the manifestation of the spontaneous increase in heart rate during inspiration, and decreases during exhalation, known as respiratory sinus arrhythmia (RSA). The inventor has observed that RSA is caused by three mechanisms: changes in intrathoracic pressure during inhalation stretch the sinoatrial node, increasing heart rate; increased vagal outflow during exhalation reduces heart rate; and reduced intrathoracic pressure during inhalation decreases left ventricular stroke volume, causing a baroreflex-mediated increase in heart rate.

The inventor has further observed that the PPG waveforms show the local changes of blood volume in tissues, that respiration induces variation in the PPG baseline due to the variation in venous blood return during each breathing cycle, and that cardiovascular, respiratory, and neural fluctuations in the PPG signal are of different frequencies and can all be characterized according to their sinusoidal components. As is known in the art, many existing methodologies are designed to ascertain respiratory rate from PPG waveforms, and many existing methodologies are designed to ascertain respiratory rate from ECG waveforms (e.g., R-wave amplitude method, R-to-S-wave method, principal component analysis method, kernel principal component analysis method, Q-R slope method, R-S slope method, R-wave angle method, QRS slope range method, central moment method, QRS area method, etc.). ECG methods are experimentally considered higher-quality and have a higher efficacy. In various embodiments, hybrid methods of ascertaining respiratory rate include features of both the PPG and ECG waveforms, and selectively picking the optimal features of each waveform. The inventor has observed that the physical act of breathing causes specific motions to the side of the neck. The inventor has determined that these specific motions may be detected by measuring accelerometer motion patterns (e.g., in all 3 axes) at, for example, a "Sempulse Point" (USP, LSP1, LSP2). In various embodiments, these specific neck motions may be compiled as a respiratory waveform and directly correlate to each breath the subject took.

In various embodiments, due to the fact that the physical monitoring of the respiratory waveform, and those methods that utilize ECG waveform data, are of higher quality (as observed by the inventor), these methods are weighted higher. However, the inventor also observed that physical respiratory waveform and ECG waveform data may become noisy during periods of high motion or physical activity. In various embodiments involving these high motion or physical activity cases, the hybrid methods that utilize the most noise-resistant features of the ECG waveform (i.e., R-peaks) are weighted the highest. In various embodiments, and especially in cases where no physical respiratory waveform or ECG waveform data are available, the PPG methods are weighted the highest. In various embodiments, any unavailable methods are weighted zero. In various embodiments, a subject's respiratory rate may be calculated using at least 3 methods from each weighted section, along with the single physical respiratory waveform, heart rate, pulse oximetry ($SpO_2$), accelerometer data, the subject's physical activity metrics, motion data, population correlation data, and the subject's physical characteristics, parameters, and biometrics are also input. In various embodiments, machine learning is then be performed on the weighted, final values.

At block 811, if the received electronic signals for a respective subject include PPG data for the subject, program code executable by the processor will generate respective human and machine readable values indicative of pulse oximetry, blood pressure, heart rate, respiratory rate (as described above), end tidal $CO_2$, pulse transit time, pulse wave velocity, maximal oxygen uptake, stress level, subject activity level, coughing, sneezing, and/or arterial characteristics. For example, the inventor has determined a technique for obtaining an End-Tidal Capnography $CO_2$ ($EtCO_2$) equivalent waveform and accompanying metrics that specify the amount of carbon dioxide in the blood from a PPG waveform. As is known in the art, carbon dioxide ($CO_2$) is a product of metabolism transported via perfusion and expelled through ventilation. The inventor has observed that $EtCO_2$ may also confirm airway device placement and monitor ventilation, and, the inventor has determined that end-tidal carbon dioxide waveform monitoring permits a user to measure the metabolism, ventilation, and perfusion of a patient simultaneously. Prior capnography techniques required a subject to be fully enclosed or to monitor a subject's breathing at either the nose, mouth, or both so that all breath activity can be monitored and analyzed. In various embodiments, correlation data between PPG waveform data, pulse oximetry ($SpO_2$), respiratory rates, subject parameters, and direct-measure $EtCO_2$ and population correlation data from a plurality (e.g., thousands) of samples are used to perform a correlation analysis and ascertain the carbon dioxide capnography waveform. The inventor has determined that this technique allows for a non-invasive measure of $CO_2$ in the blood based on the strong correlations that the inventor has determined between $O_2$ and $CO_2$ in the bloodstream.

At block 812, if the received electronic signals for a respective subject include BCG data for the subject, program code executable by the processor will generate respective human and machine readable values indicative of blood pressure for the subject using the received electronic signals at block 835. At blocks 814 and 811, if the received electronic signals for a respective subject include motion data and PPG data for the subject, program code executable by the processor will generate respective human and machine readable values indicative of blood pressure for the subject using the received electronic signals at block 832. At block 815, if the received electronic signals for a subject include ECG data, program code executable by the processor may generate respective human and machine readable values indicative of at least one of heart rate, pacemaker edge detection (e.g., with three chamber pacing with data logging and ECG tagging for three rising and falling edges), or R-R interval (e.g., using an adaptation of the Pan-Tompkins QRS detection algorithm described below). At block 815, if the received electronic signals for a subject include ECG data and electrical potential data from another electrical potential sensor (e.g., another ECG sensor in another physiological sign portion of enhanced monitoring device 140), program code executable by the processor may generate respective human and machine readable values indicative of at least one of stroke volume, heart rate, cardiac output, ventricular ejection time, or pre-ejection period. At blocks 815, 814, and 811, if the received electronic signals for a subject include ECG data, motion data, and PPG data, program code executable by the processor may generate respective human and machine readable values indicative of at least one of mean arterial blood pressure, systolic blood pressure, diastolic blood pressure, pulse transit time, pulse wave velocity, or R-J interval.

The inventor has determined a technique to calculate mean arterial blood pressure from electrocardiogram (ECG) signal data (ECG sensor), photoplethysmogram (PPG) signal data (PPG sensor), and ballistocardiogram (BCG) data (BCG sensor and/or motion sensor) signal data to extract mean blood pressure up the carotid artery. The inventor has also determined a technique to then calculate pulse wave velocity, pulse transit time, systolic blood pressure, and diastolic blood pressure from the mean arterial blood pressure. For example, to calculate pulse wave velocity, the inventor has determined a technique using electrocardiogram (ECG) signal data, ballistocardiogram (BCG) signal data, and pulse wave transit time (as pulse wave transit time (TPTT) and blood pressure are oppositely correlated). The inventor has derived an equation to calculate systolic blood pressure (PS) from TPTT by combining a formula concerning blood vessels' elasticity and Moens-Korteweg's equation: $P_S = 1/\alpha \times \ln(2\rho r \Delta x^2/(E_0 h T_{PTT}^2))$. In this equation $\alpha$ is a constant issued from blood vessels' characteristics, $E_0$ is blood vessels' modulus of longitudinal elasticity when Ps is 0 mmHg, h is the vascular wall's thickness, $\rho$ is blood density, r the intravascular diameter, and $\Delta x$ the distance between the heart and pulse wave measure point (back of the cavum concha). The inventor considered that, to measure blood pressure in daily activities, covering a wide range of physiological status from rest to exercise is required. Thus, the inventor considered changes in blood vessels' inner diameter since he expected the elasticity of the vessels to change the blood vessels' inner diameter when blood pressure increases due to exercise or stress. Thus, the inventor took these considerations into account in the equation: $\Delta Pr \Delta\theta = 2E\Delta r/r \times h \sin(\Delta\theta/2)$. The inventor also identified that a BCG signal can be noisy during motion, and thus looked to replace $T_{PTT}$ in the equation. The inventor identified that, generally, variations of the time of pre-ejection period, $T_{PEP}$, are minimal, and thus replaced $T_{PTT}$ by $T_{PAT}$, pulse arrival time to achieve the equation: $P_S = 1/\alpha \times \ln(2\rho\Delta x^2/c_0 T_{PAT}^2) - 1/\alpha c_0$. In this equation, $\Delta P$ is the variation of intravascular pressure, $\Delta\theta$ is the central angle of blood vessel, E is the blood vessels' Young modulus of longitudinal elasticity, $\Delta r$ is the variation in blood vessels' diameter, and $c_0$ is integration constant. The inventor also determined calculating R-J interval by ascertaining the difference in time between the body telling the heart to beat (via ECG signal) and the appearance of the blood in the head (BCG signal).

As discussed above, the inventor has determined a pulse wave technique to calculate non-invasive, unobtrusive, cuffless blood pressure of a subject. The inventor has observed that the forces exerted by the underlying arterial pressure (pulse) wave create arterial and venous elasticity waves and skin surface motions. In various embodiments, the enhanced monitoring devices, systems, and methods described herein may measure these elasticity waves and skin motions spatiotemporally and in three dimensions through the use of one or more of optical sensors that direct and receive light waves reflected off of the arterial and venous walls, sensitive accelerometers that can directly sense the pulse wave through its transferred force to the skin's surface, cameras that can detect the pulse wave through its transferred force to the skin's surface, and/or distance-sensing techniques (e.g., SONAR, LIDAR, etc.) that can detect pulse wave through its transferred force to the skin's surface. In various embodiments, enhanced monitoring device 140 includes a PPG sensor 115, including an optical sensor with infrared, red, and green LEDs and a photodetector, and a motion sensor (112, 122) including a 3-axis accelerometer (e.g., configured to be deployed at a respective point of at least one physiological sign portion (e.g., 110)). In various embodiments, a physiological sign portion (110, 120) of enhanced monitoring device 140 may include a camera (not shown) and/or distance-sensing technique system (not shown). As described herein, the respective sensing points (e.g., on the back of an ear, over a mastoid region, USP, LSP1, LSP2, skull, nose, or face surface opposite a portion of an eyeglasses physiological sign monitoring portion) are over the superficial arteries of subject 100, corresponding sensors in one or more physiological sign portions (110, 120) of enhanced monitoring device 140 may continuously detect blood pressure waveforms and other physiological parameters such as heart rhythm, respiratory rhythm, and pulse rate directly from the vascular system. In various embodiments, PPG signals (block 811), and motion signals (block 814) and/or BCG signals (block 812), may provide, in combination, respective inputs to a pulse wave methodology technique configured to use the force waves detected in both methods to provide a single, clean blood pressure force waveform. In various embodiments, in the case of high general motion of the subject 100, such as in running, weighting factors may be used in the motion-based techniques so more of an emphasis is placed on the arterial wall methodologies. In various embodiments, as an added layer of measurement, the known distance between the physiological sign measurement points of subject 100 (e.g., distance between the first physiological sign monitoring portion 110 and second physiological sign monitoring portion 120) may be used to further refine and clarify the force waveforms by way of creating a composite waveform over the multiple measurements that provides more accurate pattern and pulse wave data. The inventor has determined, through test subject data, that the enhanced monitoring devices, systems, and methods described herein provide clear pulse waveforms with distinct peaks and shapes that were characteristic of arterial pulses taken with more-invasive techniques. The inventor has also catalogued specific optical signatures, motion patterns, and force waveform patterns that have been shown to directly correlate to systolic and diastolic blood pressure and, as the force vectors are represented as spatiotemporal information, the inventor has performed this measurement continuously at low power.

Figure 3:
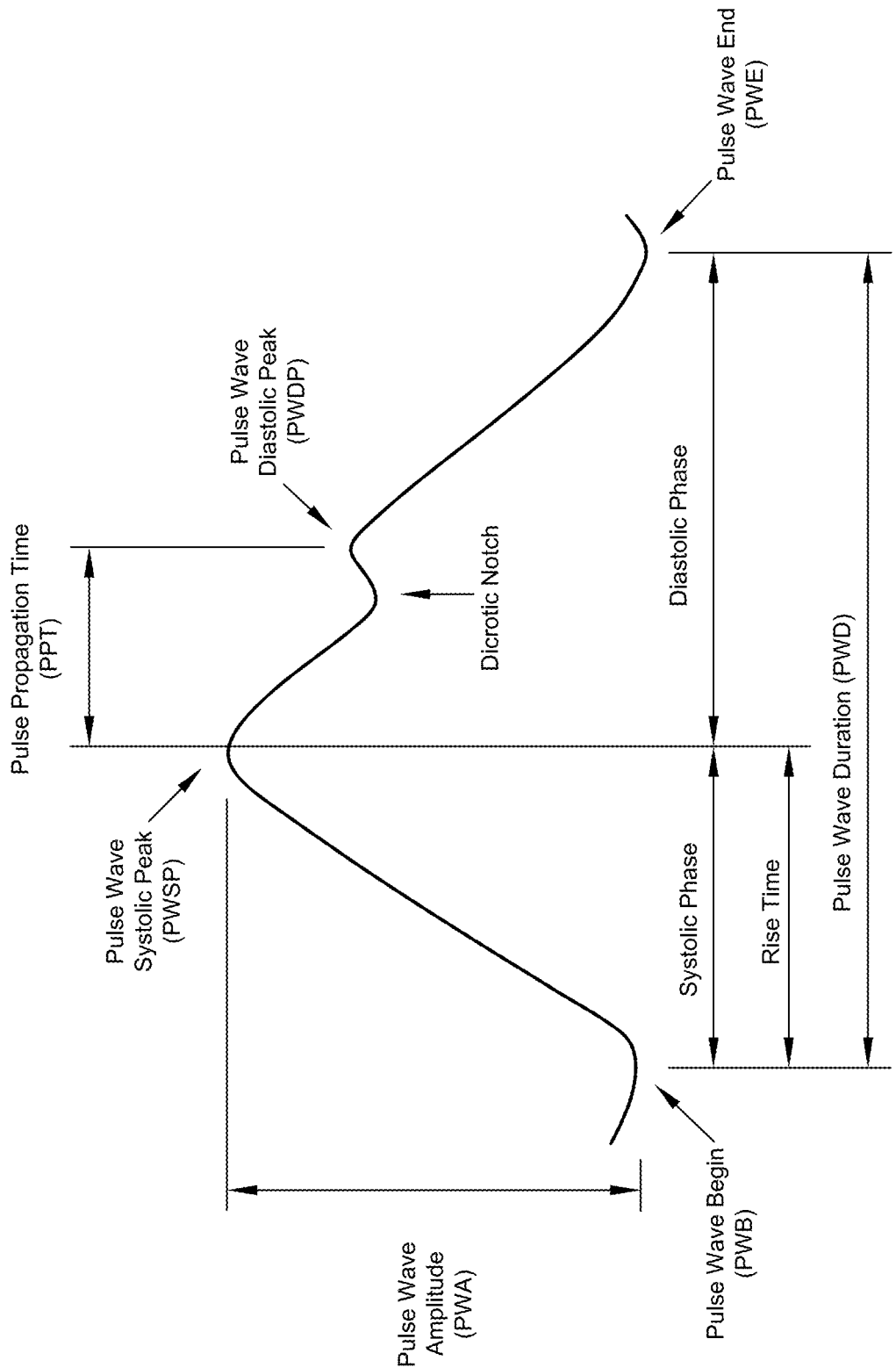
FIG. 3 is a diagram showing features of a photoplethysmogram (PPG) waveform in accordance with some embodiments of the present subject matter.

The inventor has also determined a technique to calculate non-invasive, unobtrusive, cuffless blood pressure of a subject, even while they perform physical activities. For example, the inventor has determined a technique to calculate blood pressure using the pulse wave methodology described immediately above and five (5) versions of the pulse transit time (PTT) methodology via five (5) facets of human physiology and then performing a weighted averaging of the six (6) methods (i.e., pulse wave methodology (described above) and five pulse transit time (PTT) methodologies (described below)) based on the subject's current physical activity motions. Then, in various embodiments, a factoring of arterial diameter and elasticity is applied to each. Then, in various embodiments, the subject's physical characteristics, parameters, and biometrics are applied to each. The inventor has determined that this technique, and, in various embodiments, a final analysis of the PPG waveform (e.g., block 811, FIG. 8; FIG. 3) results in mean arterial pressure (MAP), systolic pressure, and diastolic pressure values for each of the six (6) methods, which along with previous input data and population correlation data may be fed into a machine learning algorithm.

The Pulse Wave methodology according to various embodiments is described above. The Pulse Transit Time methodology according to various embodiments is based on the principle of pulse wave velocity (PWV) through the Moens-Korteweg (M-K) equation, which, as is known in the art, models the relationship between PWV and the elastic modulus of the arterial wall given a constant ratio of wall thickness to arterial diameter. However, the inventor observed that the variation of the arterial diameter is ignored in the M-K equation despite, as also observed by the inventor, arterial diameter affecting the flow and distribution of blood thereby regulating blood pressure. As observed by the inventor, the arterial diameter increases from its minimum during diastole to its maximum during systole over one cardiac cycle. In various embodiments, pulse transit time methodologies use a measure to model the arterial diameter. The inventor observed that during diastole, the arterial diameter is at its minimum and the transmitted light intensity will be at its maximum and that, during systole, the opposite is true; the arterial diameter is at its maximum and the transmitted light intensity will decrease to its minimum level. The inventor also observed that, during one cardiac cycle, the change of the optical path corresponds to the arterial diameter change and determined, therefore, the arterial diameter change may be derived from the peak and valley intensities of the PPG signal. The inventor further observed that, according to the modified Beer-Lambert law, photoplethysmogram intensity ratio (PIR) (i.e., the ratio of PPG peak intensity to valley intensity) may be derived in terms of the arterial diameter change under the assumption that the characteristic parameter remains constant and there is no change of the baseline arterial diameter. In various embodiments, PIR is used to augment the Pulse Wave Velocity calculations described above and to calculate blood pressure for a subject in motion. In various embodiments, the subject's physical parameters and biometrics (e.g., height, weight, body mass index (BMI), age, health, etc.) are also utilized in calculating blood pressure for a subject in motion. The inventor determined that biometric information increases the efficacy of PPG-based blood pressure calculations due to a refinement in the distance of arteries for the subject, and that body mass index (BMI), height, and age, may be used to estimate blood flow velocity, blood vessel stiffness, and pulse pressure (PP) range.

Referring now to FIG. 3, a diagram showing features of a photoplethysmogram (PPG) waveform in accordance with some embodiments of the present subject matter is provided. The inventor determined that various, minute features are available within the PPG waveform that correlate to blood pressure facets. As used in various embodiments, the five (5) Pulse Transit Time methods are: (1) calculate PTT as the time difference between the R-wave peak of the ECG signal and the peak of the PPG signal; (2) calculate PTT as the time difference between the R-wave peak of the ECG signal and the peak of the BCG signal; (3) calculate PTT as the time difference between the R-wave peak of the ECG signal and the physical arrival time of the pulse wave at one or more of the respective, deployed surfaces of the physiological sign portions (e.g., 110, 120) of the enhanced monitoring device (e.g., surface opposite a concha, surface over a mastoid region, USP, LSP1, LSP2) as measured by accelerometer motion in the direction away from the skin due to arterial enlargement during the pulse wave; (4) calculate PTT as the time difference between the physical arrival time of the pulse wave at one or more of the respective, deployed surfaces of the physiological sign portions (e.g., 110, 120) of the enhanced monitoring device as measured by accelerometer motion in the direction away from the skin due to arterial enlargement during the pulse wave and the peak of the PPG signal as measured at the back of the cavum concha (e.g., deployed surface of first physiological sign portion 110); and (5) calculate PTT as the time difference between the peak of the BCG signal and the peak of the PPG signal as measured at the back of the cavum concha (e.g., deployed surface of first physiological sign portion 110).

In various embodiments, PIR, the subject's physical characteristics, parameters, and their biometrics are used in all five (5) PTT methods. In various embodiments, if no motion associated with subject physical activity has been detected since the last evaluation cycle, equal priority is given to each of the PTT methods that are available. In various embodiments, some PTT methods may not be available in any given evaluation cycle (e.g., due to signal acquisition errors for a given metric, outside interference, etc.) and are weighted as zero. In various embodiments, if motion indicative of physical activity has been detected since the last evaluation cycle, those methods that rely on ECG or ECG R-peak data will be weighted lower since motion errors are known to complicate the acquisition of ECG data. In various embodiments, based on the intensity of the detected motion from 0-10 on a relative index, methods 1, 2, and 3 are weighted down by the value of the relative index, and methods 4 and 5 are similarly weighted up. For example, if no motion is detected, all 5 PTT calculation methods may have an equal weight of 20%. Then, for example, if a relative motion index of 5 is recorded since the last evaluation cycle, methods 1, 2, and 3 may be weighted at 15% and methods 4 and 5 may be weighted at 27.5%. If, for example, in any given evaluation cycle, the physical arrival of the pulse wave was not available or undetectable, methods 3 and 4 would be reduced to a weight of 0%, and the remaining 3 methods would all start at 33.3% weight and then be evaluated for relative motion. For example, if a case existed where physical pulse arrival was undetectable, and a relative motion index of 5 is recorded since the last evaluation cycle, the 5 PTT methods may have a weighting of: (1) ECG-PPG: 28.3%; (2) ECG-BCG: 28.3%; (3) ECG-Physical Pulse Arrival: 0%; (4) Physical Pulse Arrival-PPG: 0%; and (5) BCG-PPG: 43.3%.

In various embodiments, the Pulse Transit Time methods are then weighted against the Pulse Wave methods, taking motion into account. In various embodiments, machine learning can then be performed on the weighted, final values, and on the mean arterial pressure (MAP), systolic, and diastolic values calculated based on each of the 6 methods. In some embodiments, machine learning can also be performed on the PPG waveform, ECG waveform, heart rate, pulse oximetry ($SpO_2$), respiratory rate, accelerometer data, the subject's physical activity metric, population correlation data, and/or the patient's physical characteristics, parameters, and biometrics.

In various embodiments, the blood pressure calculations for a subject in motion technique are performed without calibration. In various embodiments, calibrations are used to further refine the blood pressure calculations for a subject in motion. In various embodiments, performing at least five (5) sphygmomanometer tests, while the enhanced monitoring device and/or system described herein calculates PTT, provides the device/system with regression values as part of the correlation data, which the device and/or system may use and re-use on other enhanced monitoring devices and for other subjects.

At block 820, a determination is made as to whether the signals include environmental data. If the received electronic signals do not include environmental data, at block 805, the method returns to block 800. If the received electronic signals include environmental data, at block 821-825, a determination is made as to the type of environmental data in the received electronic signals. At block 825, if the received electronic signals for an environment around a respective subject include ambient pressure data for the environment, program code executable by the processor will generate respective machine readable values indicative of ambient pressure for the respective subject using the received electronic signals at block 836. At block 821, if the received electronic signals for an environment around a respective subject include ambient light data for the environment, program code executable by the processor will generate respective machine readable values indicative of ambient light for the respective subject using the received electronic signals at block 836, and provide another input to, for example, generate respective machine readable values indicative of pulse oximetry for the respective subject at block 835. At block 822, if the received electronic signals for an environment around a respective subject include UV index data for the environment, program code executable by the processor will generate respective machine readable values indicative of UV index for the respective subject using the received electronic signals at block 836. At block 823, if the received electronic signals for an environment around a respective subject include ambient temperature data for the environment, program code executable by the processor will generate respective machine readable values indicative of ambient temperature for the respective subject using the received electronic signals at block 836, and/or provide another input to, for example, generate respective machine readable values indicative of body/skin/cranial temperature for the respective subject at block 835. At block 824, if the received electronic signals for an environment around a respective subject include humidity data for the environment, program code executable by the processor will generate respective machine readable values indicative of humidity for the respective subject using the received electronic signals at block 836, and/or provide another input to, for example, generate respective machine readable values indicative of liquid indication value for the respective subject at block 858. At block 826, if the received electronic signals for an environment around a respective subject include altitude data for the environment, program code executable by the processor will generate respective machine readable values indicative of altitude for the respective subject using the received electronic signals at block 836.

Referring now to FIG. 8B, at block 851, a determination is made as to whether the signals include respective location data for the subjects. If the received electronic signals do not include location data, at block 805, the method returns to block 800. At block 825, if the received electronic signals include respective location data for a subject, program code executable by the processor will determine a distance between the respective subject and the user of the mobile communication and display device, and generate respective machine readable values indicative of location for the respective subject using the received electronic signals at block 834. At block 852, a determination is made as to whether the signals include respective movement data for one or more of the subjects. If the received electronic signals do not include movement data, at block 805, the method returns to block 800. At block 852, if the received electronic signals include respective movement data for a respective subject, program code executable by the processor will generate respective machine readable values indicative of movement for the respective subject using the received electronic signals at block 834. At block 853, a determination is made as to whether the signals include respective battery life status data for each of the monitoring devices. If the received electronic signals do not include battery life status data, at block 805, the method returns to block 800. At block 853, if the received electronic signals include respective battery life status data for a monitoring device, program code executable by the processor will generate respective machine readable values indicative of battery life status data for the corresponding subject using the received electronic signals at block 834. At block 854, a determination is made as to whether the signals include respective orientation data for each of the subjects. If the received electronic signals do not include orientation data, at block 805, the method returns to block 800. At block 854, if the received electronic signals include respective orientation data for a subject, program code executable by the processor will generate respective machine readable values indicative of orientation for the subject using the received electronic signals at block 834. At block 855, a determination is made as to whether the signals include respective signal strength data for each of the monitoring devices. If the received electronic signals do not include signal strength data, at block 805, the method returns to block 800. At block 855, if the received electronic signals include respective signal strength data for a monitoring device, program code executable by the processor will generate respective machine readable values indicative of signal strength data for the corresponding subject using the received electronic signals at block 834.

Referring now to FIG. 8C, at block 856, a determination is made as to whether the signals include respective pain index data for each of the subjects. If the received electronic signals do not include pain index data, at block 805, the method returns to block 800. At block 856, if the received electronic signals include respective pain index data for a subject, program code executable by the processor will generate respective machine readable values indicative of pain index data for the subject using the received electronic signals at block 839. At block 857, a determination is made as to whether the signals include respective sound data for each of the subjects. If the received electronic signals do not include sound data, at block 805, the method returns to block 800. At block 857, if the received electronic signals include respective sound data for a subject, program code executable by the processor will generate respective machine readable values indicative of sound data for the subject using the received electronic signals at block 837. At block 858, a determination is made as to whether the signals include respective liquid indication data for each of the subjects. If the received electronic signals do not include liquid indication data, at block 805, the method returns to block 800. At block 858, if the received electronic signals include respective liquid indication data for a subject, program code executable by the processor will generate respective machine readable values indicative of liquid indication data for the subject using the received electronic signals, any received input of received electronic signals indicative of humidity data, at block 838. At block 859, a determination is made as to whether the received electronic signals include respective motion data from both the first portion (e.g., 110) and the second portion (e.g., 120) of the monitoring device for a subject. If the received electronic signals do not include respective motion data from both the first and second portions of the monitoring device, at block 805, the method returns to block 800. At block 859, in various embodiments, if the received electronic signals do include respective motion data from both the first portion (e.g., 110) and the second portion (e.g., 120) of the monitoring device for a subject, program code executable by the processor may provide a motion correction signal, or a filtered motion signal, to block 814 to filter out motion errors in the respective motion sensor of the respective first portion of the respective monitoring device while a monitored subject 100 is moving (as described above). At block 859, in various embodiments, if the received electronic signals do include respective motion data from both the first portion (e.g., 110) and the second portion (e.g., 120) of the monitoring device for a subject, program code executable by the processor may generated respective machine readable values indicative of motion errors using the received electronic signals for calibrating and/or correcting generated machine readable values for various physiological signs which use motion data (block 814) as an input (e.g., blood pressure, mean arterial blood pressure, systolic blood pressure, diastolic blood pressure, pulse transit time, pulse wave velocity, R-J interval, respiratory rate, maximal oxygen uptake, stress level, subject activity level, coughing, sneezing, arterial characteristics). For example, the generated electronic motion correction signals, generated electronic filtered motion signals, and/or respective machine readable values indicative of motion errors, may be used to double-check heart rate calculations from the PPG values (block 811), to double-check respiratory rate calculations from the PPG values (block 811) and ECG values (block 815), to double-check blood pressure calculations using the combination of PPG values (block 811), ECG values (block 815), and BCG values (block 812) (as described above).

Referring back to FIG. 8A, at block 840, prognosis engine 550 determines whether the respectively generated machine readable values indicative of the physiological and environmental parameters are greater than respective predetermined severity thresholds (e.g., in severity threshold 559) for the physiological and environmental parameters. At block 811, if a respectively generated machine readable value indicative of a physiological or environmental parameter is less than a respective predetermined severity threshold (e.g., in severity threshold 559) for the physiological or environmental parameter, then prognosis engine 550 generates a first severity score for the physiological or environmental parameter and the corresponding subject. At block 842, if a respectively generated machine readable value indicative of a physiological or environmental parameter is greater than a respective predetermined severity threshold (e.g., in severity threshold 559) for the physiological or environmental parameter, then prognosis engine 550 generates a second severity score for the physiological or environmental parameter and the corresponding subject. For example, if a respectively generated machine readable value indicative of pulse oximetry is less than a respective predetermined severity threshold for pulse oximetry, then prognosis engine 550 generates a first severity score for pulse oximetry and the corresponding subject by performing a predetermined operation (e.g., addition, subtraction, multiplication, division, etc.) of a predetermined amount on the pulse oximetry value. Additionally, by way of example, if a respectively generated machine readable value indicative of pulse oximetry is greater than a respective predetermined severity threshold for pulse oximetry, then prognosis engine 550 generates a second severity score for pulse oximetry and the corresponding subject by performing the same or another predetermined operation (e.g., addition, subtraction, multiplication, division, etc.) of a different predetermined amount on the pulse oximetry value.

In various embodiments, prognosis engine 550 determines whether the respectively generated machine readable values indicative of the physiological and environmental parameters and respectively cached machine readable values indicative of the physiological and environmental parameters are greater than respective predetermined severity thresholds (e.g., in severity threshold 559) for the physiological and environmental parameters. For example, if the respectively generated, and respectively cached, machine readable values indicative of a trend in pulse oximetry is less than a respective predetermined severity threshold for a trend in pulse oximetry, then prognosis engine 550 generates a first severity score for pulse oximetry and the corresponding subject by performing a predetermined operation (e.g., addition, subtraction, multiplication, division, etc.) of a predetermined amount on the pulse oximetry value. Additionally, by way of example, if the respectively generated, and respectively cached, machine readable values indicative of a trend in pulse oximetry is greater than a respective predetermined severity threshold for a trend in pulse oximetry, then prognosis engine 550 generates a second severity score for pulse oximetry and the corresponding subject by performing the same or another predetermined operation (e.g., addition, subtraction, multiplication, division, etc.) of a different predetermined amount on the pulse oximetry value.

Referring back to FIG. 8B, at block 845, prognosis engine 550 determines whether the respectively generated machine readable values indicative of the parameters at block 834 are greater than respective predetermined severity thresholds (e.g., in severity threshold 559) for such parameters. At block 843, if a respectively generated machine readable value indicative of a parameter at block 834 is less than a respective predetermined severity threshold (e.g., in severity threshold 559) for the parameter, then prognosis engine 550 generates a first severity score for the parameter and the corresponding subject. At block 842, if a respectively generated machine readable value indicative of a parameter at block 834 is greater than a respective predetermined severity threshold (e.g., in severity threshold 559) for the parameter, then prognosis engine 550 generates a second severity score for the parameter and the corresponding subject. For example, if a respectively generated machine readable value indicative of distance between a subject and a user of mobile communication and display device is less than a respective predetermined severity threshold for such distance, then prognosis engine 550 generates a first severity score for such distance and the corresponding subject by performing a predetermined operation (e.g., addition, subtraction, multiplication, division, etc.) of a predetermined amount on the generated distance value. Additionally, for example, if a respectively generated machine readable value indicative of such distance is greater than a respective predetermined severity threshold for such distance, then prognosis engine 550 generates a second severity score for such distance and the corresponding subject by performing the same or another predetermined operation (e.g., addition, subtraction, multiplication, division, etc.) of a different predetermined amount on the generated distance value. For example, if a respectively generated machine readable value indicative of orientation is of a first particular type (e.g., lying face down), then prognosis engine 550 generates a first severity score for such orientation and the corresponding subject by performing a predetermined operation (e.g., addition, subtraction, multiplication, division, etc.) of a predetermined amount on the generated orientation value. Additionally, for example, if a respectively generated machine readable value indicative of orientation is of a second particular type (e.g., standing), then prognosis engine 550 generates a second severity score for such orientation and the corresponding subject by performing the same or another predetermined operation (e.g., addition, subtraction, multiplication, division, etc.) of a different predetermined amount on the generated orientation value.

In various embodiments, prognosis engine 550 determines whether the respectively generated machine readable values indicative of a parameter (e.g., orientation, movement, location) and respectively cached machine readable values indicative of the parameter are greater than respective predetermined severity thresholds (e.g., in severity threshold 559) for the parameter. For example, if the respectively generated, and respectively cached, machine readable values indicative of a trend in orientation is of a first trending type (e.g., standing up to laying face up), then prognosis engine 550 generates a first severity score for such trend in orientation and the corresponding subject by performing a predetermined operation (e.g., addition, subtraction, multiplication, division, etc.) of a predetermined amount on the generated orientation value. Additionally, for example, if the respectively generated, and respectively cached, machine readable values indicative of a trend in orientation is of a second particular type (e.g., lying face down to sitting up), then prognosis engine 550 generates a second severity score for such trend in orientation and the corresponding subject by performing the same or another predetermined operation (e.g., addition, subtraction, multiplication, division, etc.) of a different predetermined amount on the generated orientation value.

Referring back to FIG. 8C, at block 849, prognosis engine 550 determines whether the respectively generated machine readable values indicative of pain index are greater than respective predetermined severity thresholds (e.g., in severity threshold 559) for pain index. At block 849, if a respectively generated machine readable value indicative of pain index is less than a respective predetermined severity threshold (e.g., in severity threshold 559) for pain index, then the method returns to block 800 at block 805. At block 849, if a respectively generated machine readable value indicative of pain index is greater than a respective predetermined severity threshold (e.g., in severity threshold 559) for pain index, then prognosis engine 550 generates a respective weighting factor for pain index and the corresponding subject. At block 847, prognosis engine 550 determines whether the respectively generated machine readable values indicative of sound indicates one or more of a predetermined sound type (e.g., a scream). At block 847, if a respectively generated machine readable value indicative of sound does not indicate one or more of the predetermined sound types, then the method returns to block 800 at block 805. At block 847, if a respectively generated machine readable value indicative of sound indicates one or more of the predetermined sound types, then prognosis engine 550 generates a respective weighting factor for the predetermined sound type and the corresponding subject. At block 847, prognosis engine 550 determines whether the respectively generated machine readable values indicative of liquid indicates excessive bleeding. At block 848, if a respectively generated machine readable value indicative of liquid does not indicate excessive bleeding, then the method returns to block 800 at block 805. At block 848, if a respectively generated machine readable value indicative of liquid indicates excessive bleeding, then prognosis engine 550 generates a respective weighting factor for the indication of excessive bleeding and the corresponding subject.

In various embodiments, prognosis engine 550 determines whether the respectively generated machine readable values indicative of a parameter (e.g., liquid, sound) and respectively cached machine readable values indicative of the parameter are greater than respective predetermined severity thresholds (e.g., in severity threshold 559) for the parameter. For example, if the respectively generated, and respectively cached, machine readable values indicative of a trend in liquid (e.g., no change in liquid indicated) are less than a respective predetermined severity threshold for a trend in liquid, then prognosis engine 550 returns the method to block 800. Additionally, by way of example, if the respectively generated, and respectively cached, machine readable values indicative of a trend in liquid (e.g., increasing amount of liquid indicated) is greater than a respective predetermined severity threshold for a trend in liquid, then prognosis engine 550 generates a respective weighting factor for the indication of the trend in liquid and the corresponding subject.

Figure 9:
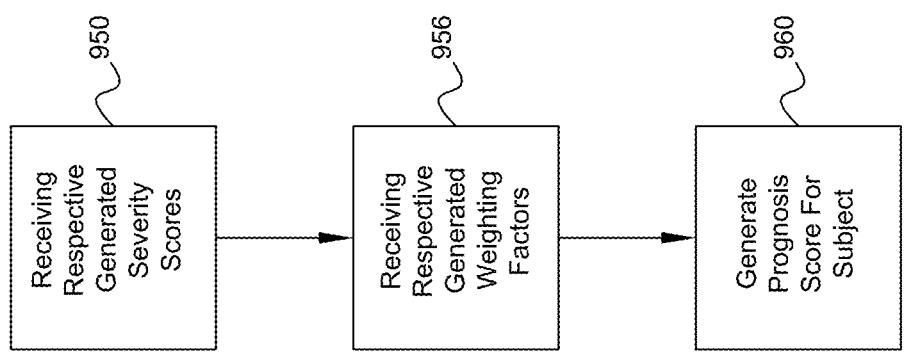
FIG. 9 is a flow chart illustrating a computer-implemented method of automated triage prioritization according to some embodiments.
Figure 10:
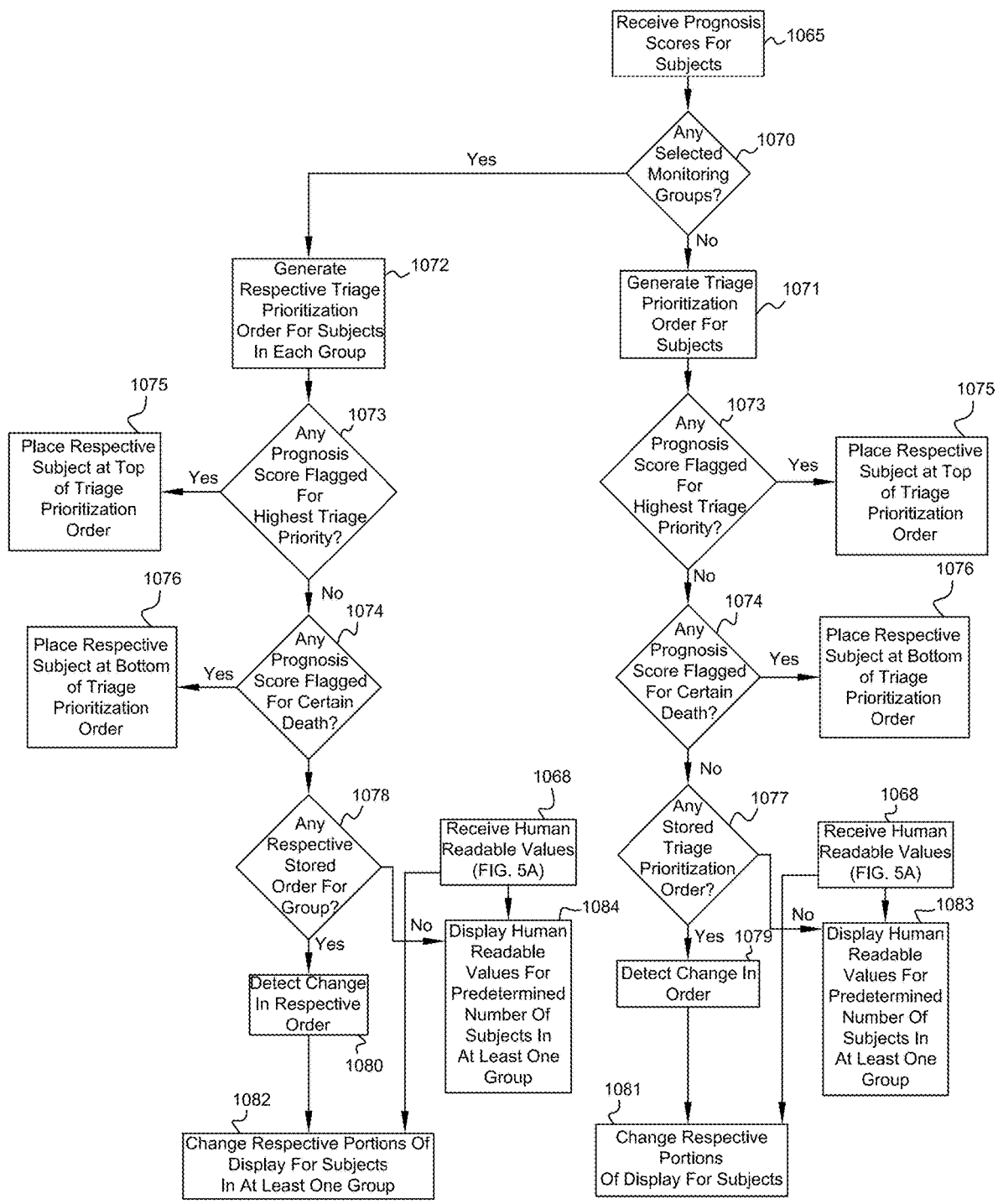
FIG. 10 is a flow chart illustrating a computer-implemented method of automated triage prioritization in accordance with some embodiments of the present subject matter.

Referring now to FIGS. 9-10, computer-implemented methods of automated triage prioritization are provided. At block 950, prognosis engine 550 receives respective generated severity scores (at blocks 844, 843, 811, 842) for each of the plurality of subjects 500-N. At block 950, prognosis engine 550 receives respective generated weighting factors (at block 855, weighting factor module 558) for each of the plurality of subjects 500-N. At block 950, prognosis engine 550 generates respective prognosis scores for each of the plurality of subjects 500-N using the generated respective severity scores and the received plurality of predetermined weighting factors. At block 1065, triage prioritization engine 560-A receives the generated prognosis scores for each of the plurality of subjects 500-N from the prognosis engine 550. At block 1068, triage prioritization engine 560-A receives the respectively generated human readable values for each of the subjects (blocks 835, 832) At block 1070, triage prioritization engine 560-A determines whether there are any selected monitoring groups (e.g., two or more subjects within a predetermined distance of location A, two or more subjects within a predetermined distance of location B, two or more subjects whose physiological and/or environmental parameters are received from a monitoring device hub (e.g., 510) and/or a relay network device 505). At block 1071, if triage prioritization engine 560-A determines that there are no selected monitoring groups, then triage prioritization engine 560-A generates a triage prioritization order of the subjects (e.g., subject-8 triage priority 1, subject-3 triage priority 2, subject-1 triage priority 3, etc.) using the generated prognosis scores.

In various embodiments, prognosis engine 550 may flag a subject's prognosis score for highest or lowest triage priority. In various embodiments, prognosis engine 550 may flag a subject's prognosis score for highest or lowest triage priority using the generated, and/or cached, machine readable values, severity scores, and/or weighting factors. For example, prognosis engine 550 may flag a subject's prognosis score for highest triage priority if the generated prognosis score indicates severe heart beat issues, severe breathing issues, or quick operations. For example, prognosis engine 550 may flag a subject's prognosis score for lowest triage priority if the generated prognosis score indicates that there is a greater than a predetermined probability threshold that the subject is certain to die. In various embodiments, prognosis engine 550 may place subjects on a black list (and cache such black list) if the generated prognosis score indicates that there is a greater than a predetermined probability threshold that each such subject is certain to die. At blocks 1073 and 1074, triage prioritization engine 560-A determines whether any prognosis scores have been flagged for highest or lowest triage priority respectively. If triage prioritization engine 560-A determines a subject's prognosis scores has been flagged for highest triage priority, at block 1075, triage prioritization engine 560-A will select the subject for the highest triage priority position in the generated triage prioritization order. If triage prioritization engine 560-A determines a subject's prognosis scores has been flagged for lowest triage priority, at block 1076, triage prioritization engine 560-A will select the subject for the lowest triage priority position in the generated triage prioritization order.

At block 1077, triage prioritization engine 560-A determines whether a triage prioritization order for the subjects is cached in memory of the mobile communication and display device. If triage prioritization engine 560-A determines that there is no cached triage prioritization order for the subjects, at block 1083, triage prioritization engine 560-A will interface with subject monitoring cores 540-N and user interface 545 (and/or communication interface B 547, command center server 580 and user interface 575) to display the generated respective human readable values for at a predetermined number (e.g., 2, 4, 6) of the subjects on respective portions of the user interface 545 based on the generated triage prioritization order. For example, if triage prioritization engine 560-A determines that there is no cached triage prioritization order for the subjects, triage prioritization engine 560-A will interface with subject monitoring cores 540-N and user interface 545, to display the generated respective human readable values for the subject with the determined highest triage priority in a top portion of the user interface 545, for the subject with the determined second highest triage priority in a portion of the user interface 545 below the top portion, for the subject with the determined third highest triage priority in portion of the user interface 545 below the portion displaying the generated respective human readable values for the subject with the second highest triage priority, and so on.

At block 1077, if triage prioritization engine 560-A determines that there is a cached triage prioritization order for the subjects, triage prioritization engine 560-A will detect whether there is a change between the generated and cached triage prioritization orders for the subjects at block 1079. If triage prioritization engine 560-A does not detect a change between the generated and cached triage prioritization orders for the subjects, triage prioritization engine 560-A will interface with subject monitoring cores 540-N and user interface 545, to update the displays of the generated respective human readable values for the subjects. At block 1081, if triage prioritization engine 560-A does detect a change between the generated and cached triage prioritization orders for the subjects, triage prioritization engine 560-A will interface with subject monitoring cores 540-N and user interface 545, to change the respective portions of the display of the respective generated human readable values for the subjects based on the detected change in the triage prioritization order. For example, if triage prioritization engine 560-A detects a change in the triage prioritization order for subject-3 and subject-8 based on the stored (e.g., cached) prognosis scores for subject-3 and subject-8, the received generated respective new prognosis score for subject-3 and subject-8 (block 1065), and the stored (e.g., cached) triage prioritization order; triage prioritization engine 560-A will interface with subject monitoring cores 540-N and user interface 545, to change the respective portions of the display of the respective generated human readable values for subject-3 and subject-8.

At block 1072, triage prioritization engine 560-A interfaces with subject monitoring cores 540-N and user interface 545 (and/or communication interface B 547, command center server 580 and user interface 575) to display the generated respective human readable values for at a predetermined number (e.g., 2, 4, 6) of the subjects on respective portions of the user interface 545 based on the generated triage prioritization order. For example, if triage prioritization engine 560-A determines that there is no cached triage prioritization order for the subjects, triage prioritization engine 560-A will interface with subject monitoring cores 540-N and user interface 545, to display the generated respective human readable values for the subject with the determined highest triage priority in a top portion of the user interface 545, for the subject with the determined second highest triage priority in a portion of the user interface 545 below the top portion, for the subject with the determined third highest triage priority in portion of the user interface 545 below the portion displaying the generated respective human readable values for the subject with the second highest triage priority, and so on. In various embodiments, display 1110 may be programmed (as described below) to automatically shrink and/or minimize the display for subjects with the lowest triage priority, or lower than a predetermined number (e.g., 4, 6), on user interface 545.

At block 1072, if triage prioritization engine 560-A determines that there are at least two selected monitoring groups (e.g., monitoring group A and monitoring group B), then triage prioritization engine 560-A and triage prioritization engine 560-B generated a triage prioritization order of the subjects in each of the monitoring groups A and B as described above for block 1071. In various embodiments, if different mobile communication display devices 537 are monitoring respective subjects in different monitoring groups (e.g., monitoring group A is monitored by device 537-A and monitoring group B is monitored by device 537-B), prognosis engine 550 may store (e.g., cache) prognosis stores for subjects in the different monitoring groups in memory of both devices 537 and program code on each such device may default the prognosis scores for the different monitoring group (e.g., monitoring group B) on the device 537 principally monitoring the other monitoring group (e.g., device 537-A) to an ignore list. At blocks 1073 and 1074, triage prioritization engine 560-A and triage prioritization engine 560-B respectively determine whether any prognosis scores in each respective monitoring group A and B have been flagged for highest or lowest triage priority respectively as described above for blocks 1073 and 1074. If either of triage prioritization engine 560-A or triage prioritization engine 560-B determines a subject's prognosis scores in the respective monitoring group has been flagged for highest triage priority, at block 1075, the respective triage prioritization engine 560 will select the subject for the highest triage priority position in the generated triage prioritization order for the selected monitoring group as described above for block 1075. If either of triage prioritization engine 560-A or triage prioritization engine 560-B determines a subject's prognosis scores in the respective monitoring group has been flagged for lowest triage priority, at block 1076, the respective triage prioritization engine 560 will select the subject for the lowest triage priority position in the generated triage prioritization order for the selected monitoring group as described above for block 1075.

At block 1078, triage prioritization engine 560-A and triage prioritization engine 560-B each determine whether a triage prioritization order for the subjects in each respective monitoring group is cached in memory of the mobile communication and display device as described above for block 1077. At block 1078, if either of triage prioritization engine 560-A or triage prioritization engine 560-B determines that there is no cached triage prioritization order for the subjects in the respective monitoring group, at block 1084, the respective triage prioritization engine 560 will interface with subject monitoring cores 540-N and user interface 545 (and/or communication interface B 547, command center server 580 and user interface 575) to display the generated respective human readable values for a predetermined number (e.g., 2, 4, 6) of the subjects on respective portions of the user interface 545 based on the generated triage prioritization order for the respective monitoring group as described above for block 1083.

At block 1078, if either of triage prioritization engine 560-A or triage prioritization engine 560-B determines that there is a cached triage prioritization order for the subjects in a respective monitoring group, at block 1084, the respective triage prioritization engine 560 will detect whether there is a change between the generated and cached triage prioritization orders for the subjects in the respective monitoring group at block 1080 as described above for block 1079. If triage prioritization engine 560-A does not detect a change between the generated and cached triage prioritization orders for the subjects, triage prioritization engine 560-A will interface with subject monitoring cores 540-N and user interface 545, to update the displays of the generated respective human readable values for the subjects. At block 1082, if either of triage prioritization engine 560-A or triage prioritization engine 560-B determines detects a change between the generated and cached triage prioritization orders for the subjects in a respective monitoring group, the respective triage prioritization engine 560 will interface with subject monitoring cores 540-N and user interface 545, to change the respective portions of the display of the respective generated human readable values for the subjects in the respective monitoring group based on the detected change in the triage prioritization order as described above for block 1081.

Figure 11:
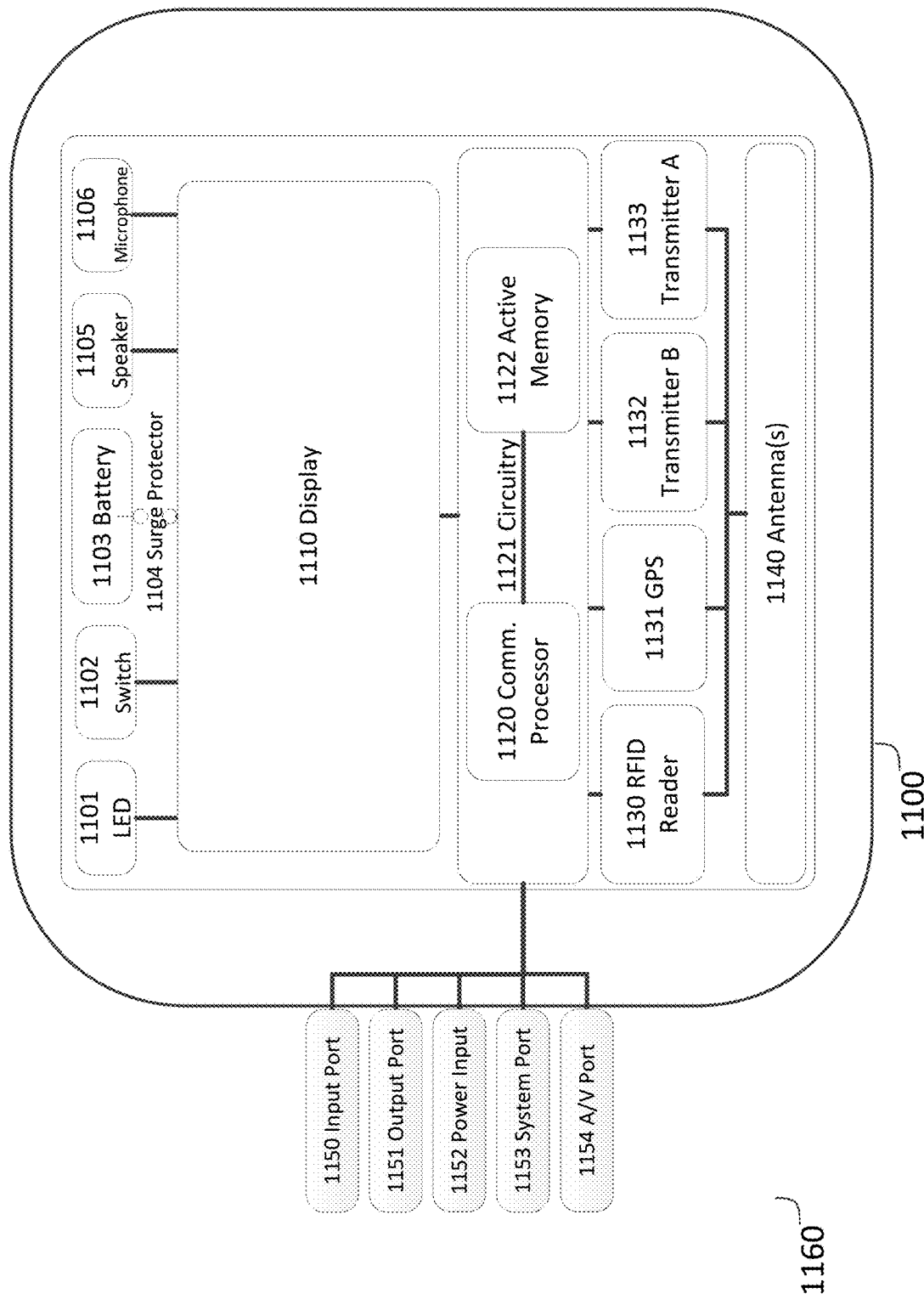
FIG. 11 is a block diagram of an example of a mobile communication and display device in accordance with some embodiments.

FIG. 11 is a block diagram of an example of a mobile communication display device according to some embodiments of the present disclosure. In various embodiments, mobile communication display device 1100 includes electrical components configured to transmit, receive, process, and display data. In various embodiments, mobile communication display device 1100 includes a communications processor 1120 configured to manage the processing and data flow of mobile communication display device 1100. In various embodiments, mobile communication display device 1100 includes an active memory 1122 such as, for example, a memory buffer, configured to hold instructions and data in a cached state for processing, transmission, and presentation purposes. In various embodiments, mobile communication display device 1100 includes circuitry 1121 such as, for example, embedded electronic circuitry configured to connect various components of mobile communication display device 1100 to each other. In various embodiments, RFID reader 1130 includes an RFID reader configured to read unique identification strings of a plurality of enhanced monitoring devices 140. In various embodiments, an RFID tag of each monitoring device 140 broadcasts its respective unique identification string for registration purposes with mobile communication display device 1100. In various embodiments, mobile communication display device 1100 includes a barcode reader 1130, a QR code reader 1130, or any suitable identification code reader 1130, configured to read monitoring devices' respective barcode, QR code, or suitable identification code for registration purposes with mobile communication display device 1100.

In various embodiments, RFID reader 1130 receives a unique identification string of an enhanced monitoring device (140) if such monitoring device (140) is within range of RFID reader 1130 and the RFID reader 1130 has confirmed that the device is a monitoring device (140). In various embodiments, scanning a previously registered monitoring device (140) on mobile communication display device's 1100 RFID reader 830 will automatically re-register this monitoring device (140) to its previously registered subject.

In various embodiments, mobile communication display device 800 includes a location subsystem, such as for example, GPS 831 including a GPS unit configured to use the global GPS network to determine global coordinates within a predetermined tolerance. In various embodiments, location subsystem of mobile communication display device 1100 may include non-GPS protocols (e.g., Galileo, GLONASS, Beidou). In various embodiments, mobile communication display device 1100 includes a transmitter 1132 configured to transmit data received, stored, and/or generated, by mobile communication display device 1100 over a network (e.g., over 802.11, Wi-Fi, 3G/4G/5G cellular, RF, VHF/UHF or other high frequency radio network, satellite network, IP network, a private network, virtual private network (VPN), relay network, the Internet, a Non-secure Internet Protocol Router Network (NIPRNet), a Secret Internet Protocol Router Network (SIPRNet), a Single Channel Ground and Airborne Radio System (SINCGARS), Link-16 (also known as "J2 Coding" or "J2 Messaging" or "TADL" or "SADL"), a cloud computing network, etc.). In various embodiments, this connection could be performed with the inboard connectivity features of the mobile communication and display device. In various embodiments, mobile communication display device 1100 includes a wireless (e.g., Bluetooth, Zigbee, ANT, NFC, near field magnetic induction) transmitter 1133 configured to transmit data over a wireless network including, for example, data transmissions between mobile communication display device and computer software applications, one or more of a plurality of monitoring devices 140, one or more notification devices (not shown), one or more wireless headsets or other audio presentation and recording devices (not shown), and/or other mobile communication and display devices. In various embodiments, a mobile communication and display device of one user (e.g., medic, first responder, physician, fitness supervisor) can communicate with another mobile communication and display device of another user such as, for example, to turnover on-scene duties from the first user to the second user by transmitting subject (500-N), monitoring device (140), and/or environment, data over a wireless (e.g., Bluetooth, NFC, Zigbee, ANT, NFC, near field magnetic induction) network using transmitter 1133, and/or via a software application (e.g., mobile application) operating on both mobile communication and display devices (e.g., Bump application). In various embodiments, RFID reader 1130, GPS 1131, transmitter 1132, and wireless transmitter 1133 are each configured to connect to antenna(s) 1140, such as, for example, a set of antennas for data transmissions. In various embodiments, processor 1120 is configured to control the processing and data flow of various components, subsystems, and modules of mobile communication display device 1100 including, for example, subcomponent LEDs, vibration devices, speakers, microphones, antennas, batteries, surge protectors, etc. In various embodiments, mobile communication display device 1100 is configured to detect available frequencies (e.g., electromagnetic frequencies) and to modify its, and any monitoring devices (140) that it is receiving communications from, transmission protocols to a selected one of a plurality of new frequencies. The inventors have determined that the ability to detect available frequencies, and modify transmission protocols to a selected one of a plurality of new frequencies, is an important feature in situations where radio transmission frequencies are blocked, restricted, or jammed, such as in a battlefield scenario or hospital. The inventors have also determined that, due to the increase in the use of devices that saturate the electromagnetic spectrum on the battlefield and hospitals, in such environments, it may be of vital importance for mobile communication display devices 1100 to have simple logic to exploit open bandwidths for data transmission via frequency hopping especially in battlefield scenarios where different portions of the electromagnetic spectrums are saturated or denied by friendly or enemy forces.

In various embodiments, mobile communication display device 1100 includes a battery 1103 configured to power various components and electronic subsystems of mobile communication display device 1100. For example, battery 1103 may be a long-life battery, and depending on a particular application or environment, may be removable or non-removable. In various embodiments, battery 1103 connects to circuitry 1121 via surge protector 1104 to ensure consistent electrical power flow to various components and electronic subsystems of mobile communication display device 1100 and prevent damage or overheating from short circuits. In various embodiments, mobile communication display device 1100 includes a LED 401 such as, for example, a multi-color LED light, configured to programmatically display different color notifications with different flash patterns, frequencies, and intensities. In various embodiments, mobile communication display device 1100 includes a switch 1102 such as, for example, a multi-positional switch, configured to activate different modes on mobile communication display device 1100, such as, for example, a 2-way communication mode, a 1-way communication mode, a mute or silent mode, a LED active mode, a LED disable mode, a system status mode, a diagnostic mode, etc. In various embodiments, mobile communication display device 1100 includes a speaker 1105 such as, for example, an audio speaker with a programmatic volume setting, a video camera and speaker combination unit configured to simultaneously take audio and video recordings of, for example, the surroundings of mobile communication display device 1100 for remote review or visual teleconference communications. In various embodiments, mobile communication display device 1100 includes a microphone 1106 such as, for example, an audio microphone with a programmatic gain setting. In various embodiments, mobile communication display device 1100 includes a display 1110 such as, for example, a multi-line display configured to display high quality video, graphics, and text.

In various embodiments, mobile communication display device 1100 includes an input port 1150 configured to utilize any suitable wired connection technology to transmit data and electricity, such as, for example, MicroUSB. Any suitable wired connection technology can be utilized by input port 1150. In various embodiments, mobile communication display device 1100 includes an output port 1151 utilizes any suitable wired connection technology to transmit data and electricity, such as, for example, MicroUSB, with other computing devices and network nodes, such as, for example, lightning, 30 pin connectors, USB, Ethernet, parallel connectors, RS-232, MIL-STD-144-114A, or other serial connections. In various embodiments, mobile communication display device 1100 is configured to be powered from its input port 1150, output port 1151, or the dedicated power input 1152 configured to receive suitable electrical inputs, such as, for example, 3V, 12V, 110V, and 220V electrical inputs. In various embodiments, if mobile communication display device 1100 is powered from its input port 1150 or dedicated power input 1152, then mobile communication display device 1100 will supply such power to a downstream device connected to output port 1151. In various embodiments, mobile communication display device 1100 includes a system port 1153 configured to provide diagnostics and upgrades to mobile communication display device 1100. In various embodiments, system port 1153 is a suitable data connection, such as, for example, USB 3.0. In various embodiments, mobile communication display device 1100 is configured to be connected via system port 1153 to other computing devices or to flash drives. In various embodiments, various power connections are configured to be connected via surge protector 1104 to ensure consistent electrical power flow to mobile communication display device 1100 and prevent damage or overheating from short circuits. In various embodiments, mobile communication display device 1100 includes an A/V port 1154 configured to connect mobile communication display device 1100 to A/V devices such as, for example, headsets with over-ear headphones for audio and video with a microphone. In various embodiments, mobile communication display device 1100 includes a side panel 1160 such as, for example, the side panel of mobile communication display device 1100. In various embodiments, side panel 1160 is the location of the external, wired data connection ports.

Figure 12A:
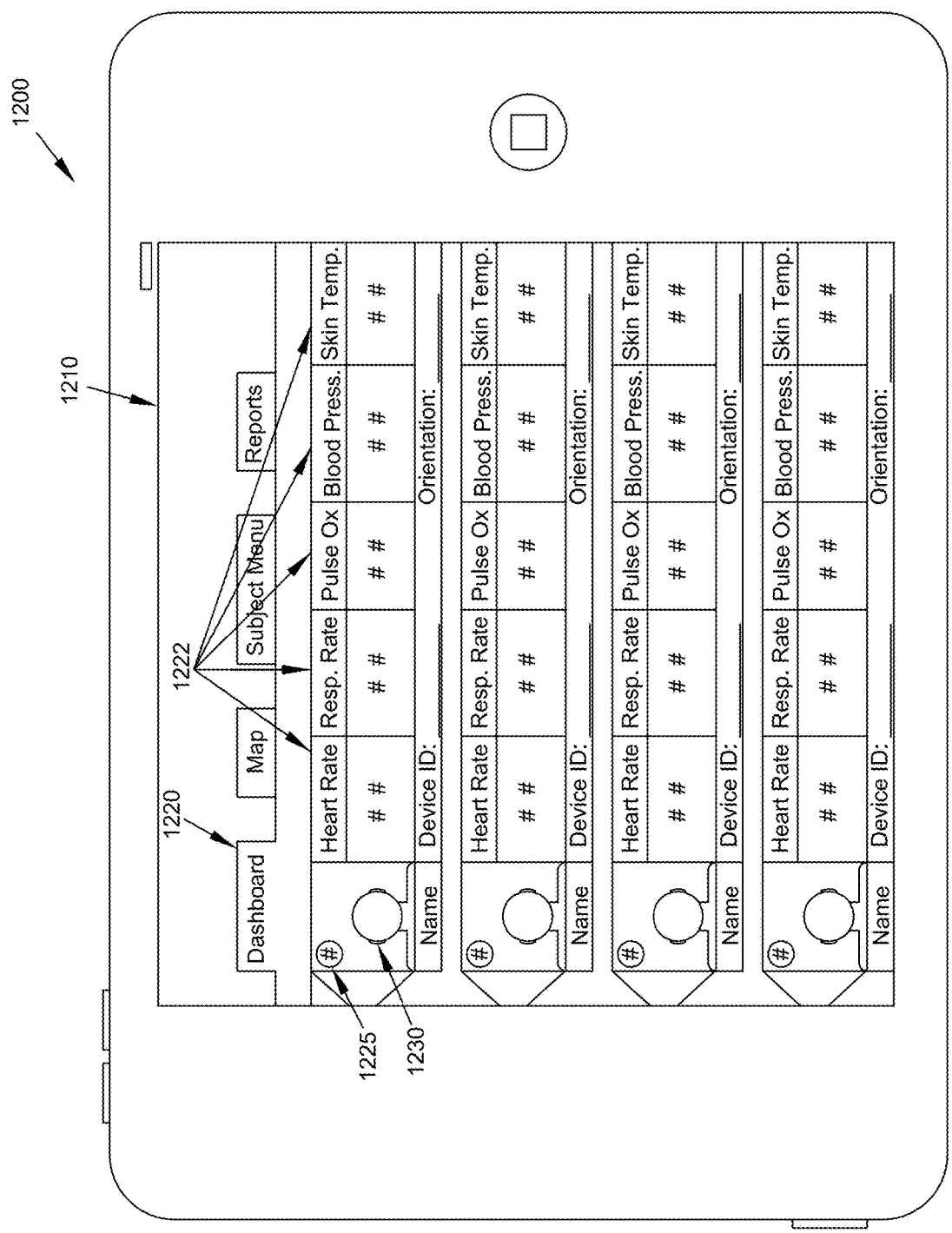
FIGS. 12A-12B are illustrative screenshots of examples of user interfaces of a mobile communication and display device according to some embodiments of the present subject matter.
Figure 12B:
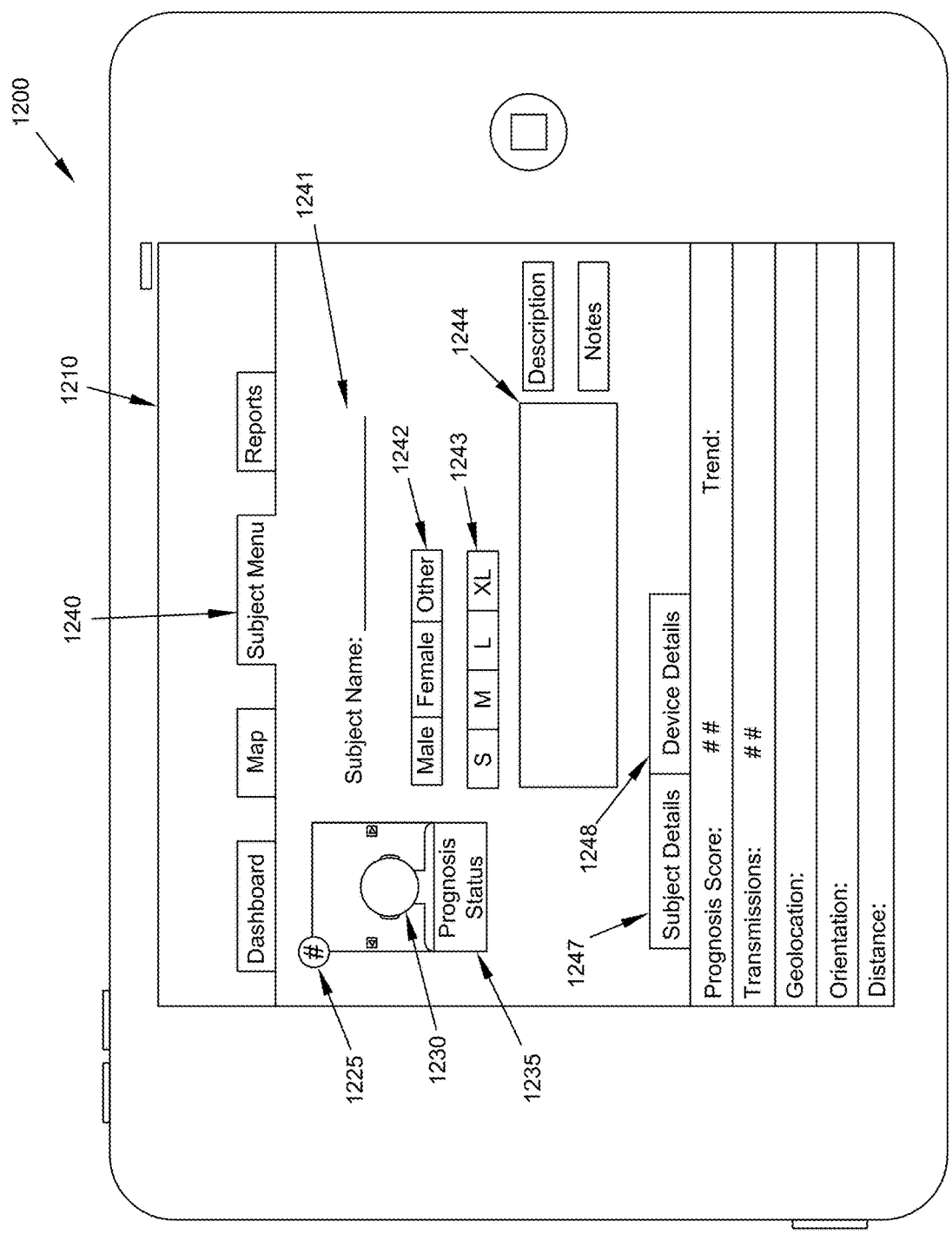

Referring now to FIGS. 12A-12B, illustrative screenshots of examples of user interfaces of a mobile communication and display device according to some embodiments of the present subject matter are provided. In various embodiments, the illustrative screenshots also provide examples of user interfaces of a remote computing device (e.g., 573, 574) for remote administrative and/or medical users. At FIGS. 12A and 12B, illustrative mobile communication and display devices 1200 (and/or remote computing devices) are provided having a user interface according to various embodiments. As shown in FIGS. 12A-12B, a touch-screen display 1210 is provided. In some embodiments, a user (e.g., a first responder, medic, fitness supervisor) can provide input to a processor of a mobile communication and display device 1200 using an input/output device such as, for example a keyboard, pointing device, e.g., a mouse or a trackball, or other kinds of devices for interaction with user interface 1210.

Input from the user can be received in any suitable form, including acoustic, speech, or tactile input. In various embodiments, a user interaction to select one or more of the portions of the display 1210 may be any suitable form of user selection (e.g., open pinch, closed pinch, tap, swipe, double click, keyboard stroke, etc.). In various embodiments, display 1210 may include one or more spin boxes (not shown), or spinners, or scrolls, having an up arrow or a down arrow, to provide the user with an interface to make another type of user selection of a portions of the display. In various embodiments, a type of user selection may be a selection of an up or down arrow of a spin box (not shown). In various embodiments, a type of user selection may be a selection of a scroll (not shown). In various embodiments, a display 1210 may include one or more swipe bars (not shown), having, for example, a right and left swipe bar to provide the user with an interface to make another type of user selection. In various embodiments, a processor of a mobile communication and display device 1200 can support a markup language (e.g., HTML5, HTML4 with jQuery, CSS3, PHP 5.6) including a Drag and Drop API (e.g., native Drag and Drop API) to enable display 1210 to receive a user selection (e.g., a drag tap and hold, a drag click, a drag mouse click, etc.) of information in one portion of display 1210 and execute a Drag and Drop event such that such selected information is dragged over display 1210 and dropped over information in another portion of display 1210 (e.g., may be a Long Touch, or a Long Press, or a Long Click, type of user selection). In various embodiments, a processor of a mobile communication and display device 1200 can support a markup language (e.g., HTML5, HTML4 with jQuery, CSS3, PHP 5.6)) including a Long Touch API programmed to have long touch attributes to implement a Long Touch operation (e.g., LongClick( )) with displayed objects to enable display 1210 to receive a user selection (e.g., a long touch, a long click, a long press, a focus of a cursor over a portion with navigation-keys or a trackball and a long press of an "enter" key or trackball, etc.) of information in one portion of display 1210, receive another selection (e.g., a tap, a touch, a click, a press) of information in another portion of display 1210, and execute a Long Touch event to associate (e.g., pair) the information in the respective portions of display 1210. In various embodiments, display 1210 may include a tactile switch with a long hold to power on/off, and/or switch operating modes of, mobile communication and display device 1200.

In the illustrated embodiments, a mobile communication and display device 1200 including the touch screen display 1210 is provided. In various embodiments, the illustrative screenshots also provide examples of user interfaces of a remote computing device (e.g., 573, 574) including a touch screen display for remote administrative and/or medical users. As described above, mobile communication and display device 1200 may include any suitable device such as, for example, a laptop, a personal computer, a smart phone, a smart watch, a personal digital assistant, a cellular phone, a tablet, an electronic personal planner, a slate tablet, a booklet computer, a convertible notebook, a phablet, a command and control system having a common operational picture (COP) or other situational awareness display, a human-wearable computing device, etc. For example, an illustrative touch-screen display 1210 may be any suitable touch screen display. For example, touch screen display 1210 may be a cathode ray tube (CRT) touch screen display, a liquid crystal touch screen display (LCD), a LCD resistive touch screen display, a LCD capacitive touch screen display, a LCD multi-touch capable touch screen display, etc. In some embodiments, display 1210 is a display that is enabled by an input of the user that is non-tactile.

In the illustrated examples of FIGS. 12A and 12B, display 1210 includes a tab selectable parameter 1220 which enables a user to toggle between displaying a dashboard of subjects (FIG. 5, 500-N), a "map" display (not shown), a subject (FIG. 5, 500-N) display, a reports display, and other suitable displays. In the illustrated embodiments of FIG. 12A, a "dashboard" display is selected at a tab selectable parameter 1220 to display a dashboard of subjects (FIG. 5, 500-N), generated, real-time, human readable values of physiological signs of such subjects (1222), a real-time orientation of such subjects, a triage prioritization order of the respective subjects (1225), descriptive (1230) and/or identifying data of such subjects, identifying information of each corresponding monitoring device, and other suitable information. Any suitable selectable parameter (e.g., inline image) can be provided to toggle between various user interfaces including, for example, a portion to toggle between descriptive data of a subject (1230) and more detailed descriptive data of such subject, a portion to toggle between one or more physiological signs of such subjects (1222) and a historical and/or predictive trend for the one or more physiological signs of such subjects, a portion to toggle between a triage prioritization order of the respective subjects (1225) and a historical triage prioritization order of the respective subjects, playback, video (e.g., with remote physician), help, chat (e.g., with remote physician), etc. user interfaces, and for a user to communicate selected information to a command center (e.g., FIG. 5, 573, 574).

In various embodiments, a "map" display (not shown) is selected at a map selectable parameter/tab to display map data, e.g., map data showing the real-time location of one or more of the monitored subjects, the subjects in one or more monitoring groups, users (e.g., medics, first responders), etc. Various mapping functions can be provided to the user when a "map" display is selected at map selectable parameter/tab including, for example, a zooming function, a panning function (e.g., absolute or relative north, south, east, west, up, down, left, right, etc.), a map type selection (e.g., maps defined by the user for a particular environment, maps with or more overlays, satellite imagery, map grids, navigational charts, etc.) including a drop-down or other selection-type menu (e.g., spin box, text box, etc.), concentric distance circles, and any suitable mapping functions. In various embodiments, maps may be map-based, satellite map-based, topographically based, road-based, or based on custom maps for known areas such as a hospital waiting room. In various embodiments, users, administrators, or medical roles, can select subjects or users on the map for all available detail on that subject or user.

In the illustrated embodiments of FIG. 12B, a "Subject Menu" display is selected at a tab selectable parameter 1240 to display more detailed information regarding a selected subject (FIG. 5, 500-N), descriptive (1230) and/or identifying data of the selected subject (e.g., subject name 1241, subject sex 1242, subject size 1243), a real-time triage prioritization order of the selected subject (1225), a real-time prognosis status (e.g., Critical, Urgent, Routine) for the selected subject, a portion to toggle between subject details (1247) and corresponding monitoring device (1248) details, subject details such as, for example, a real-time prognosis score and trend of the selected subject, real-time number of transmissions received from the monitoring device corresponding to the selected subject, real-time orientation of the selected subject, real-time geolocation of the selected subject, real-time distance of the selected subject from the user of device 1200, corresponding monitoring device (1248) details such as, for example, a patch version of the corresponding monitoring device, an RFID or QR code of the corresponding monitoring device, a real-time battery life (e.g., remaining battery) of the corresponding monitoring device, a real-time signal strength (e.g., RSSI) of the corresponding monitoring device, a real-time operating mode of the corresponding monitoring device, a real-time power mode of the corresponding monitoring device, any real-time error codes of the corresponding monitoring device, real-time environmental parameters measured around the monitoring device, and other suitable information. Any suitable selectable parameter (e.g., inline image) can be provided to toggle between various user interfaces including, for example, a portion to toggle between descriptive data of a selected subject, and descriptive data of another subject, generated, real-time, human readable values of physiological signs of a selected subject, real-time ZMIST MEDEVAC or CASEVAC form data (including data automatically pre-populated by subject monitoring core 540-N (e.g., ID number, method of injury, injury sustained, signs and symptoms, treatment rendered), prognosis engine 550, triage prioritizing engine 560-A), thresholds and/or weighting factors for the selected subject, a map for the selected subject, pictures of the selected subject and his/her injuries and/or environment, a historical triage prioritization order of the selected subject, a historical prognosis of the selected subject, etc.

As shown in FIGS. 12A and 12B, display 1210 can include various menus for selection by the user to display various features provided by subject monitoring core 540-N, prognosis engine 550, triage prioritizing engine 560-A, and/or communication interfaces A 546 and B 547, including, for example, forensics functions to enable the user to interface with prognosis engine 550, triage prioritizing engine 560-A, and/or subject monitoring core 540-N to provide various forensics-based services to the user such as playback services, trend/pattern analysis services (e.g., internal injuries, crashing subjects), etc., entering, editing or modifying data services to enable the user to interface with prognosis engine 550, triage prioritizing engine 560-A, and/or subject monitoring core 540-N to enter, edit or modify data including, for example, descriptive data regarding any of the respective subjects and/or respective monitoring devices, notes or further description (1244), photos, videos, regarding any of the respective subjects, injuries, environment, MEDEVAC or CASEVAC routes, information for any non-automatically pre-populated lines of M.I.S.T. reports, information for any non-automatically pre-populated lines of (9) line MEDEVAC forms, etc., manual assignment of monitoring devices to subjects, manual linking of subjects to medical records, linking of subjects to fitness records, manual adding of a subject, group of subjects, monitoring device, or group of monitoring devices, to an ignore list, manual adding of one or more subjects to a black list, manually modify and/or or override a triage prioritization order, manually modify and/or or override severity thresholds and/or prognosis weighting factors, save subject information to a local memory of monitoring device, activate tactical communication services to enable the user to interface with communication interface B 547, including in connection with prognosis engine 550, triage prioritizing engine 560-A, and/or subject monitoring core 540-N, and one or more command center users via chat, voice communications, etc. to request, view/obtain a status of, and/or call off MEDEVAC or CASEVAC services, receive remote monitoring and care instructions, request linking to medical records of subjects, request linking to fitness records of subjects, real-time data viewing and management services to enable the user to interface with prognosis engine 550, triage prioritizing engine 560-A, and/or subject monitoring core 540-N to view and manage real-time data including, viewing active physiological signs, and/or enlarged physiological graphs, of one or more respective subjects, viewing active status of respective monitoring devices (e.g., malfunctioning sensors, battery life), viewing streaming video of the accident scene, notification services (not shown) to enable the user to interface with communications interface 170, including in connection with prognosis engine 550, triage prioritizing engine 560-A, and/or subject monitoring core 540-N, transfer communication services to enable the user to interface with communication interface B 547, including in connection with prognosis engine 550, triage prioritizing engine 560-A, and/or subject monitoring core 540-N, and one or more other users (e.g., medics, first responders), to transfer data between a device 1200 of one user and another device 1200 of another user such as, for example, during turn-over of an accident scene, and provide various notification services such as real-time alerts for high priority subject prognoses and off-display subject events and triggers. Display 1210 can include any suitable menu for displaying and providing a user interface to one or more services provided on mobile communication and display device 1200.

In various embodiments, the display 1210 includes an interface to securely login to, and be authenticated by, the system such as, for example, via password, speech, or biometrics. In various embodiments, the display 1210 includes an interface for a user to messaging and notification features where users of a mobile communication and display device 1200 (and/or administrators, medical role users, fitness role users of remote computing devices) can communicate with each other via text, voice, video, e-mail, or other suitable communication technique, set configurable alerts for each other, and send/receive medical data on subjects. In various embodiments, the display 1210 includes an interface to a monitoring device registration method, where a user can enter potential subjects' medical and descriptive data beforehand, e.g., before a field operation or rescue attempt. In various embodiments, the user can load the potential subjects' medical and descriptive data from a medical and descriptive data service (e.g., via command center server 580 and subject medical data 571), or the user can retrieve this data from a local cache memory of mobile communication and display device (e.g., via subject medical data module 530), or the user can manually enter such information via the user interface 1210. In various embodiments, user interface 1210 includes a plurality of customization options such as, for example, setting user preferences for display options, alert parameters, status levels on when to set color-coded statuses on a per-subject basis, etc.

FIG. 13 is a block diagram of an example of a monitoring device dispenser unit 1300 in accordance with some embodiments of the present disclosure. In various embodiments, monitoring device dispenser unit 1300 includes electrical components configured to transmit, receive, process, and display data. In various embodiments, monitoring device dispenser unit 1300 includes a communications processor 1320 configured to manage the data flow of monitoring device dispenser unit 1300. In various embodiments, monitoring device dispenser unit 1300 includes an active memory 1322 such as, for example, an active and/or flash memory. In various embodiments, active memory 1322 is a memory buffer configured to hold instructions and data in a cached state for processing, transmission, and presentation purposes. In various embodiments, monitoring device dispenser unit 1300 includes circuitry 1321 such as, for example, embedded electronic circuitry configured to connect various components of monitoring device dispenser unit 1300 to each other. In various embodiments, monitoring device dispenser unit 1300 includes an RFID reader 1330 such as, for example, an RFID reader configured to read monitoring devices' respective unique identification strings. In various embodiments, an RFID tag of each monitoring device 140 broadcasts its respective unique identification string for registration purposes with monitoring device dispenser unit 1300. In various embodiments, monitoring device dispenser unit 1300 includes RFID sensor 1334 such as, for example, a remote RFID reader antenna on the monitoring device dispenser's 1353 portion of the monitoring device dispenser unit 1300. In various embodiments, monitoring device dispenser unit 1300 includes a barcode reader 1330, a QR code reader 1330, or any suitable identification code reader 1330, configured to read monitoring devices' respective barcode, QR code, or suitable identification code for registration purposes with monitoring device dispenser unit 1300. In various embodiments, monitoring device dispenser unit 1300 includes fingerprint 1335 such as, for example, a fingerprint scanner. Any suitable biometric identification reader may be utilized as fingerprint 1335. In various embodiments, monitoring device dispenser unit 1300 includes transmitter 1331 configured to transmitting the data received, stored, and/or generated, by monitoring device dispenser unit 1300 over a network (e.g., over 802.11, Wi-Fi, 3G/4G/5G cellular, RF, VHF/UHF or other high frequency radio network, satellite network, IP network, a private network, virtual private network (VPN), relay network, the Internet, a Non-secure Internet Protocol Router Network (NIPRNet), a Secret Internet Protocol Router Network (SIPRNet), a Single Channel Ground and Airborne Radio System (SINCGARS), Link-16 (also known as "J2 Coding" or "J2 Messaging" or "TADL" or "SADL"), a cloud computing network, etc.). In various embodiments, monitoring device dispenser unit 1300 includes wireless transmitter 1332 (e.g., Bluetooth) configured to transmit data over a wireless network including, for example, data transmissions between monitoring device dispenser unit 1300 and computer software application, one or more of a plurality of monitoring devices 140, one or more notification devices (not shown), one or more wireless headsets or other audio presentation and recording devices (not shown).

In various embodiments, monitoring device dispenser unit 1300 includes LED 1301 such as, for example, a multi-color LED light configured to programmatically display different color notifications with different flash patterns, frequencies, and intensities. In various embodiments, monitoring device dispenser unit 1300 includes a switch 502 such as, for example, a multi-positional switch configured to activate different modes on monitoring device dispenser unit 1300, such as, for example, a video presentation mode, a disabled mode, a communication mode, a LED active mode, a LED disable mode, a system status mode, a diagnostic mode, etc. In various embodiments, monitoring device dispenser unit 1300 includes a speaker 1303 such as, for example, an audio speaker with a programmatic volume setting, a video camera and speaker combination unit configured to simultaneously take audio and video recordings of, for example, the surroundings of monitoring device dispenser unit 1300 for remote review or visual teleconference communications. In various embodiments, monitoring device dispenser unit 1300 includes a microphone 1304 such as, for example, an audio microphone with a programmatic gain setting. In various embodiments, monitoring device dispenser unit 1300 includes a display 1310 such as, for example, a multi-line display configured to displaying high quality video, graphics, and text.

In various embodiments, monitoring device dispenser unit 1300 is configured to be powered from its power input 1341 is configured to be connected via surge protector 1342 to ensure consistent electrical power flow to various components and electronic subsystems of monitoring device dispenser unit 1300 and prevent damage or overheating from short circuits. In various embodiments, monitoring device dispenser unit 1300 includes system port 1340 configured to provide diagnostics and upgrades to monitoring device dispenser unit 1300. In various embodiments, system port 1340 is a suitable data connection such as, for example USB 3.0. In various embodiments, monitoring device dispenser unit 1300 is configured to be connected via system port 1340 to other computing devices or to flash drives. In various embodiments, monitoring device dispenser unit 1300 includes a side panel 1351 such as, for example, the side panel of monitoring device dispenser unit 1300. In various embodiments, side panel 1351 is the location of the external, wired data connection, and power ports, of monitoring device dispenser unit 1300. In various embodiments, monitoring device dispenser unit 1300 includes compartment 1350 configured to be a storage compartment for the monitoring devices. In various embodiments, the monitoring devices are connected via a perforated strip for feeding purposes. In various embodiments, the monitoring devices are loaded into compartment 1350. In various embodiments, compartment 1350 is monitored by one or more of the set of sensors in sensors 1354. In various embodiments, the sensor of the set of sensors that are monitoring compartment 1350 activates motor 1355 within the monitoring device dispenser 1353 assembly. In various embodiments, when requested by a subject or a user (e.g., EMT, first responder, medic) via switch 1302, motor 1355 activates and dispenses a monitoring device. In various embodiments, sensors 1354 included in monitoring device dispenser unit 1300 also include a motion sensor to sense motion (e.g., a waving hand of a subject or a user) underneath the motion sensor of monitoring device dispenser unit 1300, a reader (e.g., a scanner) to read identification card barcodes on the monitoring devices, and/or a reader (e.g., a scanner) to read identification card magnetic stripes on the monitoring devices.

In various embodiments, monitoring device dispenser unit 1300 includes a relay network unit 1370 including electrical components configured to transmit, receive, process, and display data. In various embodiments, relay network unit 1370 includes a communications processor 1380 configured to manage the processing and data flow of relay network unit 1370. In various embodiments, relay network unit 1370 includes active memory 1382 such as, for example, a memory buffer configured to hold instructions and data in a cached state for processing, transmission, and presentation purposes. In various embodiments, relay network unit 1370 includes circuitry 1381 such as, for example, embedded electronic circuitry configured to connect the components of relay network unit 1370 to each other. In various embodiments, relay network unit 1370 includes a location subsystem, such as for example, GPS 1376 including a GPS unit configured to use the global GPS network to determine global coordinates within a predetermined tolerance. In various embodiments, relay network unit 1370 includes a transmitter 1385 configured to transmit the data received, stored, and/or generated, by relay network unit 1370 over a network (e.g., over 802.11, Wi-Fi, 3G/4G/5G cellular, RF, VHF/UHF or other high frequency radio network, satellite network, IP network, a private network, virtual private network (VPN), relay network, the Internet, a Non-secure Internet Protocol Router Network (NIPRNet), a Secret Internet Protocol Router Network (SIPRNet), a Single Channel Ground and Airborne Radio System (SINCGARS), Link-16 (also known as "J2 Coding" or "J2 Messaging" or "TADL" or "SADL"), a cloud computing network, etc.), and/or over a wired connection. In various embodiments, relay network unit 1370 includes wireless (e.g., Bluetooth, Zigbee, ANT, near-field magnetic induction, NFC) transceiver 1386 configured to transmit and receive data over a wireless network including, for example, data transmissions between relay network unit 1370 and computer software applications, one or more mobile communication and display devices, and one or more of a plurality of monitoring devices 140. In various embodiments, GPS 1376, transmitter 1385, and wireless transceiver 1386, are configured to connect to antenna(s) 1387 such as, for example, a set of antennas for data transmissions.

In various embodiments relay network unit 1370 includes a battery 1373 such as, for example, a battery configured to power relay network unit 1370. In various embodiments, battery 1373 is a long-life battery and, depending on application, can be removable or non-removable. In various embodiments, relay network unit 1370 includes battery 1373 configured to connect to circuitry 1381 via surge protector 1374 to ensure consistent electrical power flow to various components and electronic subsystems of monitoring device dispenser unit 1300 and prevent damage or overheating from short circuits. In various embodiments, relay network unit 1370 includes LED 1371 such as, for example, a multi-color LED light that can programmatically display different color notifications with different flash patterns, frequencies, and intensities. In various embodiments, relay network unit 1370 includes keypad 1372 such as, for example, a keyboard with multi-directional buttons that can provide text inputs and activate different modes on relay network unit 1370.

In various embodiments, relay network unit 1370 includes system port 1384 configured to utilize any suitable wired connection technology configured to transmit data and electricity, such as, for example, MicroUSB, with other computing devices and network nodes, such as, for example, Lightning, 30 pin connectors, USB, Ethernet, parallel connections, RS-232, MIL-STD-144-114A, or other serial connections. In various embodiments, transceiver 1386 is configured to transmit and receive data over a wired connection (e.g., to a mobile phone, computer, etc.). In various embodiments, relay network unit 1370 of monitoring device dispenser unit 1300 is configured to be powered, for example, from its system port 1384, battery 1373, or dedicated power input 1383 that is configured to receive suitable electrical inputs such as, for example, 3V, 12V, 110V, and 220V electrical inputs.

As discussed above, in various embodiments, an enhanced monitoring device (e.g., 140) includes a plurality physiological sign portions (e.g., 110, 120) configured for deployment on different, respective surfaces of a subject, and specifically surfaces on the back of an ear, over the mastoid, on the neck of such subject, and skull, nose, or face surfaces opposite a portion of an eyeglasses physiological sign monitoring portion. The inventor observed that such surfaces present challenges to holding each physiological sign portion in place while maintaining that the plane of the sensors within such physiological sign portions is firmly pressed flat against the respective skin surface. In various embodiments, holding a physiological sign portion in place while maintaining that the plane of the sensors within such physiological sign portion is firmly pressed flat against the respective skin surface may be achieved using stretchable bands that loop around body parts for support or stretchable bands that adhere to adhesives. Referring now to FIG. 14, a perspective view illustrating an example of an anchoring mechanism for an example deployment of a physiological sign portion (e.g., 110, 120) of an enhanced monitoring device (e.g., 140) according to some embodiments is provided. As illustrated in FIG. 14, in various embodiments, stretchable, skin-sensitive bands 150 may terminate to adhesive pads 170 that function as anchors when the respective opposing end of each such band 150 is looped around a respective opposing end of a physiological sign portion (e.g., 110) of an enhanced monitoring device 140. In some embodiments, the bands 150 may be permanently attached to the physiological sign portion. In some embodiments, the bands 150 may be permanently attached to a cover or skin that holds the physiological sign portion. In some embodiments, the ends of the bands 150 may be removably secured to the ends of the physiological sign portion for aiding in placement. In various embodiments, one or more stretchable, skin-sensitive bands (not shown) may be configured to loop around body parts of subject 100 for support. For example, a stretchable, skin-sensitive band (not shown) may be deployed around the neck of a subject for the purposes of supporting and immobilizing a physiological sign portion (e.g., 110, 120) at a neck surface (e.g., USP, LSP1, LSP2) of a subject while also maintaining the plane of the sensors within such physiological sign portion firmly pressed flat against such neck surface. In some embodiments, a stretchable, skin-sensitive band (not shown) may be deployed around the earlobe of a subject for the purposes of supporting and immobilizing a physiological sign portion (e.g., 110) at a back-of-the-ear surface (e.g., a surface opposite a concha of a subject) while also maintaining the plane of the sensors within such physiological sign portion firmly pressed flat against such back of the ear surface. In some embodiments, a stretchable, skin-sensitive band (not shown) may be deployed around the head of a subject for the purposes of supporting and immobilizing a physiological sign portion (e.g., 110, 120) at a surface over a mastoid region of the neck of the subject while also maintaining the plane of the sensors within such physiological sign portion firmly pressed flat against such neck surface.

In various embodiments, holding a physiological sign portion in place while maintaining that the plane of the sensors within such physiological sign portion is firmly pressed flat against the respective skin surface may be achieved using adhesive over-the-top of the physiological sign portion, adhesive on a sensor-side surface of the physiological sign portion, and/or physical connections to adhesives, or combinations thereof. In various embodiments, adhesives over-the-top of the physiological sign portion (e.g., 110, 120) may be used and operate similar to a bandage. In various embodiments, the appropriate surface (e.g., opposite a concha, over a mastoid region, USP, LSP1, LSP2, skull, nose, or face surface opposite a portion of an eyeglasses physiological sign monitoring portion) of a subject (e.g., 100) is determined as described herein, a physiological sign portion (e.g., 110, 120) configured for deployment at such surface is placed at such surface, and then an adhesive-laden piece of fabric or other flexible material is placed over its top such that the physiological sign portion is between the adhesive and the skin surface. In various embodiments, the adhesive adheres to the physiological sign portion itself and to the subject's skin, immobilizing the sensor and firmly holding it in place.

FIGS. 15A-15C are perspective views illustrating examples of an adhesive sheet for an example deployment of a physiological sign portion of an enhanced monitoring device in accordance with some embodiments of the present disclosure. The inventor has observed that the holding power of an adhesive is linearly proportional to the area of surface contact. In various embodiments, adhesive cut-outs 1510 may be shaped for deployment on a particular surface of a subject (e.g., 100). In various embodiments, and as illustrated in FIGS. 15A-15C, adhesive cut-outs 1510 shaped as butterfly wings may be used to secure a physiological sign portion (e.g., 110, 120) of an enhanced monitoring device 140 to a surface (e.g., a surface on the back of a left ear) of a subject (e.g., 100). In various embodiments, adhesive cut-outs 1510 shaped as butterfly wings may be used to secure a physiological sign portion (e.g., 110, 120) of an enhanced monitoring device 140 to a surface (e.g., a surface on the back of a right ear, a surface over a mastoid region of the neck of the subject, a surface over another region of the neck of the subject, and a skull, nose, or face surface of the subject opposite a portion of an eyeglasses physiological sign monitoring portion, etc.) of a subject (e.g., 100). In various embodiments, replacement adhesives 1510 (e.g., replacement butterfly-shaped adhesives) may be delivered on a business-card-sized sheet 1500. In various embodiments, a plurality of business-card-sized sheets 1500 may each be disposed on a larger sheet (e.g., on an 8.5×11 inch sheet) (not shown) for use in securing respective physiological sign portions of a plurality of enhanced monitoring devices to respective surfaces of a plurality of subjects. Referring to FIGS. 15A and 15B, a respective pull tab 1530 may be provided to enable the lifting of the respective over-the-top adhesive 1540. With the respective over-the-top adhesive 1540 lifted, a physiological sign portion 110 may be slid into place. Then, referring to FIG. 15C, the over-the-top adhesive 1540 may be returned and affixed to the physiological sign portion 110. Then, the affixed physiological sign portion 110 and adhesive 1540 may be lifted off the card 1550 and applied to the desired surface of subject 100. In various embodiments, the sheet 1500 may also include additional strips of adhesive 1505 to be used for additional securing as needed to particular surfaces of subject 100 In various embodiments, an adhesive on the subject-facing, and physiological sign sensing, surface of a physiological sign portion (e.g., 110, 120) may be used and may act to adhere the surface of the physiological sign portion directly to the subject's skin surface, immobilizing the physiological sign portion. In various embodiments, physical connections (e.g., a snap button) to an adhesive may physically connect a physiological sign portion to an adhesive pad though mechanical, electro-mechanical, or some other compressive or vacuum forces.

In some embodiments, one or more steps of the methods described herein can be implemented by one or more general purpose computers programmed in accordance with the principals discussed herein. In various embodiments, a general computer processor programmed in accordance with various principles described herein is provided in the cloud of a cloud computing environment. In some embodiments, a general computer processor programmed in accordance with various principles is provided at one or more command center servers 580 and/or at an administrator or medical role (573, 574) of the command center services 580. Digital computer systems programmed to perform particular functions pursuant to instructions from program code that implements features of the methods described herein may be special-purpose computers particular to the methods described herein. Computer program code implementing one or more methods described herein may be distributed to users on a non-transient, computer readable storage medium such as, for example, a floppy disk, CD-ROM, or flash memory data storage device, or other suitable distribution storage medium, and may be copied to a hard disk, RAM, or other suitable intermediate, non-transient computer readable storage medium, on a computer. When the programs are to be run, they will be loaded either from their distribution medium or their intermediate storage medium into the execution memory of the computer, configuring the computer to act in accordance with the method of this invention. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features can be described above as acting in certain combinations and even initially claimed as such, one or more features from a claimed combination can in some cases be excised from the combination, and the claimed combination can be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing can be advantageous. Moreover, the separation of various system components in the embodiments described above should not be understood as requiring such separation in all embodiments, and it should be understood that certain of the described program components and systems can generally be integrated together in a single software product being executed in one or more networks or packaged into multiple software products for execution in the one or more networks.

One or more steps of the processes and logic flows described in this specification can be performed by one or more programmable processors executing one or more computer programs to perform functions by operating on input data and generating output. One or more steps of the processes and logic flows can also be performed by, and apparatus can also be implemented as, special purpose logic circuitry, e.g., an FPGA (field programmable gate array) or an ASIC (application specific integrated circuit).

Various embodiments can be implemented in a cloud computing system that includes, and/or is in communication with, a back end component, e.g., as a data server, or that includes a middleware component, e.g., an application server, or that includes a front end component, e.g., a computer having a GUI or a Web browser through which an operator can interact with an implementation of the subject matter described is this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

While various embodiments have been described, it is to be understood that the embodiments described are illustrative only and that the scope of the subject matter is to be accorded a full range of equivalents, many variations and modifications naturally occurring to those of skill in the art from a perusal hereof

What we claim is:

1. A monitoring device, comprising:
a first physiological parameter monitoring portion
configured for deployment on a surface on the back of a respective ear of the subject, or a surface over a mastoid region of the neck of the subject; and
comprising a first plurality of physiological sensors, each of the first plurality of physiological sensors configured to periodically generate respective data based on one or more real-time monitored physiological parameters of the subject, wherein the real-time monitored physiological parameters by the first plurality of physiological sensors of the first physiological parameter monitoring portion comprise photoplethysmogram, electrocardiogram, ballistocardiogram, and at least one of skin conductance or skin resistance, wherein at least one of the first plurality of physiological sensors comprises green and infrared (IR) light emitters and a corresponding light receptor; and
a second physiological parameter monitoring portion:
configured for deployment on a surface over another region of the neck of the subject selected from the group consisting of:
a surface of the neck over top of the pocket formed between the trapezius and the sternocleidomastoid muscles of the subject and under the levator scapulae of the subject;
a surface of the neck over the pocket formed between the posterior scalene and the middle scalene muscles of the subject, and above the trapezius muscle of the subject; and
a surface of the neck over the pocket formed between the middle scalene and the anterior scalene muscles of the subject, and above the trapezius muscle of the subject;
comprising a second plurality of physiological sensors, each of the second plurality of physiological sensors configured to periodically generate respective data based on one or more real-time monitored physiological parameters of the subject, wherein the real-time monitored physiological parameters by the second plurality of physiological sensors of the second physiological parameter monitoring portion comprise electrocardiogram, ballistocardiogram, and at least one of skin conductance or skin resistance;
configured to receive the respective data, periodically generated by the first plurality of physiological sensors, from the first physiological parameter monitoring portion; and
further comprising a processor; and a non-transitory machine-readable storage medium encoded with program code executable by the processor for periodically generating respective values indicative of a plurality of real-time physiological signs for the subject using the received, periodically generated respective data from the first plurality of physiological sensors and the periodically generated respective data from the second plurality of physiological sensors.

2. The monitoring device of claim 1, wherein the deployment surface of the first physiological parameter monitoring portion, and the deployment surface of the second physiological parameter monitoring portion, are at least three inches apart from each other on the subject.

3. The monitoring device of claim 2, wherein:
the first physiological parameter monitoring portion is configured for deployment on the surface on the back of the respective ear of the subject; and
the second physiological parameter monitoring portion is configured for deployment on the surface of the neck over top of the pocket formed between the trapezius and the sternocleidomastoid muscles of the subject and under the levator scapulae of the subject.

4. The monitoring device of claim 2, wherein:
the first physiological parameter monitoring portion is configured for deployment on the surface over the mastoid region of the neck of the subject; and
the second physiological parameter monitoring portion is configured for deployment on the surface of the neck over top of the pocket formed between the posterior scalene and the middle scalene muscles of the subject, and above the trapezius muscle of the subject.

5. The monitoring device of claim 1, wherein at least one of the first and second physiological parameter monitoring portions further comprises a snap button configured to receive a disposable electrode.

6. The monitoring device of claim 1, wherein the plurality of real-time physiological signs for the subject comprise motion-corrected pulse oximetry, at least one of motion-corrected respiratory rate or subject activity level, at least one of motion-corrected heart rate or motion-corrected heart rate variability, at least one of cuffless mean arterial blood pressure, cuffless systolic blood pressure, cuffless diastolic blood pressure or pre-ejection period, and at least one of hydration level, stress level, galvanic skin response, bio-impedance, or carbon dioxide in the subject's blood.

7. The monitoring device of claim 6, wherein the program code executable by the processor of the second physiological parameter monitoring portion for periodically generating values indicative of the plurality of real-time physiological signs for the subject further comprises:
- program code for periodically generating the values indicative of motion-corrected pulse oximetry for the subject using:
  - the periodically generated ballistocardiogram data from each of the first and second physiological parameter monitoring portions;
  - the periodically generated green light data from the at least one of the plurality of physiological sensors of the first physiological parameter monitoring portion; and
  - the periodically generated infrared light data from the at least one of the plurality of physiological sensors of the first physiological parameter monitoring portion as a motion reference.

8. The monitoring device of claim 6, wherein the program code executable by the processor of the second physiological parameter monitoring portion for periodically generating values indicative of the plurality of real-time physiological signs for the subject further comprises:
- program code for periodically generating the respective values indicative of the at least one of motion-corrected respiratory rate or subject activity level for the subject using:
  - the periodically generated ballistocardiogram data from the second physiological parameter monitoring portion;
  - the periodically generated electrocardiogram data, or the periodically generated at least one of skin conductance or skin resistance data, from each of the first and second physiological parameter monitoring portions; and
  - the periodically generated photoplethysmogram data from the first physiological parameter monitoring portion; and
- program code for periodically generating the respective values indicative of the at least one of motion-corrected heart rate or motion-corrected heart rate variability for the subject using:
  - if motion-corrected heart rate for the subject, the periodically generated ballistocardiogram data from each of the first and second physiological parameter monitoring portions, the periodically generated green light data from the at least one of the plurality of physiological sensors of the first physiological parameter monitoring portion, and the periodically generated infrared light data from the at least one of the plurality of physiological sensors of the first physiological parameter monitoring portion as a motion reference; and
  - if motion-corrected heart rate variability for the subject, the periodically generated ballistocardiogram data from each of the first and second physiological parameter monitoring portions, and the periodically generated electrocardiogram data from each of the first and second physiological parameter monitoring portions.

9. The monitoring device of claim 6, wherein the program code executable by the processor of the second physiological parameter monitoring portion for periodically generating values indicative of the plurality of real-time physiological signs for the subject further comprises:
- program code for periodically generating the respective values indicative of the at least one of cuffless mean arterial blood pressure, cuffless systolic blood pressure, cuffless diastolic blood pressure or pre-ejection period for the subject using:
  - if cuffless mean arterial blood pressure, cuffless systolic blood pressure, or cuffless diastolic blood pressure, the periodically generated ballistocardiogram data from at least one of the first and second physiological parameter monitoring portions, the periodically generated electrocardiogram data from the at least one of the first and second physiological parameter monitoring portions, and the periodically generated photoplethysmogram data from the first physiological parameter monitoring portion; and
  - if pre-ejection period, the periodically generated electrocardiogram data from each of the first and second physiological parameter monitoring portions.

10. The monitoring device of claim 9, wherein at least one of the second plurality of physiological sensors comprises a multi-axis accelerometer, wherein the plurality of real-time physiological signs for the subject further comprise at least two of cuffless mean arterial blood pressure, cuffless systolic blood pressure, or cuffless diastolic blood pressure, and wherein the program code for periodically generating the respective values indicative of the at least two of cuffless mean arterial blood pressure, cuffless systolic blood pressure, or cuffless diastolic blood pressure, further performs a weighted averaging of the respective resulting waveforms from each of:
- a pulse wave velocity technique using the periodically generated ballistocardiogram data from the at least one of the first and second physiological parameter monitoring portions and the periodically generated photoplethysmogram data from the first physiological parameter monitoring portion; and
- at least three of five pulse transit time techniques, wherein the five pulse transit time techniques respectively determine pulse transit time using:
  - an R-wave peak of the waveform from the periodically generated electrocardiogram data from the at least one of the first and second physiological parameter monitoring portions, and a peak of the waveform from the periodically generated photoplethysmogram data from the first physiological parameter monitoring portion;
  - an R-wave peak of the waveform from the periodically generated electrocardiogram data from the at least one of the first and second physiological parameter monitoring portions, and a peak of the waveform from the periodically generated ballistocardiogram data from the at least one of the first and second physiological parameter monitoring portions;

a pulse wave arrival time periodically generated by the multi-axis accelerometer of the at least one of the second plurality of physiological sensors, and an R-wave peak of the waveform from the periodically generated electrocardiogram data from the at least one of the first and second physiological parameter monitoring portions;

a pulse wave arrival time periodically generated by the multi-axis accelerometer of the at least one of the second plurality of physiological sensors, and a peak of the waveform from the periodically generated photoplethysmogram data from the first physiological parameter monitoring portion; and a peak of the waveform from the periodically generated ballistocardiogram data from the at least one of the first and second physiological parameter monitoring portions, and a peak of the waveform from the periodically generated photoplethysmogram data from the first physiological parameter monitoring portion.

11. The monitoring device of claim 6, wherein the program code executable by the processor of the second physiological parameter monitoring portion for periodically generating values indicative of the plurality of real-time physiological signs for the subject further comprises:

program code for periodically generating the respective values indicative of the at least one of hydration level, stress level, galvanic skin response, or bioimpedance for the subject, or of carbon dioxide in the subject's blood, using:

if galvanic skin response, bioimpedance, or hydration level for the subject, the periodically generated at least one of skin conductance data or skin resistance data from each of the first and second physiological parameter monitoring portions; and if stress level for the subject,
the periodically generated electrocardiogram data, or the periodically generated at least one of skin conductance or skin resistance data, from each of the first and second physiological parameter monitoring portions; and
the periodically generated photoplethysmogram data from the first physiological parameter monitoring portion; and if carbon dioxide in the subject's blood, the periodically generated values indicative of motion-corrected respiratory rate;
the periodically generated values indicative of motion-corrected pulse oximetry; and
the periodically generated photoplethysmogram data from the first physiological parameter monitoring portion.

12. The monitoring device of claim 11, wherein the real-time monitored physiological parameters by the second plurality of physiological sensors of the second physiological parameter monitoring portion further comprise at least one of sweat chemistry or sweat composition; wherein the plurality of real-time physiological signs for the subject further comprise at least one of hydration level or stress level for the subject;

and wherein the program code executable by the processor of the second physiological parameter monitoring portion for periodically generating the respective values indicative of the at least one of hydration level or stress level further respectively uses the periodically generated at least one of sweat chemistry data or sweat composition data from the second physiological parameter monitoring portion.

13. The monitoring device of claim 6, wherein the real-time monitored physiological parameters by the first plurality of physiological sensors of the first physiological parameter monitoring portion, and the real-time monitored physiological parameters by the second plurality of physiological sensors of the second physiological parameter monitoring portion, further comprise skin temperature; wherein the plurality of real-time physiological signs for the subject further comprise at least one of core body temperature or cranial temperature; and wherein the program code executable by the processor of the second physiological parameter monitoring portion for periodically generating the respective values indicative of the at least one of core body temperature or cranial temperature uses the periodically generated skin temperature data from each of the first and second physiological parameter monitoring portions and the periodically generated values indicative of subject activity level.

14. A system for remote physiological monitoring of subjects, comprising:

a plurality of monitoring devices, each monitoring device comprising:

a respective first physiological parameter monitoring portion
configured for deployment on a surface on the back of a respective ear of a respective subject, or a surface over a mastoid region of the neck of the respective subject; and
comprising a respective first plurality of physiological sensors, each of the first plurality of physiological sensors configured to periodically generate respective data based on one or more real-time monitored physiological parameters of the respective subject, wherein the real-time monitored physiological parameters by the first plurality of physiological sensors of the first physiological parameter monitoring portion comprise photoplethysmogram, electrocardiogram, ballistocardiogram, and at least one of skin conductance or skin resistance, wherein at least one of the first plurality of physiological sensors comprises green and infrared (IR) light emitters and a corresponding light receptor; and a respective second physiological parameter monitoring portion:
configured for deployment on a surface over another region of the neck of the respective subject selected from the group consisting of:
a surface of the neck over top of the pocket formed between the trapezius and the sternocleidomastoid muscles of the subject and under the levator scapulae of the respective subject;
a surface of the neck over the pocket formed between the posterior scalene and the middle scalene muscles of the subject, and above the trapezius muscle of the respective subject; and
a surface of the neck over the pocket formed between the middle scalene and the anterior scalene muscles of the subject, and above the trapezius muscle of the respective subject;
comprising a respective second plurality of physiological sensors, each of the second plurality of physiological sensors configured to periodically generate respective data based on one or more real-time monitored physiological parameters of the respective subject, wherein the real-time monitored physiological parameters by the second plurality of physiological sensors of the second physiological parameter monitoring portion comprise electrocardiogram, ballistocardiogram, and at least one of skin conductance or skin resistance;

configured to respectively receive the respective data, periodically generated by the respective first plurality of physiological sensors, from the respective first physiological parameter monitoring portion of the respective monitoring device; and further comprising a respective processor; and a respective non-transitory machine-readable storage medium encoded with program code executable by the respective processor for periodically generating respective values indicative of a plurality of real-time physiological signs for the respective subject using the received, periodically generated respective data from the respective first plurality of physiological sensors and the periodically generated respective data from the respective second plurality of physiological sensors.

15. The system of claim 14, wherein the respective second physiological parameter monitoring portion of each monitoring device further comprises a transmitter configured to periodically transmit electronic signals over a network, the transmitted electronic signals comprising the periodically generated respective values indicative of the plurality of real-time physiological signs for the respective subject, the system further comprising:
a mobile communication and display device comprising:
a communications interface configured to be coupled to a network and to receive the periodically transmitted electronic signals over the network from each of the respective second physiological parameter monitoring portions of each of the plurality of monitoring devices; and
a processor coupled to the communications interface.

16. The system of claim 15, the mobile communication and display device further comprising a non-transitory machine-readable storage medium encoded with program code executable by the processor for:
periodically generating a respective prognosis score for each of the subjects using the respective values indicative of the plurality of real-time physiological signs for the respective subject in the received, periodically transmitted electronic signals from each of the plurality of monitoring devices; and
periodically generating an alert for at least one of the subjects based on the periodically generated prognosis scores.

17. The system of claim 14, wherein the plurality of real-time physiological signs for the respective subject comprise motion-corrected pulse oximetry, at least one of motion-corrected respiratory rate or subject activity level, at least one of motion-corrected heart rate or motion-corrected heart rate variability, at least one of cuffless mean arterial blood pressure, cuffless systolic blood pressure, cuffless diastolic blood pressure or pre-ejection period, and at least one of hydration level, stress level, galvanic skin response, bioimpedance, or carbon dioxide in the respective subject's blood.

18. A system for remote physiological monitoring of a subject, comprising:
a monitoring device comprising a plurality of physiological parameter monitoring portions, the plurality of physiological parameter monitoring portions comprising:
a first physiological parameter monitoring portion:
configured for deployment on a surface on the back of a respective ear of the subject, or a surface over a mastoid region of the neck of the subject; and
comprising a first plurality of physiological sensors, each of the first plurality of physiological sensors configured to periodically generate respective data based on one or more real-time monitored physiological parameters of the subject, wherein the real-time monitored physiological parameters by the first plurality of physiological sensors of the first physiological parameter monitoring portion comprise photoplethysmogram, electrocardiogram, ballistocardiogram, and at least one of skin conductance or skin resistance, wherein at least one of the first plurality of physiological sensors comprises green and infrared (IR) light emitters and a corresponding light receptor; and
a second physiological parameter monitoring portion:
configured for deployment on a surface over another region of the neck of the subject selected from the group consisting of:
a surface of the neck over top of the pocket formed between the trapezius and the sternocleidomastoid muscles of the subject and under the levator scapulae of the subject;
a surface of the neck over the pocket formed between the posterior scalene and the middle scalene muscles of the subject, and above the trapezius muscle of the subject; and
a surface of the neck over the pocket formed between the middle scalene and the anterior scalene muscles of the subject, and above the trapezius muscle of the subject; and
comprising a second plurality of physiological sensors, each of the second plurality of physiological sensors configured to periodically generate respective data based on one or more real-time monitored physiological parameters of the subject, wherein the real-time monitored physiological parameters by the second plurality of physiological sensors of the second physiological parameter monitoring portion comprise electrocardiogram, ballistocardiogram, and at least one of skin conductance or skin resistance;
configured to receive the respective data, periodically generated by the first plurality of physiological sensors, from the first physiological parameter monitoring portion; and
further comprising:
a processor;
a non-transitory machine-readable storage medium encoded with program code executable by the processor for periodically generating respective values indicative of a plurality of real-time physiological signs for the subject using the periodically generated respective data from the first plurality of physiological sensors and the periodically generated respective data from the second plurality of physiological sensors; and a transmitter configured to periodically transmit electronic signals over a network, the transmitted electronic signals comprising the periodically generated respective values indicative of the plurality of real-time physiological signs for the subject; and a mobile communication and display device comprising:
a communications interface configured to be coupled to the network and to receive the periodically transmitted electronic signals over the network from the second physiological parameter monitoring portion of the monitoring device; and
a processor coupled to the communications interface.

19. The system of claim 18, the mobile communication and display device further comprising a non-transitory machine-readable storage medium encoded with program code executable by the processor for:

periodically generating a prognosis score for the subject using the respective values indicative of the plurality of real-time physiological signs for the subject in the received, periodically transmitted electronic signals from the transmitter of the second physiological parameter monitoring portion of the monitoring device; and periodically generating an alert for the subject based on the periodically generated prognosis score.

20. The system of claim 18, wherein the plurality of real-time physiological signs for the subject comprise motion-corrected pulse oximetry, at least one of motion-corrected respiratory rate or subject activity level, at least one of motion-corrected heart rate or motion-corrected heart rate variability, at least one of cuffless mean arterial blood pressure, cuffless systolic blood pressure, cuffless diastolic blood pressure or pre-ejection period, and at least one of hydration level, stress level, galvanic skin response, bio-impedance, or carbon dioxide in the subject's blood.

* * * * *

UNITED STATES PATENT AND TRADEMARK OFFICE
CERTIFICATE OF CORRECTION

| | |
|---|---|
| PATENT NO. | : 12,089,914 B2 |
| APPLICATION NO. | : 17/026929 |
| DATED | : September 17, 2024 |
| INVENTOR(S) | : Kurt Stump |

Page 1 of 1

It is certified that error appears in the above-identified patent and that said Letters Patent is hereby corrected as shown below:

In the Specification

In Column 27, Please delete Lines 38-49 below:
"conducivetorecordingskinelectricalpropertiessinceskinis
sopliableandflexiblewhilethebodyisinmotion.Also.asfurther
detailedbelow.mostmetalscreateabatterywiththesaltsofthe
skin.whichin-turnproducesfluctuatingandineffectiverea-
ingswhilethischargeegualizationoccursforuptosixtyminutes.
Invariousembodiments.oneormoreofthephysiologicalsign
portions(110.120)ofenhancedmonitoringdevice140are
configuredtousedisposableelectrodes(e.g.•silversilver-chlo-
rideelectrodesincorporatingaflexible.electricallyconduc-
tivegelforuseinestablishingalowresistancecontactwitha
subject'sskinsurface)tomonitorskinresistanceand
conductivitywhilesubject(e.r.,subject100)isactive."

Please insert the corrected lines as follows:
--conducive to recording skin electrical properties since skin is
so pliable and flexible while the body is in motion. Also, as further
detailed below, most metals create a battery with the salts of the
skin, which in-turn produces fluctuating and ineffective readings
while this charge equalization occurs for up to sixty minutes.
In various embodiments, one or more of the physiological sign
portions (110, 120) of enhanced monitoring device 140 are
configured to use disposable electrodes (e.g., silver silver-chloride
electrodes incorporating a flexible, electrically conductive
gel for use in establishing a low resistance contact with a
subject's skin surface) to monitor skin resistance and
conductivity while a subject (e.g., subject 100) is active.--

Signed and Sealed this
Sixth Day of May, 2025

Coke Morgan Stewart
*Acting Director of the United States Patent and Trademark Office*